United States Patent
Lee et al.

(10) Patent No.: US 11,649,294 B2
(45) Date of Patent: May 16, 2023

(54) ANTI-HER2 ANTIBODY OR ANTIGEN-BINDING FRAGMENT THEREOF, AND CHIMERIC ANTIGEN RECEPTOR COMPRISING SAME

(71) Applicant: GC CELL CORPORATION, Gyeonggi-do (KR)

(72) Inventors: Jong Seo Lee, Gyeonggi-do (KR); Kyu Tae Kim, Gyeonggi-do (KR); Young Ha Lee, Seoul (KR); In Sik Hwang, Incheon (KR); Bong Kook Ko, Seoul (KR); Eunji Choi, Yongin-si (KR); You-Sun Kim, Yongin-si (KR); Jeongmin Kim, Yongin-si (KR); Miyoung Jung, Yongin-si (KR); Hoyong Lim, Yongin-si (KR); Sungyoo Cho, Yongin-si (KR)

(73) Assignee: GC Cell Corporation, Gyeonggi-do (KR)

( * ) Notice: Subject to any disclaimer, the term of this patent is extended or adjusted under 35 U.S.C. 154(b) by 1 day.

(21) Appl. No.: 16/881,650

(22) Filed: May 22, 2020

(65) Prior Publication Data
US 2020/0399397 A1   Dec. 24, 2020

Related U.S. Application Data

(63) Continuation-in-part of application No. 16/764,276, filed as application No. PCT/KR2018/013928 on Nov. 14, 2018.

(30) Foreign Application Priority Data

Nov. 14, 2017   (KR) .................... 10-2017-0151841

(51) Int. Cl.
| | |
|---|---|
| C07K 16/32 | (2006.01) |
| C07K 14/705 | (2006.01) |
| A61P 35/00 | (2006.01) |
| A61K 38/17 | (2006.01) |
| C12N 5/0783 | (2010.01) |

(52) U.S. Cl.
CPC ............ *C07K 16/32* (2013.01); *A61K 38/177* (2013.01); *A61P 35/00* (2018.01); *C07K 14/705* (2013.01); *C12N 5/0646* (2013.01); *C07K 2317/565* (2013.01)

(58) Field of Classification Search
None
See application file for complete search history.

(56) References Cited

U.S. PATENT DOCUMENTS

| | | | |
|---|---|---|---|
| 4,554,101 A | 11/1985 | Hopp | |
| 5,783,186 A | 7/1998 | Arakawa et al. | |
| 5,821,337 A | 10/1998 | Carter et al. | |
| 7,741,465 B1 | 2/2010 | Eshhar et al. | |
| 7,674,460 B2 | 3/2010 | Serrero | |
| 8,314,213 B2 | 11/2012 | Bernett et al. | |
| 8,404,811 B2 | 3/2013 | Ye et al. | |
| 9,394,368 B2 | 7/2016 | Brogdon et al. | |
| 9,624,276 B2 | 4/2017 | Young et al. | |
| 9,777,064 B2 | 10/2017 | Wang et al. | |
| 9,845,362 B2 | 12/2017 | Mukhetjee | |
| 10,124,023 B2 * | 11/2018 | Brentjens | ............... A61P 35/00 |
| 10,174,116 B2 | 1/2019 | Lee et al. | |
| 10,273,280 B2 | 4/2019 | Ma et al. | |
| 10,736,918 B2 | 8/2020 | Jensen et al. | |
| 11,197,919 B2 * | 12/2021 | Priceman | ............... C12N 15/86 |
| 2009/0285837 A1 | 11/2009 | Kao et al. | |
| 2010/0183604 A1 | 7/2010 | Ohta et al. | |
| 2014/0322275 A1 | 10/2014 | Brogdon et al. | |
| 2016/0130357 A1 | 5/2016 | Mukhetjee | |
| 2016/0340406 A1 | 11/2016 | Zhao et al. | |
| 2017/0151281 A1 | 6/2017 | Wagner et al. | |
| 2017/0190786 A1 | 7/2017 | Fendly et al. | |
| 2017/0313759 A1 | 11/2017 | Batuwangala | |
| 2017/0335281 A1 | 11/2017 | Loew et al. | |
| 2018/0079824 A1 | 3/2018 | Ahmed et al. | |
| 2018/0326032 A1 | 11/2018 | Priceman et al. | |
| 2019/0037831 A1 | 2/2019 | Hwang et al. | |
| 2019/0336533 A1 | 11/2019 | Hwang et al. | |
| 2020/0108096 A1 | 4/2020 | Min et al. | |

(Continued)

FOREIGN PATENT DOCUMENTS

| | | |
|---|---|---|
| CA | 2402930 | 3/2004 |
| CN | 104177499 | 12/2014 |

(Continued)

OTHER PUBLICATIONS

Sun et al. (2014) (Construction and evaluation of a novel humanized HER2 specific chimeric receptor, Breast Cancer Research, vol. 16, 2014) (Year: 2014).*
Hu et al., "Epitope mapping and structural analysis of an anti-ErbB2 antibody A21: Molecular basis for tumor inhibitoty mechanism," Proteins, Februaty 15, 2008, 70(3):938-949.
Office Action in Japanese Appln. No. 2020-544730, dated Dec. 14, 2021, 11 pages (with English Translation).
Office Action in Japanese Appln. No. 2020-544730, dated May 23, 2022, 4 pages (with English Translation).
Rockberg et al., "Discovery of epitopes for targeting the human epidermal growth factor receptor 2 (HER2) with antibodies," Molecular Oncology, Jun. 2009, 3(3):238-247.

(Continued)

*Primary Examiner* — Laura B Goddard
*Assistant Examiner* — Sarah A Alsomairy
(74) *Attorney, Agent, or Firm* — Fish & Richardson P.C.

(57) ABSTRACT

The present disclosure relates to a novel anti-HER2 antibody or an antigen-binding fragment thereof used in the prevention or treatment of cancer, a chimeric antigen receptor including the same, and uses thereof. The antibody of the present disclosure is an antibody that specifically binds to HER2 which is highly expressed in cancer cells (particularly, breast cancer or gastric cancer cells), and binds to an epitope that is different from an epitope to which trastuzumab binds.

24 Claims, 26 Drawing Sheets
Specification includes a Sequence Listing.

(56) References Cited

U.S. PATENT DOCUMENTS

| | | |
|---|---|---|
| 2021/0147803 A1 | 5/2021 | Hwang et al. |
| 2021/0179733 A1 | 6/2021 | Lee et al. |

FOREIGN PATENT DOCUMENTS

| | | | |
|---|---|---|---|
| CN | 105246504 | 1/2016 | |
| JP | 2010-006705 | 1/2010 | |
| JP | 2013-534809 | 9/2013 | |
| JP | 2016508725 | 3/2016 | |
| JP | 2016518368 | 6/2016 | |
| KR | 10-1453462 | 10/2014 | |
| KR | 10-2015-0048783 | 5/2015 | |
| KR | 10-2016-0015195 | 2/2016 | |
| KR | 10-2016-0022857 | 3/2016 | |
| KR | 10-2016-0062760 | 6/2016 | |
| WO | WO 1994/00136 | 1/1994 | |
| WO | WO 2011/127297 | 10/2011 | |
| WO | WO 2014/130657 | 8/2014 | |
| WO | WO 2014/185704 | 11/2014 | |
| WO | WO 2015/164594 | 10/2015 | |
| WO | WO 2016/176639 | 3/2016 | |
| WO | WO 2016/120219 | 8/2016 | |
| WO | WO 2016/123333 | 8/2016 | |
| WO | WO 2016/174652 | 11/2016 | |
| WO | WO 2017/079694 | 5/2017 | |
| WO | WO 2017/079705 | 5/2017 | |
| WO | WO 2017/167967 | 10/2017 | |
| WO | WO 2017/222593 | 12/2017 | |
| WO | WO 2018/140725 | 8/2018 | |
| WO | WO-2019030757 A1 * | 2/2019 | ............ A61K 35/17 |
| WO | WO 2019/098682 | 5/2019 | |
| WO | WO 2019/160501 | 8/2019 | |
| WO | WO 2019/1823 92 | 9/2019 | |
| WO | WO 2020/101361 | 5/2020 | |
| WO | WO 2022/133057 | 6/2022 | |

OTHER PUBLICATIONS

AU Office Action in Australian Appln. No. 2018370195, dated Jul. 6, 2021, 5 pages.

Extended European Search Report in European Patent Appln No. 18878132.2, dated Jul. 14, 2021, 10 pages.

Nahta et al., "The HER-2-Targeting Antibodies Transtuzumab and Pertuzumab Synergistically Inhibit the Survival of Breast Cancer Cells", Cancer Research, Apr. 2004, 64(7): 2343-2346.

Yamashita-Kashima et al., "Pertuzumab in Combination with Trastuzumab Shows Significantly Enhanced Antitumor Activity in HER2-Positive Human Gastric Cancer Xenograft Models", Clinical Cancer Research, Jun. 2011, 17(15):5060-5071.

Croft et al., "Regulation of T Cell Immunity by OX40 and OX40L," Madame Curie Bioscience Database, 2000-2013, retrieved on Jan. 12, 2022, retrieved from URL <"https://www.ncbi.nlm.nih.gov/books/NBK5990/">, 12 pages.

Webb et al., "OX40, OX40L and Autoimmunity: a Comprehensive Review," Clinic Rev. Allerg. Immunol., 2016, 50: 312-332.

Akiyama et al., "The product of the human c-erbB-2 gene: a 185-kilodalton glycoprotein with tyrosine kinase activity," Science, Jun. 27, 1986, 232(4758): 1644-1646.

Altschul et al., "Basic local alignment search tool," Journal of Molecular Biology, Oct. 5, 1990, 215(3):403-410.

Arteaga et al., "p185c-erbB-2 Signaling Enhances Cisplatin-induced Cytotoxicity in Human Breast Carcinoma Cells: Association between an Oncogenic Receptor Tyrosine Kinase and Drug-induced DNA Repair," Cancer Research, Jul. 1994, 54:3758-3765.

Bacus et al., "Differentiation of cultured human breast cancer cells (AU-565 and MCF-7) associated with loss of cell surface HER-2/neu antigen," Molecular Carcinogenesis, 1990, 3:350-362.

Bacus et al., "Tumor-inhibitory Monoclonal Antibodies to the HER-2/Neu Receptor Induce Differentiation of Human Breast Cancer Cells," Cancer Research, May 1992, 52:2580-2589.

Bussolati et al., "A modified Trastuzumab antibody for the immunohistochemical detection of HER-2 overexpression in breast cancer," British Journal of Cancer, Apr. 5, 2005, 92:1261-1267.

Corpet, "Multiple sequence alignment with hierarchical clustering," Nuc. Acids Res., Nov. 25, 1988, 16(22): 10881-10890.

Crossland, "CD56-Specific T Cells; Using Genetically Engineered T Cells to Redirect Specificty to a T Cell Expressed Antigen" Dissertation for the degree of PhD, The University of Texas MD Anderson Cancer Center UTHealth Graduate School of Biomedical Sciences, Aug. 2014, 232 pages.

Gacerez et al., "How chimeric antigen receptor design affects adoptive T cell therapy" J. Cell Physiol., Dec. 2016, 231(12):2590-8.

GenBank Accession No. AB590584.1, "Synthetic construct DNA, clone: pFN21AE1768, Homo sapiens TNFRSF4 gene for tumor necrosis factor receptor superfamily, member 4, without stop codon, in Flexi system," Jul. 25, 2016, 2 pages.

GenBank Accession No. AF461811.1, "Homo sapiens NKG2D mRNA, complete cds" Jan. 17, 2002, 2 pages.

GenBank Accession No. N_000734.3, "Homo sapiens CD247 molecule (CD247), transcript variant 2, mRNA" Mar. 15, 2015, 5 pages.

GenBank Accession No. NM_001561.5, "Homo sapiens tumor necrosis factor receptor superfamily member 9 (TNFRSF9), mRNA" Nov. 20, 2015, 5 pages.

GenBank Accession No. NM_001768.6, "Homo sapiens CD8a molecule (CD8A), transcript variant 1, Mrna," Mar. 15, 2015, 4 pages.

GenBank Accession No. NM_003326.4, "Homo sapiens TNF superfamily member 4 (TNFSF4), transcript variant 1, mRNA" Nov. 21, 2015, 4 pages.

GenBank Accession No. NM_006139.3, "Homo sapiens CD28 molecule (CD28), transcript variant 1, mRNA," Mar. 15, 2015, 5 pages.

GenBank Accession No. X52645.1 "Human Fc-gamma RIII-2 cDNA for Fc-gamma receptor III-2 (CD16)," Oct. 7, 2008, 2 pages.

Glazyrin et al., "Direct Detection of Herceptin/Transtuzumab Binding on Breast Tissue Sections," J Histology & Cytochemistry, 2007, 55(1):25-33.

Hancock et al., "A Monoclonal Antibody against the c-erbB-2 Protein Enhances the Cytotoxicity of cis-Diamminedichloroplatinum against Human Breast and Ovarian Tumor Cell Lines," Cancer Res., Sep. 1, 1991, 51:4575-4580.

Harwerth et al., "Monoclonal Antibodies against the Extracellular Domain of erbB-2 Receptor Fuction as Partial Lgand Agonists," J Biol. Chem., Jul. 25, 1992, 267(21):15160-15167.

Higgins et al., "CLUSTAL: a packate for performing multiple sequence alignment on a microcomputer," Gene, 1988, 73:237-244.

Higgins et al., "Fast and sensitive multiple sequence alignments on a microcomputer," CABIOS COMMUICATIONS, 1989, 5(2):151-153.

Huang et al., "Parallelization of a local similarity algorithm," CABIOS, 1992, 8(2):155-165.

JP Office Action in Japanese Appln. No. 2020-544730, dated May 26, 2021, 12 pages (with English Translation).

Kasprzyk et al., "Therapy of an Animal Model of Human Gastric Cancer Using a Combination of Anti-erbB-2 Monoclonal Antibodies," Cancer Research, May 15, 1992, 52:2771-2776.

Klapper et al., "A subclass of tumor inhibitory monoclonal antibodies to ErbB-2/HER2 blocks crosstalk with growth factor receptors," Oncogene, Jan. 1997, 14:2099-2109.

Maier et al., "Requirements for the Internalization of a Murine Monoclonal Antibody Directed against the HER-2/neu Gene Product c-erbB-2," Cancer Res., Oct. 1, 1991, 51:5361-5369.

Needleman et al., "A General Method Applicable to the Search for Similarities in the Amino Acid Sequence of Two Proteins," J Mol. Biol., 1970, 48:443-453.

PCT International Preliminary Report on Patentability in International Appln. No. PCT/KR2018/013928, dated May 19, 2020, 17 pages (with English Translation).

PCT International Search Report and Written Opinion in International Appln. No. PCT/KR2018/013928, dated Mar. 15, 2019, 25 pages (with English Translation).

(56) References Cited

OTHER PUBLICATIONS

Ross et al., "The HER-2/neu Gene and Protein in Breast Cancer2003: Biomarker and Target of Therapy," The Oncologist, 2003, 8(4):307-325, 19 pages.
Sapino et al., "Patients with advanced stage breast carcinoma immunoreactive to biotinylated Herceptin® are most likely to benefit from trastuzumab-based therapy: an hypothesis-generating study," Annals of Oncology, Dec. 2007, 18(12):1963-1968, 6 pages.
Shawver et al., "Ligand-like Effects Induced by Anti-c-erbB-2 Antibodies Do Not Correlate with and Are Not Required for Growth Inhibition of Human Carcinoma Cells," Cancer Res., Mar. 1, 1994, 54:1367-1373.
Smith et al., "Comparison of biosequences," Adv. Appl. Math., Dec. 1981, 2(4):482-489.
Stancovski et al., "Mechanistic aspects of the opposing effects of monoclonal antibodies to the ERBB2 receptor on tumor growth," PNAS USA, Oct. 1, 1991, 88(19):8691-8695.
Tagliabue et al., "Selection of monoclonal antibodies which induce internalization and phosphorylation of P185HER2 and growth inhibition of cells with HER2/neu gene amplification," Int. J Cancer, Apr. 1, 1991, 47(6):933-937.
Uhlman et al., "Antisense oligonucleotides: a new therapeutic principle," Chemical Reviews, Jun. 1, 1990, 90(4):543-584.
Wilkie et al., "Retargeting of Human T Cells to Tumor-Associated MUC1: The Evolution of a Chimeric Antigen Receptor," The Journal of Immunology, 2008, 180:4901-9.
Xu et al., "Antibody-induced growth inhibition is mediated through immunochemically and functionally distinct epitopes on the extracellular domain of the c-erbb-2 (her-2/neu) gene product p185," Int. J Cancer, Feb. 1, 1993, 53:401-408.
International Search Report and Written Opinion in International Appln. No. PCT/KR2021/006361, dated Nov. 25, 2021, 14 pages.
U.S. Appl. No. 16/474,426 (Corresponds to US 2021/0179733 cited in an IDS on Jul. 16, 2021), Hwang et al., filed Jun. 27, 2019.
U.S. Appl. No. 16/764,276 (Corresponds to US 2021/0179733 cited in an IDS on Jan. 19, 2022), Lee et al., filed Sep. 28, 2020.
U.S. Appl. No. 17/845,793, Hwang et al., filed Jun. 21, 2022.
Sadelain et al., "The Basic Principles of Chimeric Antigen Receptor Design," Cancer Discovery, Apr. 2013, 3:388-398.

* cited by examiner

| Clone # | Signal Peptide | Tumor Targeting Domain | Hinge | Transmembrane Domain | Stimulatory Signal 1 | Stimulatory Signal 2 | Stimulatory Signal 3 |
|---|---|---|---|---|---|---|---|
| 2 | CD8a | hz39D2 | CD8a | CD8a | CD3z | | |
| 3 | CD8a | hz39D2 | CD8a | CD8a | 4-1BB | CD3z | |
| 6 | CD8a | hz39D2 | CD8a | CD8a | CD28 | CD3z | |
| 14 | CD8a | hz39D2 | CD8a | CD28 | CD28 | OX40L | CD3z |

FIG. 7

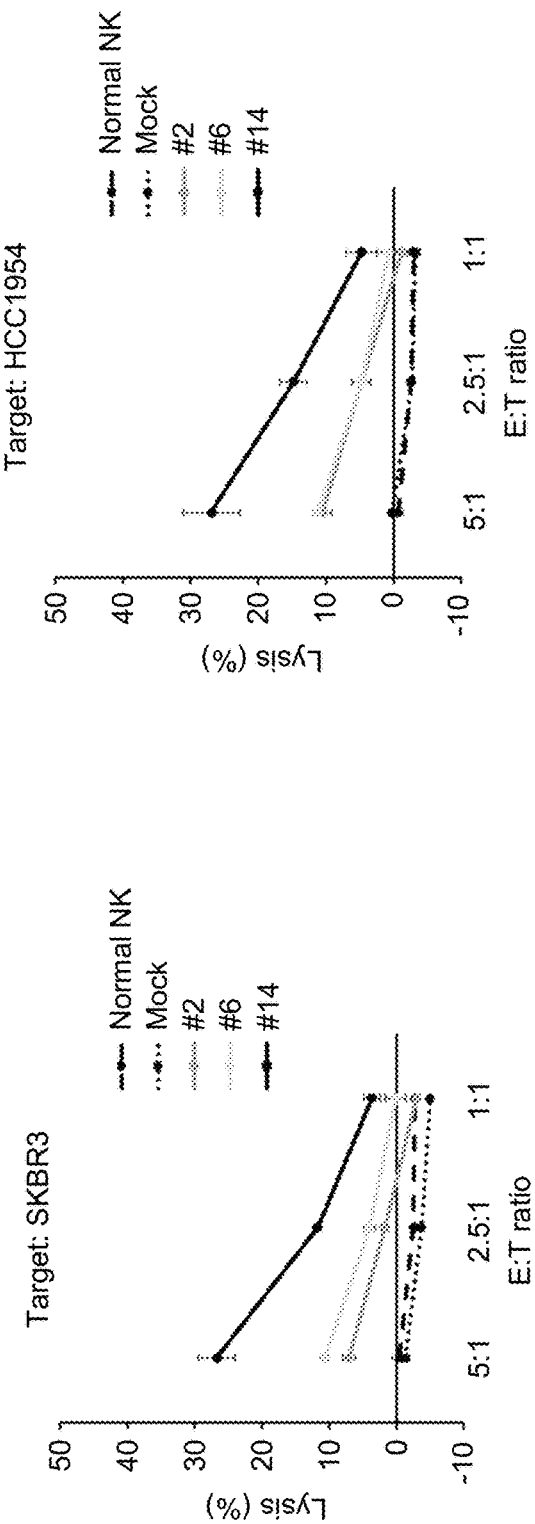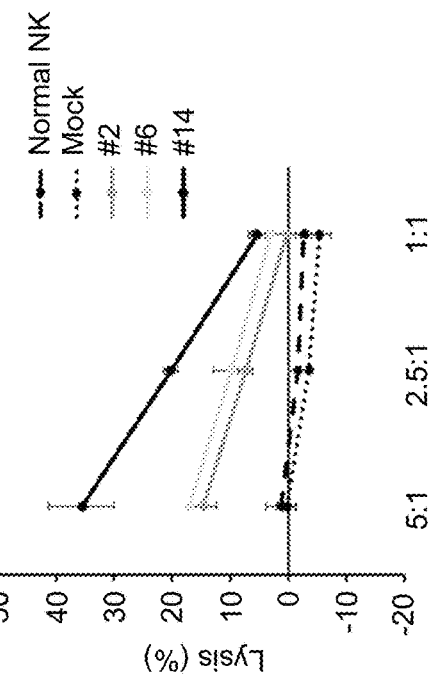
FIG. 8A
FIG. 8B
FIG. 8C

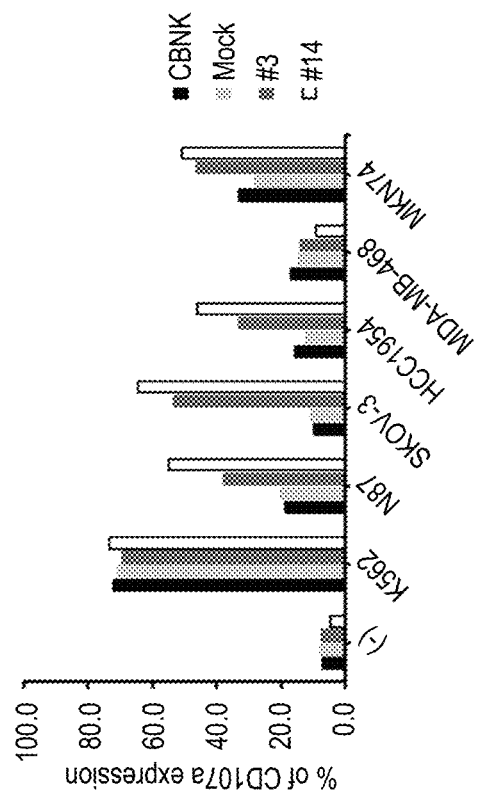
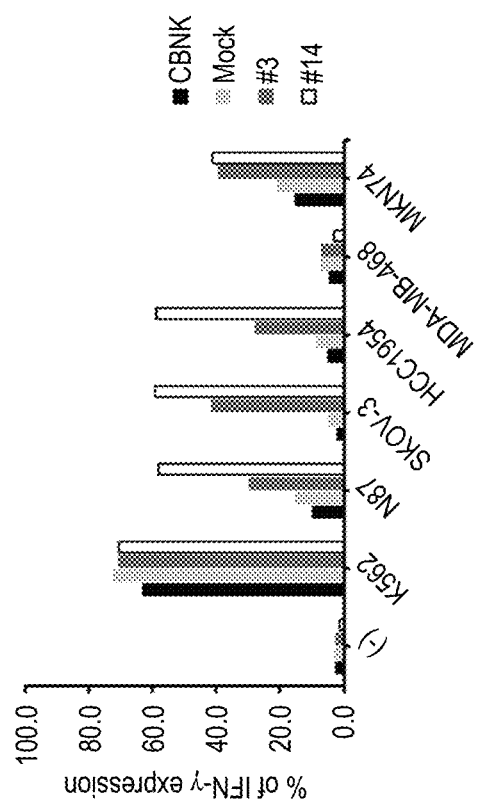
FIG. 11A
FIG. 11B

ANTI-HER2 ANTIBODY OR ANTIGEN-BINDING FRAGMENT THEREOF, AND CHIMERIC ANTIGEN RECEPTOR COMPRISING SAME

REFERENCE TO SEQUENCE LISTING SUBMITTED ELECTRONICALLY

The instant application includes a Sequence Listing which has been submitted electronically in ASCII and is hereby incorporated by reference in its entirety. Said ASCII copy, created on May 5, 2020, is named 4411-0210002_Sequences_ST25.txt and is 151,877 bytes in size.

TECHNICAL FIELD

The research was conducted under the support of the Ministry of Trade, Industry and Energy of Korea with the project number 1415118385. The R&D management agency of the project is the Korea Institute for Advancement of Technology, the R&D project title is "Global innovation technology alliance", and the research title is "Development of global antibody drug based on novel epitope screening platform technology". The research was conducted by AbClon Inc. from Nov. 1, 2011 until Oct. 31, 2014.

This application claims the priority of Korean Patent Application No. 10-2017-0151841 filed on Nov. 14, 2017 in the Korean Intellectual Property Office, the disclosure of which is incorporated herein by reference in its entirety.

The present disclosure relates to a novel anti-HER2 antibody or an antigen-binding fragment thereof, a chimeric antigen receptor including the same, and uses thereof.

BACKGROUND ART

The Her2/neu (ErbB2) gene encodes a 185-kDa transmembrane glycoprotein that belongs to the family of epidermal growth factor receptors (EGFRs). The Her2 protein is composed of an extracellular domain consisting of 620 amino acid residues, a transmembrane domain 23 amino acid residues, and an intracellular domain with tyrosine kinase activity, consisting of 490 amino acid residues (Akiyama T, et al., *Science*, 232 (4758): 1644-1646 (1986)).

Anti-HER2 antibodies with various characteristics have been described: Tagliabue et al., *Int. J Cancer* 47: 933-937 (1991); McKenzie et al., *Oncogene* 4: 543-548 (1989); Maier et al., *Cancer Res.* 51: 5361-5369 (1991); Bacus et al., *Molecular Carcinogenesis* 3: 350-362 (1990); Stancovski et al., *PNAS USA* 88: 8691-8695 (1991); Bacus et al., *Cancer Research* 52: 2580-2589 (1992); Xu et al., *Int. J Cancer* 53: 401-408 (1993); WO94/00136; Kasprzyk et al., *Cancer Research* 52: 2771-2776 (1992); Hancock et al., *Cancer Res.* 51: 4575-4580 (1991); Shawver et al., *Cancer Res.* 54: 1367-1373 (1994); Arteaga et al., *Cancer Res.* 54: 3758-3765 (1994); Harwerth et al., *J. Biol. Chem.* 267: 15160-15167 (1992); U.S. Pat. No. 5,783,186; Kao et al., US Patent Application Publication No. 2009/0285837 (2009); Ross et al., *The Oncologist* 8: 307-325 (2003); and Klapper et al., *Oncogene* 14: 2099-2109 (1997).

The most commercially successful anti-HER2 antibody is trastuzumab antibody (commercially available as Herceptin™, U.S. Pat. No. 5,821,337) and many researches have been conducted thereon: Sapino, A., et al., *Annals of Oncology* (2007) 18: 1963-1968; Bussolati, G, et al., *British Journal of Cancer* (2005) 92, 1261-1267; and Glazyrin A, et al., *J Histology & Cytochemistry* (2007) 55 (1): 25-33.

Although the trastuzumab antibody has been commercially successful, use of the trastuzumab antibody for therapeutic purposes is limited because there are various cancer cells which have non-reactivity (or resistance) to the antibody or have reduced sensitivity. Accordingly, there have been attempts to resolve the therapeutic problem of the antibody.

For example, U.S. Pat. No. 7,674,460 discloses a method for increasing the HER2 sensitivity of cancer cells using an HER2 antagonist such as the trastuzumab antibody and a PC cell-derived growth factor (PCDGF) antagonist. WO 2011/127297 discloses a method for inhibiting the proliferation of trastuzumab-resistant tumor cells using a combination of a FoxMl inhibitor and the trastuzumab antibody.

US Patent Application Publication No. 2010-0183604 discloses a method for treating trastuzumab-resistant cancer using a cofilin inhibitor, a PAK1 inhibitor, a LIMK inhibitor, an RHO inhibitor, a ROCK1 inhibitor or a ROCK2 inhibitor.

DISCLOSURE

Technical Problem

The inventors of the present disclosure have made efforts to develop a novel antibody which is capable of preventing or treating cancer (particularly, breast cancer and gastric cancer), exhibits better killing ability (or proliferation-inhibiting ability) for cancer cells which have non-reactivity (or resistance) to the trastuzumab antibody or have reduced sensitivity, and is capable of preventing or treating cancer with improved anticancer activity when co-administered with the trastuzumab antibody as compared to single administration of trastuzumab. As a result, they have developed a novel antibody which exhibits better killing ability for HER2-overexpressed cancer cells on which the trastuzumab antibody hardly acts, or exhibits improved anticancer activity when co-administered with the trastuzumab antibody, and have completed the present disclosure.

SUMMARY OF THE INVENTION

The present disclosure provides an antibody or an antigen binding fragment thereof against HER2 (human epidermal growth factor receptor 2) comprising any one of: (a) a heavy chain variable region comprising a CDRH1 of SEQ ID NO 1, a CDRH2 of SEQ ID NO 2 and a CDRH3 of SEQ ID NO 3, and a light chain variable region comprising a CDRL1 of SEQ ID NO 4, a CDRL2 of SEQ ID NO 5 and a CDRL3 of SEQ ID NO 6; (b) a heavy chain variable region comprising a CDRH1 of SEQ ID NO 7, a CDRH2 of SEQ ID NO 8 and a CDRH3 of SEQ ID NO 9, 71 or 72, and a light chain variable region comprising a CDRL1 of SEQ ID NO 10, a CDRL2 of SEQ ID NO 11 and a CDRL3 of SEQ ID NO 12, 73 or 74; (c) a heavy chain variable region comprising a CDRH1 of SEQ ID NO 13, a CDRH2 of SEQ ID NO 14 and a CDRH3 of SEQ ID NO 15, and a light chain variable region comprising a CDRL1 of SEQ ID NO 16, a CDRL2 of SEQ ID NO 17 and a CDRL3 of SEQ ID NO 18; (d) a heavy chain variable region comprising a CDRH1 of SEQ ID NO 19, a CDRH2 of SEQ ID NO 20 and a CDRH3 of SEQ ID NO 21, and a light chain variable region comprising a CDRL1 of SEQ ID NO 22, a CDRL2 of SEQ ID NO 23 and a CDRL3 of SEQ ID NO 24; or (d) a heavy chain variable region comprising a CDRH1 of SEQ ID NO 25, a CDRH2 of SEQ ID NO 26 and a CDRH3 of SEQ ID NO 27, and a light chain variable region comprising a CDRL1 of SEQ ID NO 28, a CDRL2 of SEQ ID NO 29 and a CDRL3 of SEQ ID NO 30.

In some aspects of the disclosure, the heavy chain variable region of (a) comprises an amino acid sequence of SEQ ID NO 31 or 75; the heavy chain variable region of (b) comprises an amino acid sequence of SEQ ID NO 39, 83, 87, 95 or 103; the heavy chain variable region of (c) comprises an amino acid sequence of SEQ ID NO 47; the heavy chain variable region of (d) comprises an amino acid sequence of SEQ ID NO 55; and the heavy chain variable region of (e) comprises an amino acid sequence of SEQ ID NO 63 or 79.

In some aspects of the disclosure, the light chain variable region of (a) comprises an amino acid sequence of SEQ ID NO 35 or 77; the light chain variable region of (b) comprises an amino acid sequence of SEQ ID NO 43, 85, 91, 99 or 107; the light chain variable region of (c) comprises an amino acid sequence of SEQ ID NO 51; the light chain variable region of (d) comprises an amino acid sequence of SEQ ID NO 59; and the light chain variable region of (e) comprises an amino acid sequence of SEQ ID NO 67 or 81.

In some aspects of the disclosure, the antibody or the antigen-binding fragment thereof comprising (a) comprises a heavy chain comprising an amino acid sequence of SEQ ID NO 33; the antibody or the antigen-binding fragment thereof comprising (b) comprises a heavy chain comprising an amino acid sequence of SEQ ID NO 41, 89, 97 or 105; the antibody or the antigen-binding fragment thereof comprising (c) comprises a heavy chain comprising an amino acid sequence of SEQ ID NO 49; the antibody or the antigen-binding fragment thereof comprising (d) comprises a heavy chain comprising an amino acid sequence of SEQ ID NO 57; and the antibody or the antigen-binding fragment thereof comprising (e) comprises a heavy chain comprising an amino acid sequence of SEQ ID NO 65.

In some aspects of the disclosure, the antibody or the antigen-binding fragment thereof comprising (a) comprises a light chain comprising an amino acid sequence of SEQ ID NO 37; the antibody or the antigen-binding fragment thereof comprising (b) comprises a light chain comprising an amino acid sequence of SEQ ID NO 45, 93, 101 or 109; the antibody or the antigen-binding fragment thereof comprising (c) comprises a light chain comprising an amino acid sequence of SEQ ID NO 53; the antibody or the antigen-binding fragment thereof comprising (d) comprises a light chain comprising an amino acid sequence of SEQ ID NO 61; and the antibody or the antigen-binding fragment thereof comprising (e) comprises a light chain comprising an amino acid sequence of SEQ ID NO 69.

The present disclosure further provides a fusion protein comprising the antibody or the antigen-binding fragment as described herein.

The present disclosure further provides a chimeric antigen receptor polypeptide comprising an HER2-binding domain; a transmembrane domain (TM); a costimulatory domain; and an intracellular signaling domain (ICD).

In some aspects of the disclosure, the HER2-binding domain comprises the antibody or the antigen-binding fragment thereof as described herein.

In some aspects of the disclosure, the transmembrane domain is a transmembrane domain of a protein selected from a group consisting of T-cell receptor alpha, beta or zeta chain, CD28, CD3 epsilon, CD45, CD4, CD5, CD8, CD9, CD16, CD22, CD33, CD37, CD64, CD80, CD86, CD134, CD137 and CD154.

In some aspects of the disclosure, the costimulatory domain is a functional signaling domain obtained from a protein selected from a group consisting of MHC class I molecule, TNF receptor protein, immunoglobulin-like protein, cytokine receptor, integrin, signaling lymphocytic activation molecule (SLAM), activating NK cell receptor, BTLA (B- and T-lymphocyte attenuator), Toll-like ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand binding specifically to CD83.

In some aspects of the disclosure, the intracellular signaling domain comprises a functional signaling domain of 4-1BB, CD28, OX40 or CD3 zeta, or a combination thereof.

In some aspects of the disclosure, the intracellular signaling domain comprises a functional signaling domain of OX40 ligand.

The present disclosure further provides a nucleic acid molecule encoding the anti-HER2 antibody or the antigen-binding fragment thereof as described herein.

The present disclosure further provides a nucleic acid molecule encoding the chimeric antigen receptor polypeptide as described herein.

The present disclosure further provides a recombinant vector comprising the nucleic acid molecule encoding the anti-HER2 antibody or the antigen-binding fragment thereof as described herein or the chimeric antigen receptor polypeptide as described herein.

The present disclosure further provides a host cell transformed with the recombinant vector as described herein.

The present disclosure further provides an effector cell expressing the chimeric antigen receptor polypeptide as described herein.

In some aspects of the disclosure, the effector cell is selected from a group consisting of a dendritic cell, a killer dendritic cell, a mast cell, a natural killer cell, a B lymphocyte, a T lymphocyte, a macrophage and precursor cells thereof.

In some aspects of the disclosure, the T lymphocyte is selected from a group consisting of an inflammatory T lymphocyte, a cytotoxic T lymphocyte, a regulatory T lymphocyte or a helper T lymphocyte.

The present disclosure further provides a pharmaceutical composition for preventing or treating cancer, comprising a pharmaceutically effective amount of the anti-HER2 antibody or the antigen-binding fragment thereof as described herein a pharmaceutically acceptable carrier.

The present disclosure further provides a pharmaceutical composition for treating cancer, comprising the effector cell expressing the chimeric antigen receptor polypeptide as described herein.

In some aspects of the disclosure, the cancer is breast cancer, ovarian cancer, gastric cancer, lung cancer, liver cancer, bronchial cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer or ureteral cancer.

In some aspects of the disclosure, the pharmaceutical composition further comprises the trastuzumab antibody.

The present disclosure further provides a kit for diagnosing cancer, comprising the anti-HER2 antibody or the antigen-binding fragment thereof as described herein.

The present disclosure further provides a chimeric antigen receptor comprising an extracellular domain that binds Her2, wherein the extracellular domain comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 113 (hz39D2 (VL-GS linker-VH)).

In some aspects of the disclosure, the chimeric antigen receptor further comprises an extracellular signaling domain linked to the extracellular domain; a hinge domain linked to the extracellular domain; a transmembrane domain linked to the hinge domain; and an intracellular stimulatory signal linked to the hinge domain.

In some aspects of the disclosure, the extracellular signaling domain comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 111 (CD8a signal peptide). In some aspects, the extracellular signaling domain comprises SEQ ID NO: 111 (CD8a signal peptide).

In some aspects of the disclosure, the hinge domain comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 115 (CD8a hinge). In some aspects of the disclosure, the hinge domain comprises SEQ ID NO: 115 (CD8a hinge).

In some aspects of the disclosure, the transmembrane domain comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 117 (CD8a TM) or SEQ ID NO: 119 (CD28 TM). In some aspects of the disclosure, the transmembrane domain comprises SEQ ID NO: 117 CD8a TM) or SEQ ID NO: 119 (CD28 TM).

In some aspects of the disclosure, the intracellular stimulatory signal comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 121 (CD3-ζ). In some aspects, the intracellular stimulatory signal comprises SEQ ID NO: 121 (CD3-ζ).

In some aspects of the disclosure, the chimeric antigen receptor further comprises a second intracellular stimulatory signal, wherein the second intracellular stimulatory signal comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 123 (4-1BB) or SEQ ID NO: 125 (CD28). In some aspects of the disclosure, the second intracellular stimulatory signal comprises SEQ ID NO: 123 (4-1BB) or SEQ ID NO: 125 (CD28).

In some aspects of the disclosure, the chimeric antigen receptor further comprises a third intracellular stimulatory signal, wherein the third intracellular stimulatory signal comprises an amino acid sequence having at least 80%, at least 85%, at least 90%, at least 91%, at least 92%, at least 93%, at least 94%, at least 95%, at least 96%, at least 97%, at least 98%, or at least 99% sequence identity with SEQ ID NO: 127 (OX40L). In some aspects of the disclosure, wherein the third intracellular stimulatory signal comprises SEQ ID NO: 127 (OX40L).

In some aspects of the disclosure, the chimeric antigen receptor comprises an amino acid sequence having at least 80%, at least 85%, at least 90%, at least 91%, at least 92%, at least 93%, at least 94%, at least 95%, at least 96%, at least 97%, at least 98%, or at least 99% sequence identity to SEQ ID NO: 129 (Clone 2), SEQ ID NO: 131 (Clone 3), SEQ ID NO: 133 (Clone 6), or SEQ ID NO: 135 (Clone 14). In some aspects of the disclosure, the chimeric antigen receptor comprises SEQ ID NO: 129 (Clone 2), SEQ ID NO: 131 (Clone 3), SEQ ID NO: 133 (Clone 6), or SEQ ID NO: 135 (Clone 14).

The present disclosure further provides a nucleic acid molecule encoding the chimeric antigen receptor having an extracellular domain comprising an amino acid sequence with at least 80%, at least 85%, at least 90%, at least 91%, at least 92%, at least 93%, at least 94%, at least 95%, at least 96%, at least 97%, at least 98%, or at least 99% sequence identity to SEQ ID NO: 113 (hz39D2 (VL-GS linker-VH)) as described herein.

The present disclosure further provides a vector comprising the nucleic acid molecule encoding the chimeric antigen receptor having an extracellular domain comprising an amino acid sequence with at least 80%, at least 85%, at least 90%, at least 91%, at least 92%, at least 93%, at least 94%, at least 95%, at least 96%, at least 97%, at least 98%, or at least 99% sequence identity to SEQ ID NO: 113 (hz39D2 (VL-GS linker-VH)) as described herein.

The present disclosure further provides an immune cell expressing the chimeric antigen having an extracellular domain comprising an amino acid sequence with at least 80%, at least 85%, at least 90%, at least 91%, at least 92%, at least 93%, at least 94%, at least 95%, at least 96%, at least 97%, at least 98%, or at least 99% sequence identity to SEQ ID NO: 113 (hz39D2 (VL-GS linker-VH)) as described herein.

In some aspects of the disclosure, the immune cell is a natural killer cell.

The present disclosure further provides a pharmaceutical composition comprising the immune cell as described herein and a pharmaceutically acceptable carrier.

The present disclosure further provides a method for treating cancer comprising administering to a subject in need thereof a therapeutically effective amount of the pharmaceutical composition as described herein.

In some aspects of the disclosure, the cancer is selected from the group consisting of breast cancer, ovarian cancer, gastric cancer, lung cancer, liver cancer, bronchial cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer and ureteral cancer.

BRIEF DESCRIPTION OF DRAWINGS

FIG. 7 is a table providing a summary of HER2-CAR constructs according to the present disclosure.

FIGS. 8A-8C are line graphs showing the results of a cell killing assay (Calcein releasing cytotoxicity assay) assessing the cytotoxicity of cord-blood derived NK cells (CBNKs) expressing HER2-CAR constructs against HER2 positive target cancer cell lines.

FIGS. 11A-11B are bar graphs showing the NK cell degranulation activity and cytotoxic cytokine expression with the various HER2-CAR constructs evaluated by comparing intercellular expression level of CD107a and IFN-γ.

DETAILED DESCRIPTION OF THE INVENTION

Figure 1:
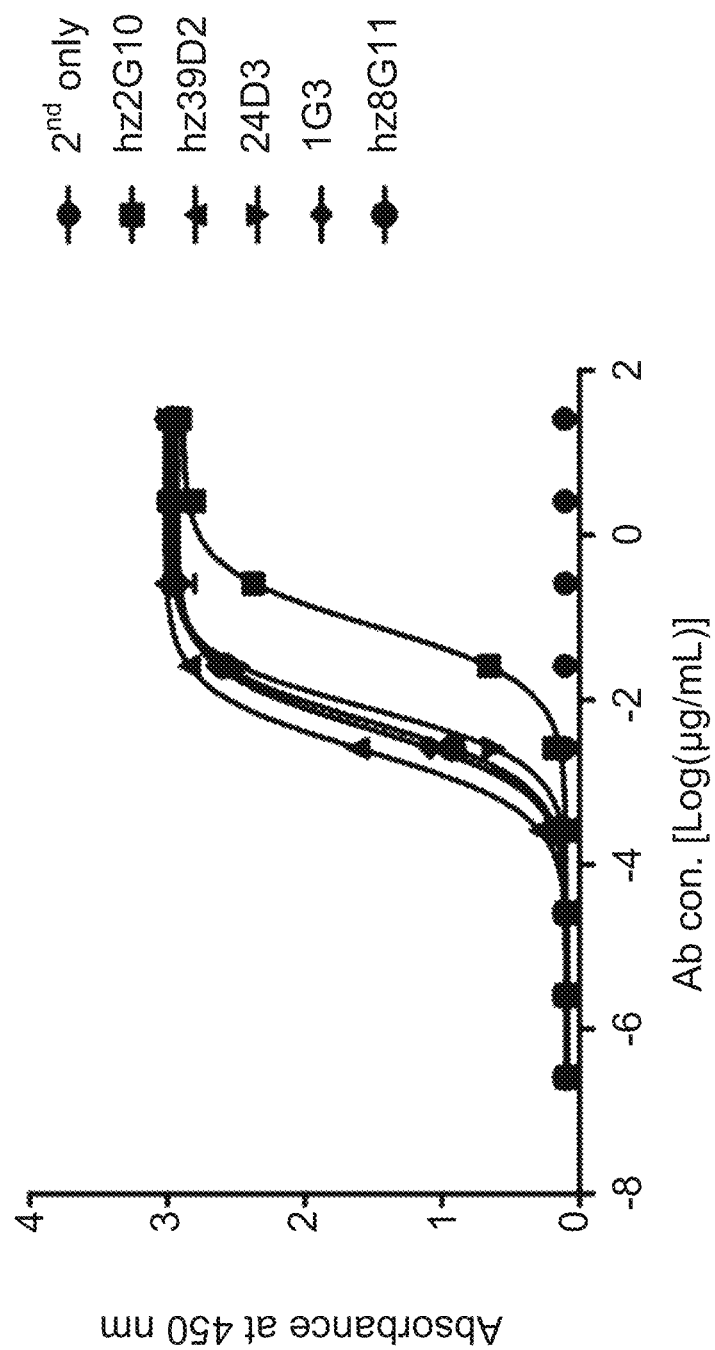
FIG. 1 is a line graph showing the a results of analyzing the affinity of hz2G10, hz39D2, 24D3, 1G3 and hz8G11 clones for the HER2-ECD-Fc antigen by ELISA.

The present disclosure is directed to providing an antibody (anti-HER2 antibody) against HER2 (human epidermal growth factor receptor 2) or an antigen-binding fragment thereof.

The present disclosure is also directed to providing a fusion protein including the anti-HER2 antibody or an antigen-binding fragment thereof.

The present disclosure is also directed to providing a chimeric antigen receptor (CAR) including the anti-HER2 antibody or an antigen-binding fragment thereof and an effector cell expressing the same.

The present disclosure is also directed to providing a nucleic acid molecule encoding the anti-HER2 antibody or an antigen-binding fragment thereof; or the chimeric antigen receptor.

The present disclosure is also directed to providing a recombinant vector including the nucleic acid molecule.

The present disclosure is also directed to providing a host cell transformed with the recombinant vector.

The present disclosure is also directed to providing a pharmaceutical composition for preventing or treating cancer, which contains the anti-HER2 antibody or an antigen-binding fragment thereof.

The present disclosure is also directed to providing a kit for diagnosing cancer, which includes the anti-HER2 antibody or an antigen-binding fragment thereof.

The present disclosure is also directed to providing a method for preventing or treating cancer by administering a composition containing the anti-HER2 antibody or an antigen-binding fragment thereof to a subject.

The present disclosure is also directed to providing a method for treating a disease related with HER2 overexpression (e.g., cancer) by administering an effector cell expressing the chimeric antigen receptor to a subject.

Technical Solution

The present disclosure provides an antibody binding specifically to HER2 (human epidermal growth factor receptor 2) and modified antibodies thereof that have undergone affinity maturation.

A first aspect of the present disclosure provides an antibody against HER2 (human epidermal growth factor receptor 2) including the followings or an antigen-binding fragment thereof:

(a) a heavy chain variable region including the following heavy chain CDR (complementarity-determining region) amino acid sequences:
CDRH1 of SEQ ID NO 1, CDRH2 of SEQ ID NO 2 and CDRH3 of SEQ ID NO 3; and (b) a light chain variable region including the following light chain CDR amino acid sequences:
CDRL1 of SEQ ID NO 4, CDRL2 of SEQ ID NO 5 and CDRL3 of SEQ ID NO 6.

A second aspect of the present disclosure provides an antibody against HER2 (human epidermal growth factor receptor 2) including the followings or an antigen-binding fragment thereof:

(a) a heavy chain variable region including the following heavy chain CDR (complementarity-determining region) amino acid sequences:

CDRH1 of SEQ ID NO 7, CDRH2 of SEQ ID NO 8 and CDRH3 of SEQ ID NO 9, 71 or 72; and (b) a light chain variable region including the following light chain CDR amino acid sequences:

CDRL1 of SEQ ID NO 10, CDRL2 of SEQ ID NO 11 and CDRL3 of SEQ ID NO 12, 73 or 74.

A third aspect of the present disclosure provides an antibody against HER2 (human epidermal growth factor receptor 2) including the following or an antigen-binding fragment thereof:

(a) a heavy chain variable region including the following heavy chain CDR (complementarity-determining region) amino acid sequences:

CDRH1 of SEQ ID NO 13, CDRH2 of SEQ ID NO 14 and CDRH3 of SEQ ID NO 15; and (b) a light chain variable region including the following light chain CDR amino acid sequences:

CDRL1 of SEQ ID NO 16, CDRL2 of SEQ ID NO 17 and CDRL3 of SEQ ID NO 18.

A fourth aspect of the present disclosure provides an antibody against HER2 (human epidermal growth factor receptor 2) including the following or an antigen-binding fragment thereof:

(a) a heavy chain variable region including the following heavy chain CDR (complementarity-determining region) amino acid sequences:

CDRH1 of SEQ ID NO 19, CDRH2 of SEQ ID NO 20 and CDRH3 of SEQ ID NO 21; and (b) a light chain variable region including the following light chain CDR amino acid sequences:

CDRL1 of SEQ ID NO 22, CDRL2 of SEQ ID NO 23 and CDRL3 of SEQ ID NO 24.

A fifth aspect of the present disclosure provides an antibody against HER2 (human epidermal growth factor receptor 2) including the following or an antigen-binding fragment thereof:

(a) a heavy chain variable region including the following heavy chain CDR (complementarity-determining region) amino acid sequences:

CDRH1 of SEQ ID NO 25, CDRH2 of SEQ ID NO 26 and CDRH3 of SEQ ID NO 27; and (b) a light chain variable region including the following light chain CDR amino acid sequences:

CDRL1 of SEQ ID NO 28, CDRL2 of SEQ ID NO 29 and CDRL3 of SEQ ID NO 30.

The antibody of the first aspect, the antibody of the second aspect, the antibody of the third aspect, the antibody of the fourth aspect and the antibody of the fifth aspect are referred to, respectively, as 2G10, 39D2, 24D3, 1G3 and 8G11 antibodies. They are mouse antibodies or chimeric antibodies. Among them, the humanized antibodies are expressed with the prefix hz, e.g., as hz2G10, hz39D2 and hz8G11 antibodies.

The inventors of the present disclosure have made efforts to develop a novel antibody which is capable of preventing or treating cancer (particularly, breast cancer and gastric cancer), exhibits better killing ability (or proliferation-inhibiting ability) for cancer cells which have non-reactivity (or resistance) to the trastuzumab antibody or have reduced sensitivity, and is capable of preventing or treating cancer with improved anticancer activity when co-administered with the trastuzumab antibody as compared to single administration of trastuzumab. As a result, they have developed a novel antibody which exhibits better killing ability for HER2-overexpressed cancer cells on which the trastuzumab antibody hardly acts, or exhibits improved anticancer activity when co-administered with the trastuzumab antibody, and have completed the present disclosure.

The antibody of the present disclosure or an antigen-binding fragment thereof has a specific binding ability for HER2. In particular, among the antibodies of the present disclosure, hz2G10 and hz39D2 bind to an epitope in domain 1 of domains 1-4 of HER2, 24D3 binds to an epitope in domain 3, and 1G3 and hz8G11 bind to an epitope in domain 4, like trastuzumab, which is different from the epitope to which trastuzumab binds.

In the present disclosure, the term "trastuzumab" refers to an antibody disclosed in U.S. Pat. No. 5,821,337.

The antibody of the present disclosure has superior killing ability or proliferation-inhibiting ability for cancer cells which have non-reactivity (or resistance) to the trastuzumab antibody or have reduced sensitivity, when used either alone or in combination with trastuzumab. In the present disclosure, the terms "killing", "proliferation-inhibiting" or "growth-inhibiting" are used interchangeable with the same meaning with regard to cancer cells.

In the present disclosure, the term "antibody" refers to an antibody specific for HER2, and includes not only the whole antibody but also an antigen-binding fragment of the antibody molecule.

A whole antibody has two full-length light chains and two full-length heavy chains. The light chains and heavy chains are connected by disulfide bonds. The constant region of the heavy chain has gamma ($\gamma$), mu ($\mu$), alpha ($\alpha$), delta ($\delta$) and epsilon ($\epsilon$) types, and has subclasses gamma1 ($\gamma$1), gamma2 ($\gamma$2), gamma3 ($\gamma$3), gamma4 ($\gamma$4), alpha1 ($\alpha$1) and alpha2 ($\alpha$2). The constant region of the light chain has kappa ($\kappa$) and lambda ($\lambda$) types.

In the present disclosure, the term "antigen-binding fragment" refers to a fragment having antigen-binding ability, and includes Fab, F(ab'), F(ab')$_2$, Fv, etc. Among the antibody fragments, Fab (fragment antigen-binding) has a structure having a variable region of the light and heavy chains, a constant region of the light chain and the first constant region (Cm) of the heavy chain and has one antigen-binding site. Fab' differs from Fab in that it has a hinge region including at least one cysteine residue at the C-terminus of the heavy chain CH1 domain. In the F(ab')$_2$ antibody, a cysteine residue in the hinge region of Fab' forms a disulfide bond. Recombinant techniques for generating Fv fragments with minimal antibody fragments in which Fv has only the heavy chain variable region and the light chain variable region are known in the related art. A double-chain variable fragment (dcFv) is linked to a heavy chain variable region and a light chain variable region via a non-covalent bond, and a single-chin variable fragment (scFv) is generally linked to covalently to the variable region of a heavy chain via a peptide linker, or to the C-terminus, to form a dimer such as the double-chain Fv. These antibody fragments can be obtained using proteases (for example, Fab can be obtained by cleaving a whole antibody with papain, and the F(ab')2 fragment can be obtained by cleaving with pepsin), or can be prepared using genetic recombination techniques.

Specifically, in the present disclosure, the antibody includes a monoclonal antibody, a multispecific antibody, a human antibody, a humanized antibody, a chimeric antibody, a single-chain Fv (scFv), a single-chain antibody, an Fab fragment, an F(ab') fragment, a disulfide-linked Fv (dsFv), an anti-idiotypic (anti-Id) antibody, and epitope-binding fragments of these antibodies, although not being limited thereto.

In the present disclosure, the term "heavy chain" encompasses a full-length heavy chain including a variable region domain $V_H$ and three constant region domains $C_{H1}$, $C_{H2}$ and $C_{H3}$, including an amino acid sequence having a variable region sequence sufficient for conferring specificity to an antigen, and fragments thereof. Also, in the present disclosure, the term "light chain" encompasses a full-length light chain including a variable region domain $V_L$ and a constant region domain $C_L$, including an amino acid sequence having a variable region sequence sufficient for conferring specificity to an antigen, and fragments thereof.

In the present disclosure, the term "variable region" or "variable domain" refers to a domain of an antibody heavy chain or light chain associated with binding of an antibody to an antigen. In general, the variable domains of a heavy chain and a light chain ($V_H$ and $V_L$, respectively) of a native antibody have similar structures, and each domain includes four conserved framework region (FRs) and three hypervariable regions (HVRs) (Kindt et al., Kuby Immunology, 6th ed., W.H. Freeman and Co., page 91 (2007)).

In the present disclosure, the term "CDR (complementarity-determining region)" refers to the amino acid sequence of the hypervariable region of a heavy chain and a light chain of an immunoglobulin (Kabat et al., Sequences of Proteins of Immunological Interest, 4th ed., U.S. Department of Health and Human Services, National Institutes of Health (1987)). Each of the heavy chain (CDRH1, CDRH2 and CDRH3) and the light chain (CDRL1, CDRL2 and CDRL3) includes three CDRs. The CDR provides major contact residue for binding of an antibody to an antigen or an epitope.

In the present disclosure, the term "framework region" or "FR" refers to a variable domain residue other than a hypervariable region (HVR) residue. The FR of a variable domain generally consists of four FR domains: FR1, FR2, FR3 and FR4. Accordingly, the HVR and FR sequences generally appear in the following order in $V_H$:

FRH1 (framework region 1 of heavy chain)-CDRH1 (complementarity-determining region 1 of heavy chain)-FRH2-CDRH2-FRH3-CDRH3-FRH4.

And, the HVR and FR sequences generally appear in the following order in $V_L$ (or $V_k$):

FRL1 (framework region 1 of light chain)-CDRL1 (complementarity-determining region 1 of light chain)-FRL2-CDRL2-FRL3-CDRL3-FRL4.

In the present disclosure, the term "specific binding" means that an antibody or an antigen-binding fragment thereof, or another construct such as scFv forms a relatively stable complex with an antigen under physiological conditions. The specific binding may be characterized by an equilibrium dissociation constant of about $1 \times 10^{-6}$ M or smaller (e.g., the smaller the $K_d$, the tighter the binding). Methods for determining if two molecules bind specifically are well known in the art, for example, equilibrium dialysis, surface plasmon resonance, etc.

In the present disclosure, the term "affinity" refers to the strength of the sum of noncovalent interactions between a single binding site of a molecule (e.g., an antibody) and its binding partner (e.g., an antigen). Unless specified otherwise, "binding affinity" refers to intrinsic binding affinity which reflects a 1:1 interaction between the members of a binding pair (e.g., an antibody and an antigen). The affinity of a molecule X for its partner Y may generally be represented by a dissociation constant ($K_d$). The affinity can be measured by common methods known in the art, including those described in the present disclosure.

In the present disclosure, the "human antibody" or "humanized antibody" possesses an amino acid sequence which corresponds to an antibody produced by human or a human cell, or an antibody derived from a non-human source that utilizes human antibody repertoires or other human antibody-encoding sequences.

In the present disclosure, the term "chimeric antibody" refers to an antibody in which a portion of the heavy chain and/or light chain is derived from a particular source or species while the remainder of the heavy chain and/or light chain is derived from a different source or species.

The anti-HER2 antibody of the present disclosure or an antigen-binding fragment thereof may include variants of the amino acid sequences described in the attached sequence listings within the scope of specifically recognizing HER2. For example, the amino acid sequence of an antibody may be modified to improve the binding affinity and/or other biological properties of the antibody. Such modification includes, for example, deletion, insertion and/or substitution of the amino acid sequence residue of the antibody.

Such amino acid variation is made based on the relative similarity of amino acid side chain substituents, such as hydrophobicity, hydrophilicity, charge, size, etc. From analysis of the size, shape and type of amino acid side chain substituents, it is recognized that arginine, lysine and histidine are positively charged residues; alanine, glycine and serine have similar sizes; and phenylalanine, tryptophan and tyrosine have similar shapes. Based on these considerations, it is thus recognized that arginine, lysine and histidine; alanine, glycine and serine; and phenylalanine, tryptophan and tyrosine are biologically functional equivalents.

For introduction of mutation, the hydropathy indices of amino acids may be considered. Each amino acid is assigned a hydropathy index according to its hydrophobicity and charge: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The hydropathy indices of amino acids are very important in imparting the interactive biological function of proteins. It is well known that similar biological activity can be retained when substitution is made with an amino acid having a similar hydropathy index. In this regard, when mutation is introduced, substitution is made between amino acids showing difference in the hydropathy index preferably within ±2, more preferably within ±1, even more preferably within ±0.5.

Meanwhile, it is also well known that substitution between amino acids having similar hydrophilicity values leads to proteins with equivalent biological activity. As disclosed in U.S. Pat. No. 4,554,101, the following hydrophilicity values are assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In this regard, when mutation is introduced, substitution is made between amino acids showing difference in the hydrophilicity value preferably within ±2, more preferably within ±1, even more preferably within ±0.5.

Amino acid substitutions in proteins that do not entirely alter the activity of the molecules are known in the art (H.

Neurath, R. L. Hill, The Proteins, Academic Press, New York, 1979). The most commonly occurring substitutions are substitutions between the following amino acid residues: Ala/Ser, Val/Ile, Asp/Glu, Thr/Ser, Ala/Gly, Ala/Thr, Ser/Asn, Ala/Val, Ser/Gly, Thy/Phe, Ala/Pro, Lys/Arg, Asp/Asn, Leu/Ile, Leu/Val, Ala/Glu and Asp/Gly.

In an exemplary embodiment of the present disclosure, the heavy chain variable region of the hz2G10 antibody and the 2G10 antibody respectively includes amino acid sequences of SEQ ID NO 31 and 32.

In an exemplary embodiment of the present disclosure, the light chain variable region of the hz2G10 antibody and the 2G10 antibody respectively includes amino acid sequences of SEQ ID NO 35 and 77.

In an exemplary embodiment of the present disclosure, the heavy chain variable region of the hz39D2 antibody and the 39D2 antibody respectively includes amino acid sequences of SEQ ID NO 39 and 83.

In an exemplary embodiment of the present disclosure, the light chain variable region of the hz39D2 antibody and the 39D2 antibody respectively includes amino acid sequences of SEQ ID NO 43 and 85.

In an exemplary embodiment of the present disclosure, the heavy chain variable region of the 24D3 antibody includes an amino acid sequence of SEQ ID NO 47.

In an exemplary embodiment of the present disclosure, the light chain variable region of the 24D3 antibody includes an amino acid sequence of SEQ ID NO 51.

In an exemplary embodiment of the present disclosure, the heavy chain variable region of the 1G3 antibody includes an amino acid sequence of SEQ ID NO 55.

In an exemplary embodiment of the present disclosure, the light chain variable region of the 1G3 antibody includes an amino acid sequence of SEQ ID NO 59.

In an exemplary embodiment of the present disclosure, the heavy chain variable region of the hz8G11 antibody and the 8G11 antibody respectively includes amino acid sequences of SEQ ID NO 63 and 79.

In an exemplary embodiment of the present disclosure, the light chain variable region of the hz8G11 antibody and the 8G11 antibody respectively includes amino acid sequences of SEQ ID NO 67 and 81.

The antibody of the present disclosure includes a monoclonal antibody, a multispecific antibody, a human antibody, a humanized antibody, a chimeric antibody, a single-chain Fv (scFv), a single-chain antibody, an Fab fragment, an F(ab') fragment, a disulfide-linked Fv (dsFv), an anti-idiotypic (anti-Id) antibody, and epitope-binding fragments of these antibodies, although not being limited thereto.

Meanwhile, the antibody of the present disclosure is unique in that its CDR sequence has very low homology (similarity) to the CDR sequences of existing anti-HER2 antibodies. For example, as a result of BLAST search for hz2G10 from among the antibodies of the present disclosure, the highest CDR sequence homology of the antibody of the present disclosure to the antibodies disclosed in U.S. Pat. Nos. 8,314,213 and 8,404,811 was less than 50%. In addition, the antibodies disclosed in U.S. Pat. Nos. 8,314,213 and 8,404,811 bind to CD25 and EGFL7, respectively, and are different from the antibody of the present disclosure in their targets.

In addition, the anti-HER2 antibody of the present disclosure or an antigen-binding fragment thereof encompasses an anti-HER2 antibody including a slight change in the amino acid sequence described above, including the modification that hardly affects the tertiary structure and function of the antibody, or an antigen-binding fragment thereof.

Accordingly, in some exemplary embodiments, the antibody may have an amino acid sequence with at least 90%, 93%, 95% or 98% similarity to the above-described sequence.

Also, in the present disclosure, the heavy chain variable region and the light chain variable region of the antibody or an antigen-binding fragment thereof may be linked by a linker composed of an amino acid sequence represented by the general formula $(G_nS_m)_p$ or $(S_mG_m)_p$.

In the formula, n, m and p satisfy the followings:
n is an integer from 1 to 7;
m is an integer from 0 to 7;
n+m is an integer which is 8 or smaller; and
p is an integer from 1 to 7.

In a specific exemplary embodiment of the present disclosure, n=1-5 and m=0-5. In a more specific exemplary embodiment, n=4 and m=1. In a further more specific exemplary embodiment, the linker is $(G_4S)_3$ or $(S_4G)_3$.

In another exemplary embodiment, the linker is VDGS. In another exemplary embodiment, the linker is ASGS.

In addition, the light chain variable region and the heavy chain variable region of the antibody according to the present disclosure or an antigen-binding fragment may in the following orientations:
light chain variable region-linker-heavy chain variable region; or
heavy chain variable region-linker-light chain variable region.

Another aspect of the present disclosure provides a fusion protein including an anti-HER2 antibody or an antigen-binding fragment thereof.

In the present disclosure, the fusion protein is prepared for the productivity purification efficiency, improved biological activity, increased stability, improved folding and/or binding to a functional moiety for additional function of the anti-HER2 antibody of the present disclosure or an antigen-binding fragment thereof. The fusion protein may be formed as two or more polypeptide chains are linked by a covalent bond, or may be in the form of a conjugate wherein two or more polypeptide chains are linked by chemical conjugation.

Another aspect of the present disclosure provides a chimeric antigen receptor polypeptide including the followings:
(a) an HER2-binding domain;
(b) a transmembrane domain (TM);
(c) a costimulatory domain (domain); and
(d) an intracellular signaling domain (ICD).

In the present disclosure, the term "chimeric antigen receptor (CAR)" refers to an artificially constructed hybrid protein (fusion protein) or polypeptide containing a target-binding domain (e.g. single-chain variable fragment (scFv)) linked to an effector cell-signaling or effector cell-activating domain (e.g. T-cell signaling or T-cell activating domain). In general, the chimeric antigen receptor has the ability of redirecting T-cell specificity and reactivity toward a selected target in a non-MHC restricted manner by taking advantage of the antigen-binding property of a monoclonal antibody. The non-MHC-restricted antigen recognition confers the ability to recognize an antigen on T-cells expressing CAR, thus bypassing the major mechanism of tumor escape. Moreover, when expressed in T-cells, the CAR advantageously does not dimerize with the endogenous T-cell receptor (TCR) alpha and beta chains.

In an exemplary embodiment of the present disclosure, the chimeric antigen receptor of the present disclosure recognizes the HER2 antigen and is expressed on the cell surface since it includes the HER2-binding domain including the anti-HER2 antibody of the present disclosure or an antigen-binding fragment thereof.

The chimeric antigen receptor of the present disclosure includes a transmembrane domain because it is expressed on the cell surface. The transmembrane domain may be a transmembrane domain of a protein selected from a group consisting of the T-cell receptor alpha, beta or zeta chain, CD28, CD3 epsilon, CD45, CD4, CD5, CD8, CD9, CD16, CD22, CD33, CD37, CD64, CD80, CD86, CD134, CD137 and CD154, although not being limited thereto.

In a specific exemplary embodiment of the present disclosure, the transmembrane domain may be a transmembrane domain of CD8 or CD28.

The costimulatory domain of the chimeric antigen receptor of the present disclosure may be a functional signaling domain obtained from a protein selected from a group consisting of MHC class I molecule, TNF receptor protein, immunoglobulin-like protein, cytokine receptor, integrin, signaling lymphocytic activation molecule (SLAM), activating NK cell receptor, BTLA (B- and T-lymphocyte attenuator), Toll-like ligand receptor, OX40, CD2, CD7, CD27, CD28, CD30, CD40, CDS, ICAM-1, LFA-1 (CD11a/CD18), 4-1BB (CD137), B7-H3, CDS, ICAM-1, ICOS (CD278), GITR, BAFFR, LIGHT, HVEM (LIGHTR), KIRDS2, SLAMF7, NKp80 (KLRF1), NKp44, NKp30, NKp46, CD19, CD4, CD8alpha, CD8 beta, IL2R beta, IL2R gamma, IL7R alpha, ITGA4, VLA1, CD49a, ITGA4, IA4, CD49D, ITGA6, VLA-6, CD49f, ITGAD, CD11d, ITGAE, CD103, ITGAL, CD11a, LFA-1, ITGAM, CD11b, ITGAX, CD11c, ITGB1, CD29, ITGB2, CD18, LFA-1, ITGB7, NKG2D, NKG2C, TNFR2, TRANCE/RANKL, DNAM1 (CD226), SLAMF4 (CD244, 2B4), CD84, CD96 (Tactile), CEACAM1, CRTAM, Ly9 (CD229), CD160 (BY55), PSGL1, CD100 (SEMA4D), CD69, SLAMF6 (NTB-A, Ly108), SLAM (SLAMF1, CD150, IPO-3), BLAME (SLAMF8), SELPLG (CD162), LTBR, LAT, GADS, SLP-76, PAG/Cbp, CD19a, and a ligand binding specifically to CD83, although not being limited thereto.

In a specific exemplary embodiment of the present disclosure, the costimulatory domain may be a functional signaling domain obtained from a protein selected from a group consisting of CD28, OX40, 4-1BB (CD137) and/or ICOS (CD278), more specifically a functional signaling domain of CD28 and/or OX40.

In another exemplary embodiment of the present disclosure, the intracellular signaling domain is a functional signaling domain of 4-1BB, CD28, OX40 or CD3 zeta, or a combination thereof. Most specifically, the intracellular signaling domain is a functional signaling domain of CD3 zeta.

In another embodiment of the present disclosure, the intracellular signaling domain may be a functional signaling domain of OX40 ligand (OX40L), In another embodiment, the intracellular signaling domain is OX40 ligand.

The HER2-binding domain of the chimeric antigen receptor of the present disclosure is linked to the transmembrane domain by a hinge domain.

In another exemplary embodiment of the present disclosure, the hinge domain may be IgG4 hinge, CD8 hinge or IgD hinge.

Another aspect of the present disclosure provides a nucleic acid molecule encoding the anti-HER2 antibody or an antigen-binding fragment thereof, or the chimeric antigen receptor polypeptide described above.

In the present disclosure, the term "nucleic acid molecule" encompasses DNA (gDNA and cDNA) and RNA molecules, and the nucleotides that are the basic building blocks of the nucleic acid molecule include not only natural nucleotides but also analogues having modified sugar or base moieties (Scheit, *Nucleotide Analogs*, John Wiley, New York (1980); Uhlman and Peyman, *Chemical Reviews*, 90: 543-584 (1990)).

A nucleotide sequence encoding the antibody of the present disclosure or an antigen-binding fragment thereof, or the chimeric antigen receptor polypeptide is not limited to a specific nucleotide sequence as long as it is a nucleotide sequence encoding the amino acid sequences constituting the chimeric antigen receptor molecule.

This is because the variation in nucleotide sequences may not lead to change in protein sequences through expression. This is called codon degeneracy. Accordingly, the nucleotide sequence includes a nucleotide sequence including functionally equivalent codons, or codons encoding the same amino acid (for example, six codons encode arginine or serine due to codon degeneracy) or codons encoding a biologically equivalent amino acid.

In a specific exemplary embodiment of the present disclosure, the nucleotide sequence encoding the polypeptide constituting the heavy chain CDR, light chain CDR, heavy chain variable region, light chain variable region, heavy chain or light chain of the anti-HER2 antibody of the present disclosure or an antigen-binding fragment thereof is described in the attached sequence listings.

The nucleic acid molecule of the present disclosure, which encodes the anti-HER2 antibody or an antigen-binding fragment thereof, or the chimeric antigen receptor polypeptide, is understood to encompass a nucleotide sequence exhibiting substantial identity for the nucleotide sequence. The substantial identity means that, when the nucleotide sequence of the present disclosure is aligned to another sequence correspond to each other as much as possible and the aligned sequences are analyzed using an algorithm commonly used in the art, the nucleotide sequences exhibit at least 80% homology, more specifically at least 90% homology, most specifically at least 95% homology.

When considering the variation of biologically equivalent activity, it is understood that the nucleic acid molecule encoding the antibody of the present disclosure or an antigen-binding fragment; or the chimeric antigen receptor polypeptide encompasses a sequence exhibiting substantial identity to the sequences described in the sequence listings. The substantial identity means that, when the sequence of the present disclosure and another sequence are aligned to correspond to each other as much as possible and the aligned sequences are analyzed using an algorithm commonly used in the art, the sequences have at least 61% homology, more specifically 70% homology, further more specifically 80% homology, most specifically 90% homology. Methods of the alignment for sequence comparison are known in the art. Various methods and algorithms for the alignment are disclosed in Smith and Waterman, *Adv. Appl. Math.* 2: 482 (1981); *Needleman and Wunsch, J. Mol. Bio.* 48: 443 (1970); Pearson and Lipman, *Methods in Mol. Biol.* 24: 307-31 (1988); Higgins and Sharp, *Gene* 73: 237-44 (1988); Higgins and Sharp, *CABIOS* 5: 151-3 (1989); Corpet et al., *Nuc. Acids Res.* 16: 10881-90 (1988); Huang et al., *Comp. Appl. BioSci.* 8: 155-65 (1992) and Pearson et al., *Meth. Mol. Biol.* 24: 307-31 (1994). The NCBI's basic local alignment search tool (BLAST) (Altschul et al., *J. Mol. Biol.* 215: 403-10 (1990)) is accessible from the NBCI (National Center for Biotechnology Information) and on the Internet and may be used in connection with sequence analysis programs such as blastp, blastn, blastx, tblastn and tblastx. BLAST may be accessed through the BLAST webpage of the NCBI's website. The method for comparing sequence homology using such a program is available from the BLAST help page of the NCBI's website.

In connection with the claims of the application/patent, sequence identity is determined according to the Needleman and Wunsch algorithm.

Another aspect of the present disclosure provides a recombinant vector including the nucleic acid molecule.

In the present disclosure, the term "vector" includes a delivery vector and an expression vector.

In the present disclosure, the term "delivery vector" refers to a composition of a material which contains an isolated nucleic acid and can be used to deliver the isolated nucleic acid into a cell. It includes a linear polynucleotide, a polynucleotide associated with an ionic or amphiphilic compound, a plasmid and a virus, although not being limited thereto. More specifically, the delivery vector includes a self-replicating plasmid or virus. The term is also construed to include non-plasmid and non-viral compounds which facilitate transfer of nucleic acids into cells, such as, for example, polylysine compounds, liposomes, etc. Examples of the viral delivery vector include an adenoviral vector, an adeno-associated viral vector, a retroviral vector and a lentiviral vector, although not being limited thereto.

In the present disclosure, the term "expression vector" refers to a vector including a recombinant nucleotide including an expression control sequence operably linked to a nucleotide sequence to be expressed for expression of a target gene in a host cell. The expression vector includes a cis-acting element sufficient for expression and other elements for expression can be provided by a host cell or an in-vitro expression system. The expression vector includes a plasmid vector including a recombinant polynucleotide; a cosmid vector; and a viral vector such as a bacteriophage vector, an adenoviral vector, a lentiviral vector, a retroviral vector and an adeno-associated viral vector. In a specific exemplary embodiment of the present disclosure, a nucleic acid molecule encoding a switch molecule is operatively linked to a promoter of the vector of the present disclosure. In the present disclosure, the term "operatively linked" refers to functional linkage between a nucleic acid expression control sequence (e.g., a promoter, a signal sequence, or an array of a transcription factor binding site) and another nucleic acid sequence, wherein the control sequence affects the transcription and/or translation of the another nucleic acid sequence.

The recombinant vector system of the present disclosure may be constructed according to various methods known in the art. Specific methods are described in Sambrook et al., Molecular Cloning, A Laboratory Manual, Cold Spring Harbor Laboratory Press (2001), which is incorporated into the present disclosure by reference.

The vector of the present disclosure may be constructed as a vector for gene cloning, a vector for protein expression, or a vector for gene delivery. In addition, the vector of the present disclosure may be constructed by using a prokaryotic cell or a eukaryotic cell as a host cell.

For example, when the vector of the present disclosure is an expression vector and a eukaryotic cell is used as a host cell, a promoter derived from the genome of a mammalian cell (e.g., metallothionein promoter, β-actin promoter, human hemoglobin promoter and human muscle creatine promoter) or a promoter derived from a mammalian virus (e.g., adenovirus late promoter, vaccinia virus 7.5K promoter, SV40 promoter, cytomegalovirus promoter, tk promoter of HSV, mouse mammary tumor virus (MMTV) promoter, LTR promoter of HIV, Moloney virus promoter, Epstein-Barr virus (EBV) promoter and Rous sarcoma virus (RSV) promoter) may be used, and they generally have a polyadenylation sequence as a transcription termination sequence.

In an exemplary embodiment of the present disclosure, when the vector is a delivery vector, it may be a "retroviral vector". Retrovirus provides a convenient platform for a gene delivery system. A gene selected for gene delivery may be inserted in the retroviral vector and may be packaged within a retroviral particle. Then, the recombinant retrovirus may be delivered to a target host cell in vivo or in vitro. Many retroviral vectors are known in the art. In a specific exemplary embodiment of the present disclosure, the retroviral vector may be a pMT retroviral vector which is an MLV-based retroviral vector, although not being limited thereto.

In another exemplary embodiment of the present disclosure, the vector is a lentiviral vector or an adenoviral vector.

The vector of the present disclosure may be fused with other sequences for easy purification of the polypeptide or protein expressed thereby. For example, the fused sequence may be glutathione S-transferase (Pharmacia, USA), maltose-binding protein (NEB, USA), FLAG (IBI, USA), 6× His (hexahistidine; Quiagen, USA), etc. Meanwhile, the expression vector of the present disclosure may include a selectable marker gene and/or a reporter gene for evaluating the expression of the antibody of the present disclosure or an antigen-binding fragment thereof, or a CAR polypeptide including the same. The selectable marker gene includes an antibiotic-resistant gene commonly used in the art, e.g., genes resistant to ampicillin, gentamicin, carbenicillin, chloramphenicol, streptomycin, kanamycin, geneticin, neomycin and tetracycline. The reporter gene includes luciferase, beta-galactosidase, chloramphenicol, acetyltransferase or green fluorescent protein gene.

Methods for introducing the recombinant vector of the present disclosure into a cell and expressing the same are well known in the related art. The vector may be easily introduced into a host cell, e.g., a mammalian cell, a bacterial cell, a yeast cell or an insect cell according to methods known in the art. For example, the vector may be delivered into a host cell by physical, chemical or biological means. The physical means includes calcium phosphate coprecipitation, lipofection, particle bombardment, microinjection, electroporation, etc. The chemical means includes a colloidal dispersion system, e.g., a macromolecular complex, a nanocapsule, a microsphere, a bead, and a lipid-based system including an oil-in-water emulsion, a micelle, a mixed micelle and a liposome. And, the biological means includes use of a DNA or RNA vector such as a lentiviral vector, a retroviral vector, etc. as described above.

Another aspect of the present disclosure provides a host cell transformed with the recombinant vector.

The host cell capable of cloning and expressing the vector of the present disclosure stably and continuously may be any host cell known in the art. For example, a eukaryotic host cell suitable for the vector includes a monkey kidney cell 7 (COST), an NSO cell, an SP2/0 cell, a Chinese hamster ovary (CHO) cell, a W138 cell, a baby hamster kidney (BHK) cell, a MDCK cell, a myeloma cell, a HuT 78 cell and an HEK-293 cell, although not being limited thereto.

Another aspect of the present disclosure provides an effector cell expressing the chimeric antigen receptor (CAR) polypeptide.

In an exemplary embodiment of the present disclosure, the effector cell is selected from a group consisting of a dendritic cell, a killer dendritic cell, a mast cell, a natural killer cell, a B lymphocyte, a T lymphocyte, a macrophage and precursor cells thereof, although not being limited thereto. The T lymphocyte cell is selected from a group consisting of an inflammatory T lymphocyte, a cytotoxic T lymphocyte, a regulatory T lymphocyte or a helper T lymphocyte.

In the present disclosure, the effector cell includes a group of autologous cells or allogenic cells. That is to say, the effector cell includes a group of autologous cells or allogenic cells expressing the HER2-specific CAR polypeptide.

In another exemplary embodiment of the present disclosure, the effector cell includes a group of cells transfected or transduced with a vector including a nucleic acid molecule encoding the HER2-specific CAR polypeptide. The transfection or transduction may be achieved by various means known in the art without limitation.

Accordingly, in a specific exemplary embodiment of the present disclosure the present disclosure, the HER2-specific CAR-encoding nucleic acid molecule is delivered into an effector cell, e.g., a T lymphocyte or a natural killer cell, and transcribed into mRNA. The HER2-specific CAR polypeptide is translated from the mRNA and expressed on the surface of the effector cell.

Another aspect of the present disclosure provides a pharmaceutical composition for preventing or treating cancer, which contains: (a) a pharmaceutically effective amount of the anti-HER2 antibody of the present disclosure or the antigen-binding fragment thereof described above; and (b) a pharmaceutically acceptable carrier.

Another aspect of the present disclosure provides a pharmaceutical composition for treating cancer or an inflammatory disease, which contains an effector cell expressing the chimeric antigen receptor polypeptide described above.

The pharmaceutical composition is a pharmaceutical composition for immunotherapy, which contains an effector cell expressing the anti-HER2 antibody or an antigen-binding fragment thereof; or the chimeric antigen receptor polypeptide.

In the present disclosure, "immunotherapy" refers to treatment of cancer by activating the immune system. Immunotherapy is classified into active immunotherapy and passive immunotherapy. Active immunotherapy includes i) cancer vaccine therapy of activating the immune system by injecting cancer cells or substances produced by cancer cells into human body, and ii) immunomodulatory therapy of activating specific leukocytes by administering immunomodulatory agents such as cytokines (interferons, interleukins, etc.), growth factors, etc. Passive immunotherapy includes antibody therapy and immune cell therapy. Specifically, immune cell therapy includes dendritic cell vaccine therapy, chimeric antigen receptor T (CAR-T) cell therapy, natural killer (NK) cell therapy, cytotoxic T lymphocyte (CTL) therapy, adoptive cell transfer, etc., although not being limited thereto. In the present disclosure, the immunotherapy mainly refers to antibody therapy using the anti-HER2 antibody and immune cell therapy using the HER2-specific CAR.

The pharmaceutical composition of the present disclosure contains an effector cell expressing the anti-HER2 antibody of the present disclosure or an antigen-binding fragment thereof; the chimeric antigen receptor polypeptide; or the chimeric antigen receptor as an active ingredient. Therefore, description of the details described above will be omitted to avoid redundancy.

As demonstrated in the following examples, the anti-HER2 antibody of the present disclosure exhibits better killing ability for MCF-7 cells on which the trastuzumab antibody hardly acts. In addition, the anti-HER2 antibody of the present disclosure exhibits improved killing ability for SKBR3 breast cancer cells when co-administered with trastuzumab. Accordingly, the composition of the present disclosure is very effective for combined administration with the trastuzumab antibody for treatment of cancer and for treatment of cancer not treated with trastuzumab.

The cancer that can be prevented or treated by the composition of the present disclosure includes various cancers known in the art. For example, it includes breast cancer, ovarian cancer, gastric cancer, lung cancer, liver cancer, bile duct cancer, bronchial cancer, nasopharyngeal cancer, laryngeal cancer, pancreatic cancer, bladder cancer, kidney cancer, colorectal cancer, colon cancer, cervical cancer, brain cancer, prostate cancer, bone cancer, head and neck cancer, skin cancer, thyroid cancer, parathyroid cancer or ureteral cancer.

Specifically, the cancer that can be prevented or treated by the composition of the present disclosure is HER2-expressing cancer, more specifically HER2-expressing breast cancer or gastric cancer.

The pharmaceutically acceptable carrier contained in the pharmaceutical composition of the present disclosure is one commonly used in preparation, and includes lactose, dextrose, sucrose, sorbitol, mannitol, starch, acacia gum, calcium phosphate, alginate, gelatin, calcium silicate, microcrystalline cellulose, polyvinylpyrrolidone, cellulose, water, syrup, methyl cellulose, methyl hydroxybenzoate, propyl hydroxybenzoate, talc, magnesium stearate, mineral oil, etc., although not being limited thereto. The pharmaceutical composition of the present disclosure may further contain a lubricant, a wetting agent, a sweetener, a flavor, an emulsifier, a suspending agent, a preservative, etc. in addition to the above-described ingredients. Suitable pharmaceutically acceptable carriers and preparations are described in detail in Remington's Pharmaceutical Sciences (19th ed., 1995).

The pharmaceutical composition of the present disclosure may be administered orally or parenterally. For example, it may be administered intravenously, subcutaneously, intramuscularly, intraperitoneally, topically, intranasally, intrapulmonarily, intrathecally, ocularly, intradermally, transdermally, etc.

An administration dosage of the pharmaceutical composition of the present disclosure varies depending on such factors as formulation method, administration method, the age, body weight, sex of a patient, pathological condition, food, administration time, administration route, excretion rate and responsiveness. A normally trained physician can easily determine and prescribe an administration dosage for effective treatment or prevention. In a specific exemplary embodiment of the present disclosure, a daily administration dosage of the pharmaceutical composition of the present disclosure is 0.0001-100 mg/kg. In the present disclosure, the term "pharmaceutically effective amount" refers to an amount sufficient for preventing or treating cancer.

The pharmaceutical composition of the present disclosure may be formulated into a unit-dosage form or a multiple-dosage form using a pharmaceutically acceptable carrier and/or excipient according to a method that can be easily employed by those of ordinary skill in the art to which the present disclosure belongs. The formulation may be in the form of a solution in an oily or aqueous medium, a suspension, an emulsion, an extract, a pulvis, a suppository, a powder, a granule, a tablet or a capsule, and may further contain a dispersant or a stabilizer.

In an exemplary embodiment of the present disclosure, the pharmaceutical composition of the present disclosure may further contain the trastuzumab antibody.

The pharmaceutical composition of the present disclosure may further contain, in addition to the active ingredient derived above, another pharmaceutically active medication or drug, e.g., a chemotherapy agent such as asparaginase, busulfan, carboplatin, cisplatin, daunorubicin, doxorubicin, fluorouracil, gemcitabine, hydroxyurea, methotrexate, paclitaxel, rituximab, vinblastine, vincristine, etc., a targeted therapy agent such bevacizumab, olaparib, etc., or an immune checkpoint inhibitor such as nivolumab or pembrolizumab, or may be co-administered with them.

Another aspect of the present disclosure provides a method for treating cancer, which includes a step of administering a composition containing an effector cell expressing the anti-HER2 antibody or an antigen-binding fragment thereof; or the HER2-specific chimeric antigen receptor to a subject in need of treatment.

The cancer to be treated by the therapeutic method of the present disclosure is the same as defined above with regard to the pharmaceutical composition.

In an exemplary embodiment of the present disclosure, the subject may be a mammal or human.

Since the method for treating cancer or an inflammatory disease of the present disclosure uses an effector cell expressing the antibody or an antigen-binding fragment; or the chimeric antigen receptor described above as an active ingredient, description of the details described above will be omitted to avoid redundancy.

The anti-HER2 antibody or an antigen-binding fragment thereof described above may be used for diagnosis, e.g., diagnosis of cancer.

Accordingly, another aspect of the present disclosure provides a kit for diagnosing cancer, which includes the anti-HER2 antibody of the present disclosure or an antigen-binding fragment thereof.

Since the diagnostic kit of the present disclosure includes the anti-HER2 antibody of the present disclosure or an antigen-binding fragment thereof described above and diagnoses the same disease as described above with regard to the pharmaceutical composition of the present disclosure, description of the details described above will be omitted to avoid redundancy.

Since the kit includes an antibody, it can be prepared to be suitable for various immunoassay or immunostaining applications. The immunoassay or immunostaining includes radioimmunoassay, radioimmunoprecipitation, immunoprecipitation, enzyme-linked immunosorbent assay (ELISA), capture ELISA, inhibition or competition assay, sandwich assay, flow cytometry, immunofluorescence staining and immunoaffinity purification, although not being limited thereto. Methods for the immunoassay or immunostaining are described in Enzyme Immunoassay, E. T. Maggio, ed., CRC Press, Boca Raton, Fla., 1980; Gaastra, W., Enzyme-linked immunosorbent assay (ELISA), in Methods in Molecular Biology, Vol. 1, Walker, J. M. ed., Humana Press, N J, 1984; and Ed Harlow and David Lane, Using Antibodies: A Laboratory Manual, Cold Spring Harbor Laboratory Press, 1999, which are incorporated in the present disclosure by reference.

For example, when the method of the present disclosure is carried out by radioimmunoassay, an antibody labeled with a radioisotope (e.g., $C^{14}$, $I^{125}$, $P^{32}$ or $S^{35}$) may be used to detect the HER2 protein. When the method of the present disclosure is carried out by ELISA, a specific exemplary embodiment of the present disclosure includes: (i) a step of coating a sample to be analyzed on the surface of a solid substrate; (ii) a step of reacting the sample with the anti-HER2 antibody of the present disclosure as a primary antibody; (iii) a step of reacting the resultant of the step (ii) with a secondary antibody coupled with an enzyme; and (iv) a step of measuring the activity of the enzyme.

Appropriate examples of the solid substrate are a hydrocarbon polymer (e.g., polystyrene or polypropylene), glass, a metal or a gel, most specifically, a microtiter plate.

The enzyme coupled with the secondary antibody may include an enzyme that catalyzes chromogenic reaction, fluorescence reaction, luminescent reaction or infrared reaction, although not being limited thereto. For example, it includes alkaline phosphatase, β-galactosidase, horseradish peroxidase, luciferase and cytochrome P450. When alkaline phosphatase is used as the enzyme coupled with the secondary antibody, a chromogenic substrate such as bromochloroindolyl phosphate (BCIP), nitro blue tetrazolium (NBT), naphthol-AS-B1-phosphate and enhanced chemifluorescence (ECF) may be used as the substrate. When horseradish peroxidase is used, a substrate such as chloronaphthol, aminoethylcarbazole, diaminobenzidine, D-luciferin, lucigenin (bis-N-methylacridinium nitrate), resorufin benzyl ether, luminol, Amplex Red (10-acetyl-3,7-dihydroxyphenoxazine), HYR (p-phenylenediamine-HCl and pyrocatechol), tetramethylbenzidine (TMB), 2,2-azino-di[3-ethylbenzthiazoline sulfonate] (ABTS), o-phenylenediamine (OPD), naphthol/pyronin, glucose oxidase, t-NBT (nitro blue tetrazolium) and m-PMS (phenzaine methosulfate) may be used.

When the method of the present disclosure is carried out by capture ELISA, the method includes: (i) a step of coating the HER2 antibody as a capture antibody on the surface of a solid substrate; (ii) a step of reacting the capture antibody with a sample; (iii) a step of reacting the resultant of the step (ii) with an HER2 detection antibody conjugated with a label; and (iv) a step of measuring a signal generated from the label.

The anti-HER2 antibody of the present disclosure has a label that generates a signal that can be detected by the detection antibody. The label includes a chemical substance (e.g., biotin), an enzyme (alkaline phosphatase, (β-galactosidase, horseradish peroxidase or cytochrome P450), a radioactive substance (e.g., $C^{14}$, $I^{125}$, $P^{32}$ and $S^{35}$) a fluorescent material (e.g., fluorescein), a light-emitting material, a chemiluminescent material and a FRET (fluorescence resonance energy transfer) material, although not being limited thereto. Various labels and labeling method are described in Ed Harlow and David Lane, Using Antibodies: A Laboratory Manual, Cold Spring Harbor Laboratory Press, 1999.

In the ELISA method and the capture ELISA, the measurement of the enzyme activity or the measurement of the signal may be carried out according to various methods known in the art. The signal may be detected easily by using streptavidin when biotin is used as the label, and using luciferin when luciferase is used.

The sample to which the kit of the present disclosure can be applied includes a cell, a tissue, a tissue-derived extract, a lysate, a purification product, a blood, a plasma, a serum, a lymph or ascites, although not being limited thereto.

The antibody of the present disclosure may be used in in-vivo or in-vitro imaging. Another aspect of the present disclosure provides a composition for imaging, which contains a conjugate in which the antibody of the present disclosure is conjugated to a label generating a detectable signal.

The label generating a detectable signal includes a T1 contrast agent (e.g., a Gd chelate compound), a T2 contrast agent (e.g., a superparamagnetic material (e.g., magnetite, Fe$_3$O$_4$, γ-Fe$_2$O$_3$, manganese ferrite, cobalt ferrite and nickel ferrite)), a radioiosotope (e.g., $^{11}$C, $^{15}$O, $^{13}$N, P$^{32}$, S$^{35}$, $^{44}$Sc, $^{45}$Ti, $^{118}$I, $^{136}$La, $^{198}$Tl, $^{200}$Tl, $^{205}$Bi and $^{206}$Bi), a fluorescent material (fluorescein, phycoerythrin, rhodamine, lissamine, Cy3 and Cy5), a chemiluminescent material, a magnetic particle, a mass label or an electron-dense particle, although not being limited thereto.

Advantageous Effects

The features and advantages of the present disclosure may be summarized as follows:

(a) The antibody of the present disclosure or an antigen-binding fragment is an antibody that specifically binds to HER2 which is highly expressed in cancer cells (particularly, breast cancer or gastric cancer cells), and binds to an epitope that is different from an epitope to which trastuzumab binds. The present disclosure provides the antibody or the antigen-binding fragment, a chimeric antigen receptor including the same, and uses thereof.

(b) The antibody of the present disclosure or an antigen-binding fragment is unique in that its CDR sequence has very low homology to the CDR sequences of existing HER2-targeting antibodies.

(c) When compared with trastuzumab, the antibody of the present disclosure exhibits better killing ability for HER2-unexpressed cancer cells which have non-reactivity (or resistance) to the trastuzumab antibody or have reduced sensitivity. In addition, when the anti-HER2 antibody of the present disclosure is administered in combination with trastuzumab, a synergistic killing ability is achieved for cancer cells on which the trastuzumab antibody acts. Therefore, a composition of the present disclosure can be used for combined administration with the trastuzumab antibody for the treatment of cancer, or for the treatment of cancer not treated with trastuzumab. In particular, when expressed in effector cells such as T lymphocytes, etc., the chimeric antigen receptor including the anti-HER2 antibody of the present disclosure or an antigen-binding fragment may be used for immune cell therapy of various HER2-related cancers.

(d) Without wishing to be bound by theory, it is considered that the antibody of the present disclosure exhibits the above-described effects since it binds to an epitope that is different from an epitope to which trastuzumab binds and inhibits HER2 in a different manner from that of trastuzumab.

BEST MODE FOR CARRYING OUT INVENTION

Hereinafter, the present disclosure will be described in detail through examples. However, the following examples are for illustrative purposes only and it will be apparent to those of ordinary skill in the art that the scope of the present disclosure is not limited by the examples.

EXAMPLES

Example 1: Development of Anti-HER2 Antibody

For development of antibodies, the extracellular domain (ECD) of the HER2 protein was produced using animal cells. The DNA in which a hinge and an Fc region (CH2-CH3) of human IgG1 were bound to the C-terminus of ECD was cloned into pCEP4 (Invitrogen, Cat. No. V044-50) using HindIII and BamHI restriction enzymes. Then, the cloned vector was transiently transformed into FreeStyle 293F (Invitrogen, Cat. No. R790-07) cells using polyethyleneimine (Polyscience Inc., Cat. No. 23966) and then purified from the cell culture using a Protein-A Ceramic HyperD F resin (PALL, Cat No. 20078-028). The purified protein was quantitated using a protein assay dye (Bio-Rad, Cat. No. 500-0006) and its concentration and purity were investigated via Coomassie Blue staining following SDS-PAGE. 100 μg of the protein antigen was mixed with a Freund's adjuvant (Sigma, Cat. No. F5506) and then injected intraperitoneally into BALB/c mouse (Dae Han Bio). 2 weeks later, 100 μg of the antigen diluted in PBS was injected further. 3 days later, the spleen of the mouse was taken out and lymphocytes were isolated. The isolated lymphocytes were mixed with 5P2/0-Ag14 myeloma cells (ATCC, Cat. No. CRL-1581) at a ratio of 5:1 and then fused using PEG-1500 (Roche, Cat. No. 783641). The fused cells (hybridoma) were selectively sorted out and cultured in a medium containing a HAT supplement (Sigma, Cat. No. H0262).

The obtained hybridoma cells were examined via ELISA to determine whether they were the cells producing an antibody that bind to the antigen. HER2-ECD-Fc or ChromPure human IgG (hIgG, Jackson Immunoresearch Lab. Inc., Cat. No. 009-000-003) was immobilized at room temperature onto a Costar 96-well plate (Corning, Cat. No. 3590) at a concentration of 1 μg/mL for 1 hour. The resultant was washed 3 times with TBS-T (0.05% Triton X-100) and then blocked at room temperature for 30 minutes with 300 μL of TBS-T/SM (2% skim milk). After washing the blocked plate 3 times and adding the hybridoma culture, the antibody was allowed to bind at 37° C. for 1 hour. After washing 3 times and then adding anti-mIgG-HRP (Pierce, Cat. No. 31439) diluted to 1:5,000 in TBS-T/SM, as a secondary antibody, the antibody was allowed to bind at 37° C. for 1 hour. After washing the resultant 3 times and adding TMB (SurModics, Cat. No. TMBC-1000-01), the mixture was allowed to develop color at room temperature for 5 minutes. Then, the color development was stopped by adding 1 N sulfuric acid (DukSan, Cat. No. 254). Absorbance was measured at 450 nm using Victor X3 (PerkinElmer, Cat. No. 2030-0030) and the antibody binding specifically to HER2-ECD-Fc was selected.

Since HER2 is a protein expressed on cell surface, it was investigated whether the developed antibody was bound to HER2-overexpressing cells via cell-based ELISA. HER2-overexpressing SKOV-3 ovary cancer cells (Korean Cell Line Bank, Cat. No. 30077) were aliquoted onto a Costar 96-well cell culture plate (Corning, Cat. No. 3595) at 10,000 cell/well and then cultured for 24 hours. On the following day, after removing the cell culture supernatant, the resultant was washed 3 times with PBS and cultured further at 37° C. for 2 hours after adding the hybridoma cell culture. After washing 3 times with TBS-T and adding goat anti-mIgG-HRP diluted in PBS/FBS (3% FBS) to 1:5,000, as a secondary antibody, the resultant was treated at room temperature for 1 hour. After washing 3 times with TBS-T, it was allowed to develop color using TMB. 61 clones showing higher absorbance than that of the SP2/0 cell culture as a negative control group were selected.

The five antibodies (hz2G10, hz39D2, 24D3, 1G3, hz8G11) finally selected from the monoclonal antibodies binding specifically to HER2 were modified to chimeric antibodies or humanized antibodies (hz). The amino acid sequences of the chimeric antibodies or humanized antibodies are described in the attached sequence listings.

The absorbance of the finally selected five antibodies (hz2G10, hz39D2, 24D3, 1G3, hz8G11) is shown in FIG. 1 and Table 1.

Verification of binding of HER2 proteins of five selected antibodies to extracellular domain (ECD)

| Antibodies | Concentration (μg/mL) | | | | | | | | |
|---|---|---|---|---|---|---|---|---|---|
| | $5 \times 10^{-7}$ | $5 \times 10^{-6}$ | $5 \times 10^{-5}$ | $5 \times 10^{-4}$ | $5 \times 10^{-3}$ | $5 \times 10^{-2}$ | $5 \times 10^{-1}$ | 5 | 50 |
| PBS | 0.13 | 0.13 | 0.14 | 0.14 | 0.14 | 0.13 | 0.16 | 0.15 | 0.14 |
| hz2G10 | 0.12 | 0.12 | 0.12 | 0.12 | 0.22 | 1.16 | 2.69 | 2.79 | 2.81 |
| hz39D2 | 0.12 | 0.12 | 0.15 | 0.47 | 2.29 | 2.92 | 2.78 | 2.90 | 2.83 |
| 24D4 | 0.11 | 0.11 | 0.12 | 0.22 | 1.13 | 2.76 | 2.90 | 2.92 | 2.75 |
| 1G3 | 0.11 | 0.11 | 0.14 | 0.35 | 1.77 | 2.79 | 2.78 | 2.81 | 2.76 |
| hz8G11 | 0.12 | 0.12 | 0.14 | 0.34 | 1.67 | 2.72 | 2.94 | 2.90 | 2.74 |

Example 2: Verification of Binding Site of Developed Antibody for HER2 Protein The binding site of the selected five antibodies (hz2G10, hz39D2, 24D3, 1G3, hz8G11) for the extracellular domain (ECD) of the HER2 protein was verified by ELISA. For ELISA, the extracellular domain (ECD) of the ERBB family protein was produced using animal cells and was used as an antigen. Specifically, the DNA in which a hinge and an Fc region ($CH_2$—$CH_3$) of human IgG1 were bound to the C-terminus of ECD was cloned into pCEP4 (Invitrogen, Cat. No. V044-50) using HindIII and BamHI restriction enzymes. Then, the cloned vector was transiently transformed into FreeStyle 293F (Invitrogen, Cat. No. R790-07) cells using polyethyleneimine (Polyscience Inc., Cat. No. 23966) and then HER2-ECD DI Fc, HER2-ECD DII Fc, HER2-ECD DIII Fc, HER2-ECD DIV Fc and HER2-ECD Fc fusion proteins were purified from the cell culture using a Protein-A Ceramic HyperD F resin (PALL, Cat No. 20078-028). The purified protein was quantitated using a protein assay dye (Bio-Rad, Cat. No. 500-0006) and its concentration and purity were investigated via Coomassie Blue staining following SDS-PAGE.

The HER2-ECD DI Fc, HER2-ECD DII Fc, HER2-ECD DIII Fc, HER2-ECD DIV Fc and HER2-ECD Fc fusion proteins were immobilized at 4° C. overnight onto a Costar 96-well plate (Corning, Cat. No. 3590) at a concentration of 1 μg/mL for 1 hour. The resultant was washed 3 times with TBS-T (0.05% Triton X-100) and then blocked at room temperature for 1 hour with 100 μL of TBS-T/BSA (5% BSA). After washing the blocked plate 3 times and adding the anti-HER2 antibody, the antibody was allowed to bind at room temperature for 1 hour. After washing 3 times and then adding anti-human IgG-HRP diluted to 1:3,000 in TBS-T/BSA, as a secondary antibody, the antibody was allowed to bind at room temperature for 1 hour. After washing the resultant 3 times and adding TMB (SurModics, Cat. No. TMBC-1000-01), the mixture was allowed to develop color at room temperature for 5 minutes. Then, the color development was stopped by adding 1 N sulfuric acid (DukSan, Cat. No. 254). Absorbance was measured at 450 nm using Victor X3 (PerkinElmer, Cat. No. 2030-0030).

Figure 2:
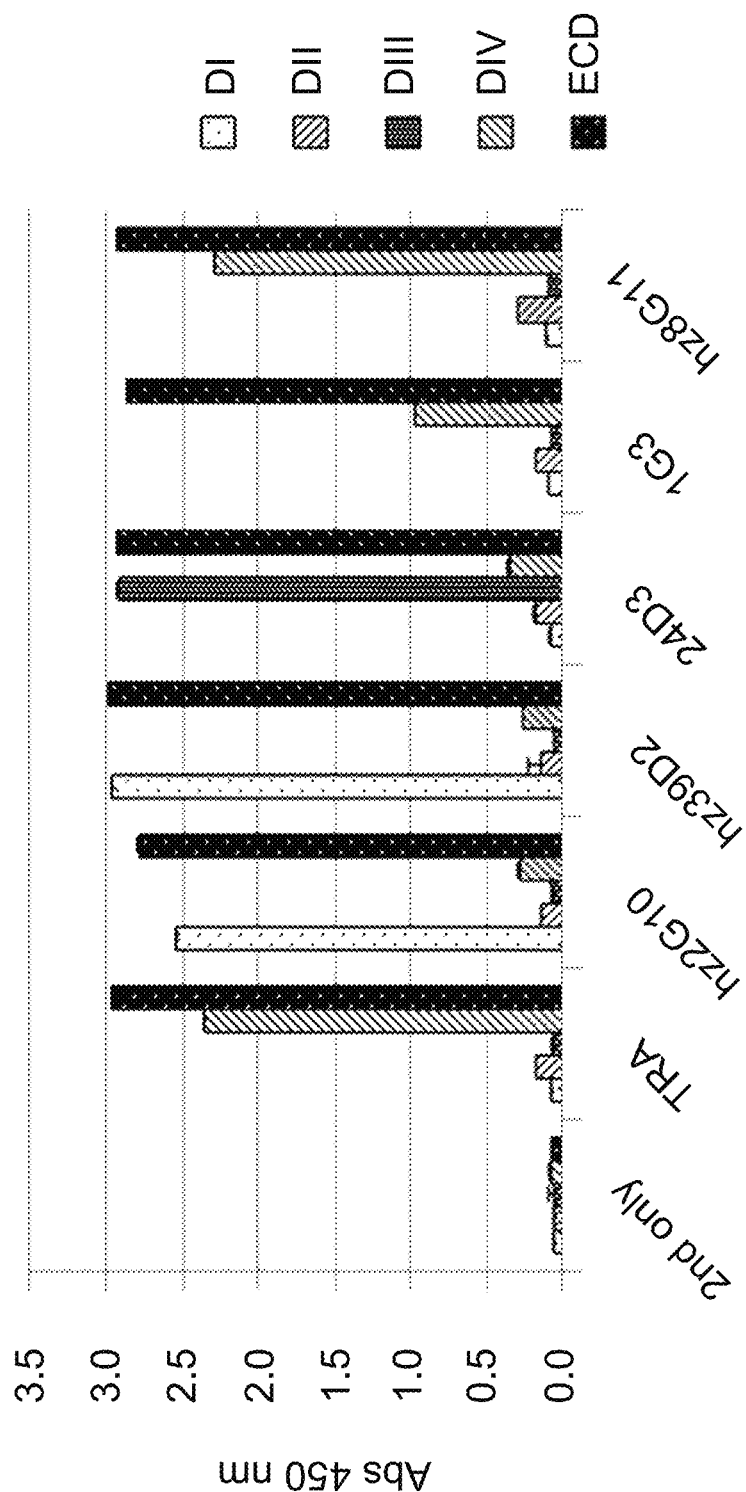
FIG. 2 is a bar graph showing the a results of investigating the extracellular domain of HER2 to which hz2G10, hz39D2, 24D3, 1G3 and hz8G11 clones bind.

The result is shown in FIG. 2.

As show in FIG. 2, among the antibodies developed in the present disclosure, hz2G10 and hz39D2 were bound to the domain 1 of the extracellular domains of the HER2 protein, 24D3 was bound to the domain 3, and 1G3 and hz8G11 were bound to the domain 4.

From this result, it can be seen that the five antibodies of the present disclosure can inhibit the growth of the HER2-overexpressed cancer cells by binding to the HER domain which is different from the extracellular domain 4 of the HER2 protein to which trastuzumab (TRA) binds (hz2G10, hz39D2, 24D3), or can exhibit remarkably superior effect of inhibiting cellular growth when used alone or co-administered with trastuzumab. Therefore, they can be usefully used for prevention or treatment of cancer related with the expression of the HER2 proteins either alone or together with trastuzumab.

Example 3: Comparison of Inhibitory Effect of Developed Antibody Against Growth of Breast Cancer Cells Cell viability was analyzed by treating HER2-overexpressed SKBR3 breast cancer cells or HER2-unexpressed breast cancer cells with MCF-7 either alone or together with trastuzumab. For co-administration, the developed antibody and trastuzumab were mixed at a weight ratio of 1:1. SKBR3 cells (Korean Cell Line Bank, Cat. No. 30030, 5,000 cells/well) and MCF-7 cells (ATCC, Cat. No. HTB22, 5,000 cells/well) were aliquoted onto a 96-well plate and cultured for 24 hours. The cells were cultured further for 4 days after treating with the purified antibody at a final concentration of 20 μg/mL. For measurement of cell viability, CCK-8 (Dojindo, Cat. No. CK-04-13) was added to a final concentration of 10% and absorbance was measured after treating at 37° C. for 3 hours. Relative cell viability was calculated with respect to the absorbance of the antibody-untreated well as 100%.

The result is shown in FIGS. 3a-3d and Table 2.

Relative cell viability of HER2-positive SKBR3 breast cancer cells and HER2-negative MCF-7 breast cancer cells treated with antibody (single treatment)

| Clones | Relative cell viability at 20 μg/mL (%) | |
|---|---|---|
| | SKBR3 | MCF-7 |
| hIgG | 94.68 | 92.11 |
| TRA (trastuzumab) alone | 63.68 | 98.22 |
| hz2G10 | 89.06 | 97.43 |
| hz39D2 | 96.46 | 91.42 |
| 24D3 | 93.97 | 87.33 |
| 1G3 | 74.81 | 98.66 |
| hz8G11 | 74.02 | 98.95 |

Figure 3A:
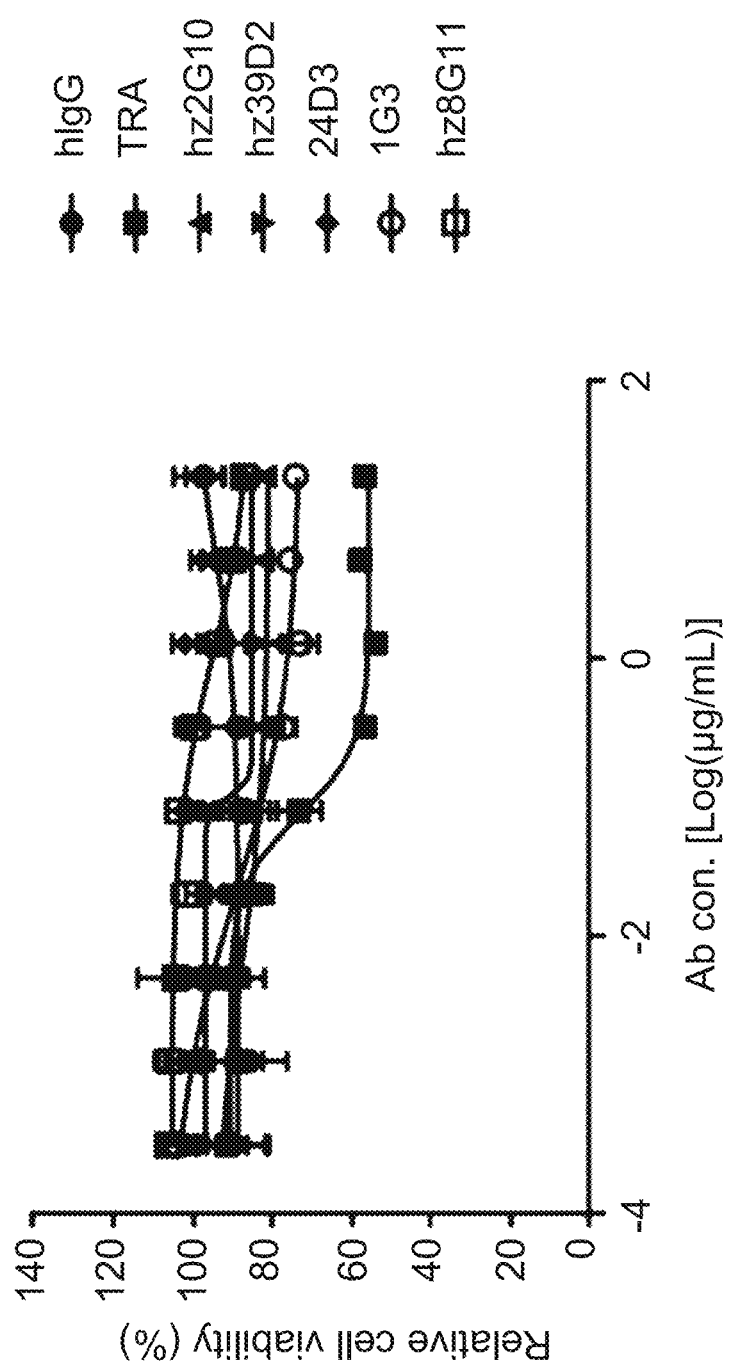
FIG. 3A and FIG. 3B are line graphs showing the results of analyzing the effect of single administration of five antibodies of the present disclosure (hz2G10, hz39D2, 24D3, 1G3 and hz8G11) on the inhibition of the growth of HER2-overexpressed breast cancer cells (SKBR3) and HER2-unexpressed breast cancer cells (MCF-7).
Figure 3B:
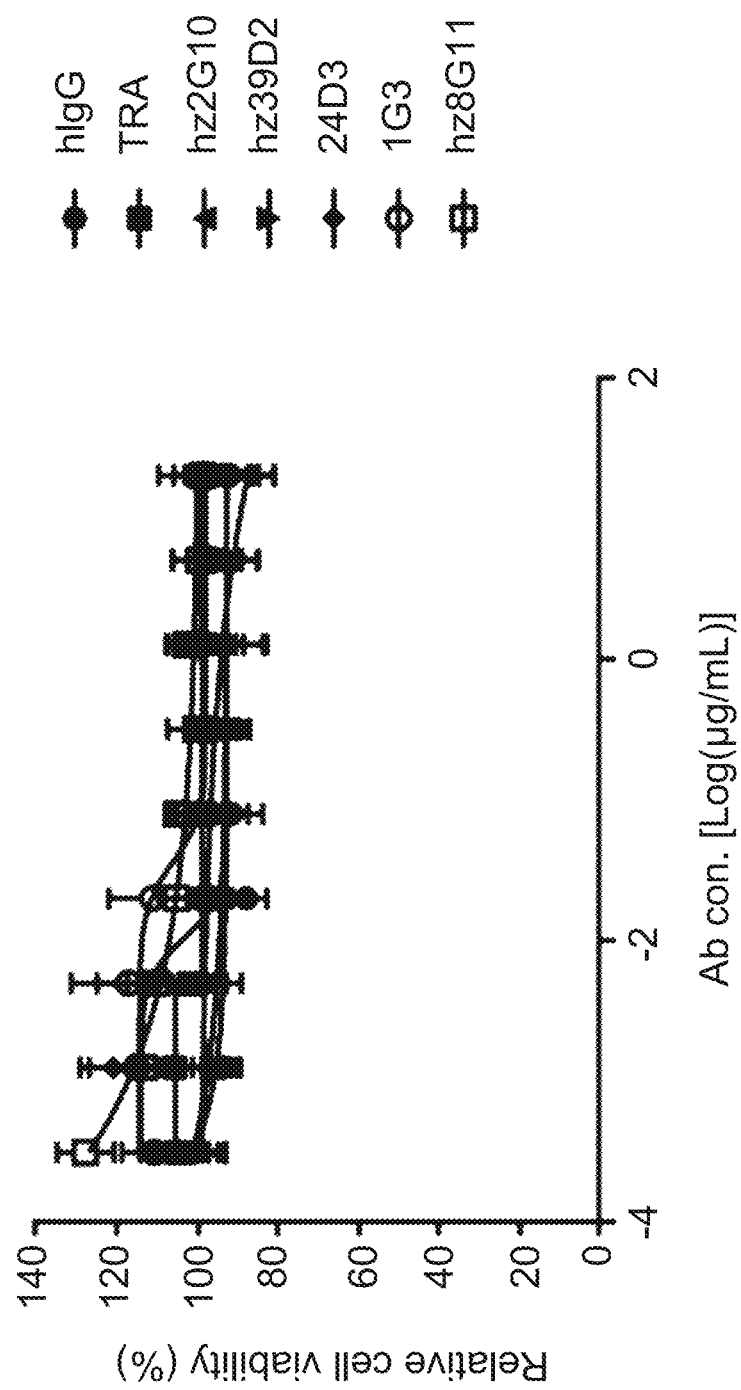

In the above table, hIgG stands for human IgG. As seen from FIG. 3A, FIG. 3B and Table 2, the five antibodies of present disclosure showed the effect of inhibiting the proliferation of SKBR3 breast cancer cells when treated alone. They showed comparable or better effect of inhibiting cellular growth as compared to the positive control trastuzumab at different concentrations (FIG. 3A). However, the five antibodies of present disclosure did not show significant effect of inhibiting cell proliferation of the HER2-negative MCF-7 cells like the positive control trastuzumab (FIG. 3B).

Relative cell viability of HER2-positive SKBR3 breast cancer cells and HER2-negative MCF-7 breast cancer cells treated with antibody (co-treatment)
Relative cell viability at 20 μg/mL (%)

| Clones | SKBR3 | MCF-7 |
|---|---|---|
| hIgG | 94.68 | 92.11 |
| TRA (trastuzumab) alone | 63.68 | 98.22 |
| TRA + hz2G10 | 68.98 | 90.56 |
| TRA + hz39D2 | 77.29 | 90.62 |
| TRA + 24D3 | 63.75 | 97.21 |
| TRA + 1G3 | 62.16 | 102.33 |
| TRA + hz8G11 | 52.62 | 98.41 |

Figure 3C:
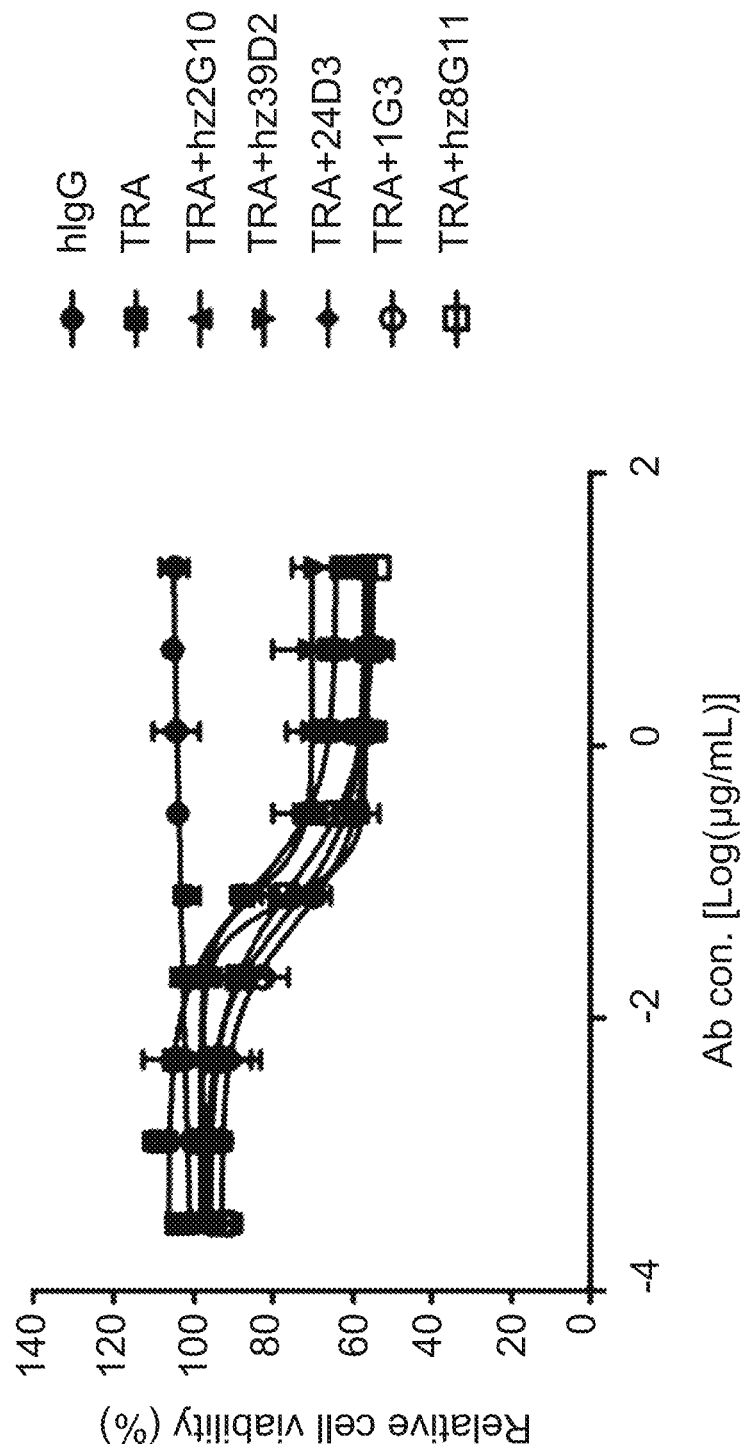
FIG. 3C and FIG. 3D are line graphs showing the results of analyzing the effect of co-administration of five antibodies of the present disclosure (hz2G10, hz39D2, 24D3, 1G3 and hz8G11) and the trastuzumab (TRA) antibody on the inhibition of the growth of HER2-overexpressed breast cancer cells (SKBR3) and HER2-unexpressed breast cancer cells (MCF-7).
Figure 3D:
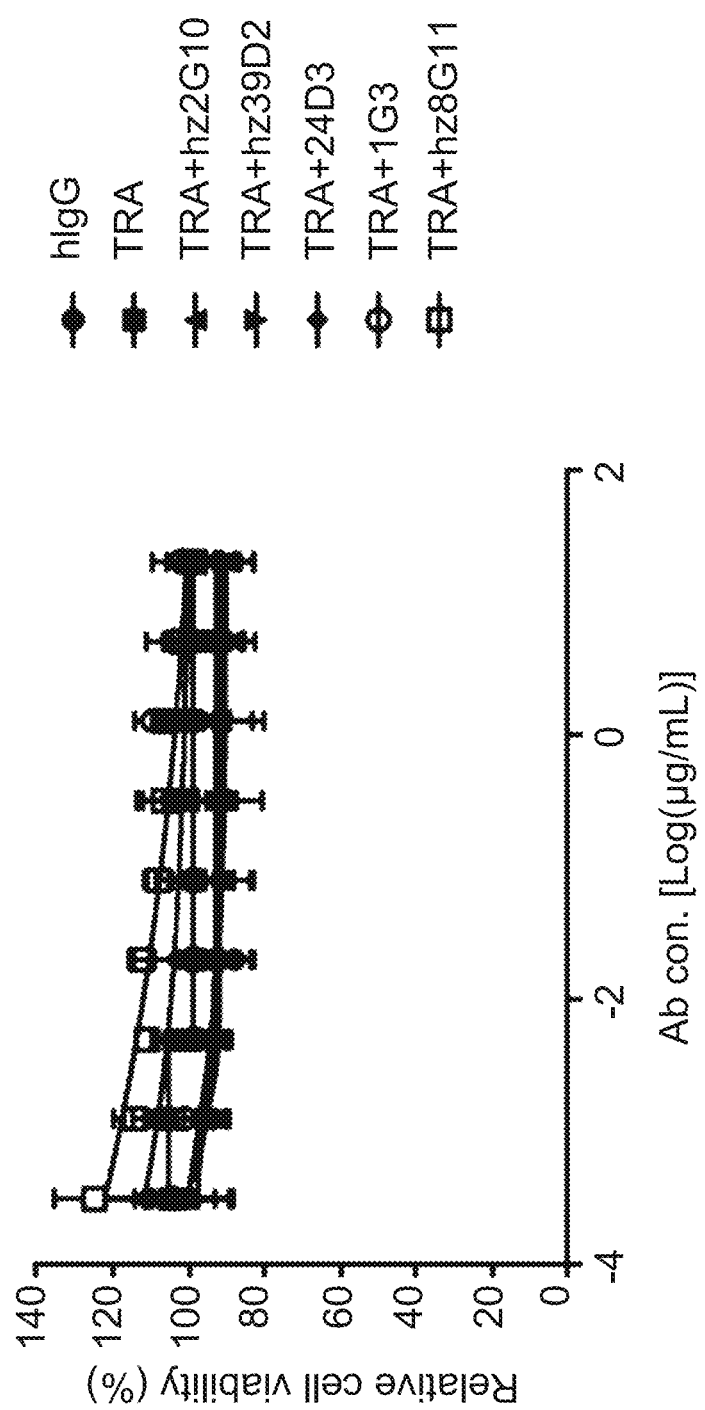

In the above table, hIgG denotes the test group treated with human IgG, and TRA+ denotes the test groups co-administered with trastuzumab and the antibody of the present disclosure. As seen from FIG. 3C, FIG. 3D and Table 3, all of the five antibodies of present disclosure (hz2G10, hz39D2, 24D3, 1G3, hz8G11) showed comparable or better effect of inhibiting cellular growth when treated to the SKBR3 breast cancer cells together with trastuzumab as compared to single treatment with trastuzumab (FIG. 3C).

Without wishing to be bound by theory, it is considered that the antibody of the present disclosure exhibits the above-described effect since it binds to an epitope on HER2 that is different from an epitope to which trastuzumab binds and inhibits HER2 in a different manner from that of trastuzumab.

Example 4: Antibody Sequence Analysis

For analysis of the antibody sequence, a phage Fab antibody library was constructed using the respective hybridoma RNAs and a 3-step panning was conducted to obtain a phage that binds to HER2-ECD-Fc (Phage display: a laboratory manual, Carlos Barbas III, et al., Cold Spring Harbor Laboratory Press). After culturing the hybridoma, RNA was isolated using the SV total RNA isolation system (Promega, Cat. No. Z3100) and cDNA was synthesized therefrom. Using a known primer set (see Phage display: a laboratory manual, Carlos Barbas III, et al., Cold Spring Harbor Laboratory Press), the variable region of the antibody was amplified and cloned into the pComb3X vector (Barbas Laboratory, Scripps Research Institute) using a Sfi-I restriction enzyme after ligating to human Ck (kappa chain) and CH1, and then transformed into ER2537 bacteria (New England Biolabs, Cat. No. 801-N). The transformed bacteria were transfected with the VCSM13 helper phage (Stratagene, Cat. No. 200251) and a clone which binds to HER2-ECD-Fc was obtained using an immunotube to which HER2-ECD-Fc was immobilized.

From the colonies of the antibodies, the antibody that binds to HER2-ECD-Fc was confirmed via ELISA. The colonies of the transformed bacteria were cultured at 37° C. until the absorbance at 600 nm reached 0.5, treated with IPTG at a final concentration of 1 mM, and allowed to express antibodies in the form of Fab while culturing overnight at 30° C. After collecting cells by centrifuging 5 mL of the culture, the cells were suspended in 0.4 mL of 1×TES (50 mM Tris, 1 mM EDTA, 20% (v/v) sucrose, pH 8.0) and then treated at 4° C. for 10 minutes. After adding 0.6 mL of 0.2×TES thereto and treating further at 4° C. for 30 minutes, the resultant was centrifuged and a supernatant was taken. After washing a Costar 96-well half area plate (Corning Inc., Cat. No. 3690) coated with HER2-ECD-Fc at a concentration of 1 μg/mL 3 times with TBS-T, it was blocked with TBS-T/SM (3% non-fat skim milk, 0.05% Triton X-100) at room temperature for 1 hour. The culture broth or periplasmic extract (periplasm) of each colony was diluted at a ratio of 1:3 using TBS-T/SM and allowed to bind at room temperature for 1 hour. After washing 3 times and diluting to 1:5000 with anti-HA-HRP (Roche, Cat. No. 120-138-190-01) as a secondary antibody, the resultant was allowed to bind at room temperature for 1 hour. After washing 3 times, the resultant was allowed to develop color using TMB.

Most colonies showed absorbance of 0.2 or higher in the cell culture or periplasmic extract, and the base sequence of the antibody was analyzed for these clones. The base sequence analysis revealed that the colonies derived from the single hybridoma had the same sequences.

The CDR sequence of the antibody produced from each clone is summarized in Table 4 and Table 5.

TABLE 4

| Clones | CDRH1 | CDRH2 | CDRH3 |
|---|---|---|---|
| hz2G10 | DYYMY (SEQ ID NO 1) | YINSGGGSTYYPDTVKG (SEQ ID NO 2) | EALYDYDYAMDY (SEQ ID NO 3) |
| hz39D2 | NYGVN (SEQ ID NO 7) | WINTHTGEPTYAEEFKG (SEQ ID NO 8) | DDYYVRVDY (SEQ ID NO 9) |
| 24D3 | SCAMS (SEQ ID NO 13) | TISGGGSYTYYPDSVKG (SEQ ID NO 14) | HGGYESWFPY (SEQ ID NO 15) |
| 1G3 | DTYMH (SEQ ID NO 19) | RIDPANGYTRYDPNFQG (SEQ ID NO 20) | YYYGFYAMDY (SEQ ID NO 21) |
| hz8G11 | GYYMH (SEQ ID NO 25) | HINPNNGGTSYNQKFKG (SEQ ID NO 26) | EEAFAY (SEQ ID NO 27) |

TABLE 5

| Clones | CDRL1 | CDRL2 | CDRL3 |
|---|---|---|---|
| hz2G10 | KSSQSLLYSNGKTYLN (SEQ ID NO 4) | LVSKLDS (SEQ ID NO 5) | VQGTHFPLT (SEQ ID NO 6) |
| hz39D2 | KASQDINSYLS (SEQ ID NO 10) | RANRLVD (SEQ ID NO 11) | LQYDEFPWT (SEQ ID NO 12) |
| 24D3 | RSSQSLVHSNGNTYLH (SEQ ID NO 16) | KVSNRFS (SEQ ID NO 17) | SQSTHVPPWT (SEQ ID NO 18) |
| 1G3 | KASQDVSTAVA (SEQ ID NO 22) | SASYRYT (SEQ ID NO 23) | QQHYSTPPT (SEQ ID NO 24) |
| hz8G11 | RASQDISNYLN (SEQ ID NO 28) | YTSRLHS (SEQ ID NO 29) | QQGITPPWT (SEQ ID NO 30) |

Tables 4 and 5 show the amino acid sequences of the heavy chain CDR (CDRH) and the light chain CDR (CDRL) of the developed antibodies.

Example 5: Specificity of Developed Antibody for HER2

It was investigated whether the developed five antibodies of the present disclosure specifically bind to HER2 belonging to the ErbB family proteins by ELISA. In order to confirm whether the developed antibody binds specifically to HER2 belonging to the ErbB family proteins, the extracellular domains of EGFR, HER2, HER3 and HER4 belonging to the ErbB family were examined via ELISA. The extracellular domain of EGFR (EGFR-ECD-Fc) was produced in the same manner as the HER2-ECD-Fc described above in Example 2, and the HER3 (R&D Systems, #348-RB-050) and HER4 (R&D Systems, #1131-ER-050) proteins were purchased. Cetuximab (CET), trastuzumab (TRA) and patritumab (AMG888, AMG) were used as control group antibodies binding to EGFR, HER2 and HER3, respectively.

Figure 4:
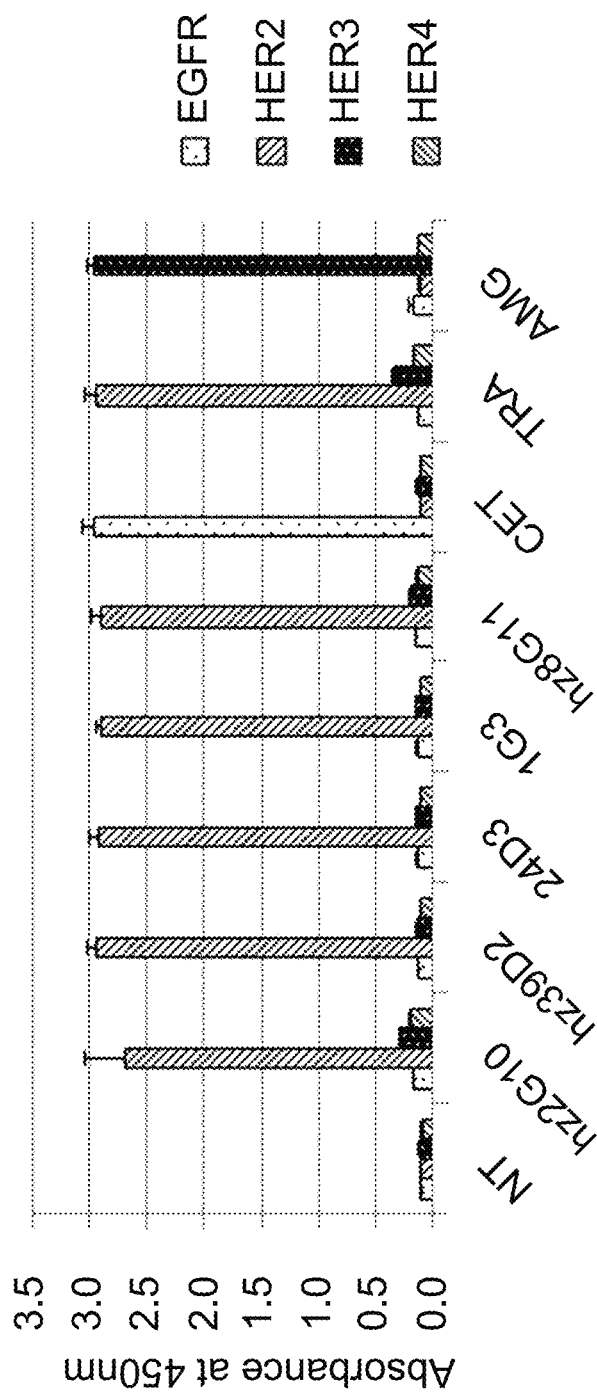
FIG. 4 is a bar graph showing the results of investigating the specificity of antibodies developed by expressing the ErbB family. Cetuximab (CET), trastuzumab (TRA) and patritumab (AMG888, AMG) were used as control groups binding to EGFR, HER2 and HER3, respectively.
Figure 5A:
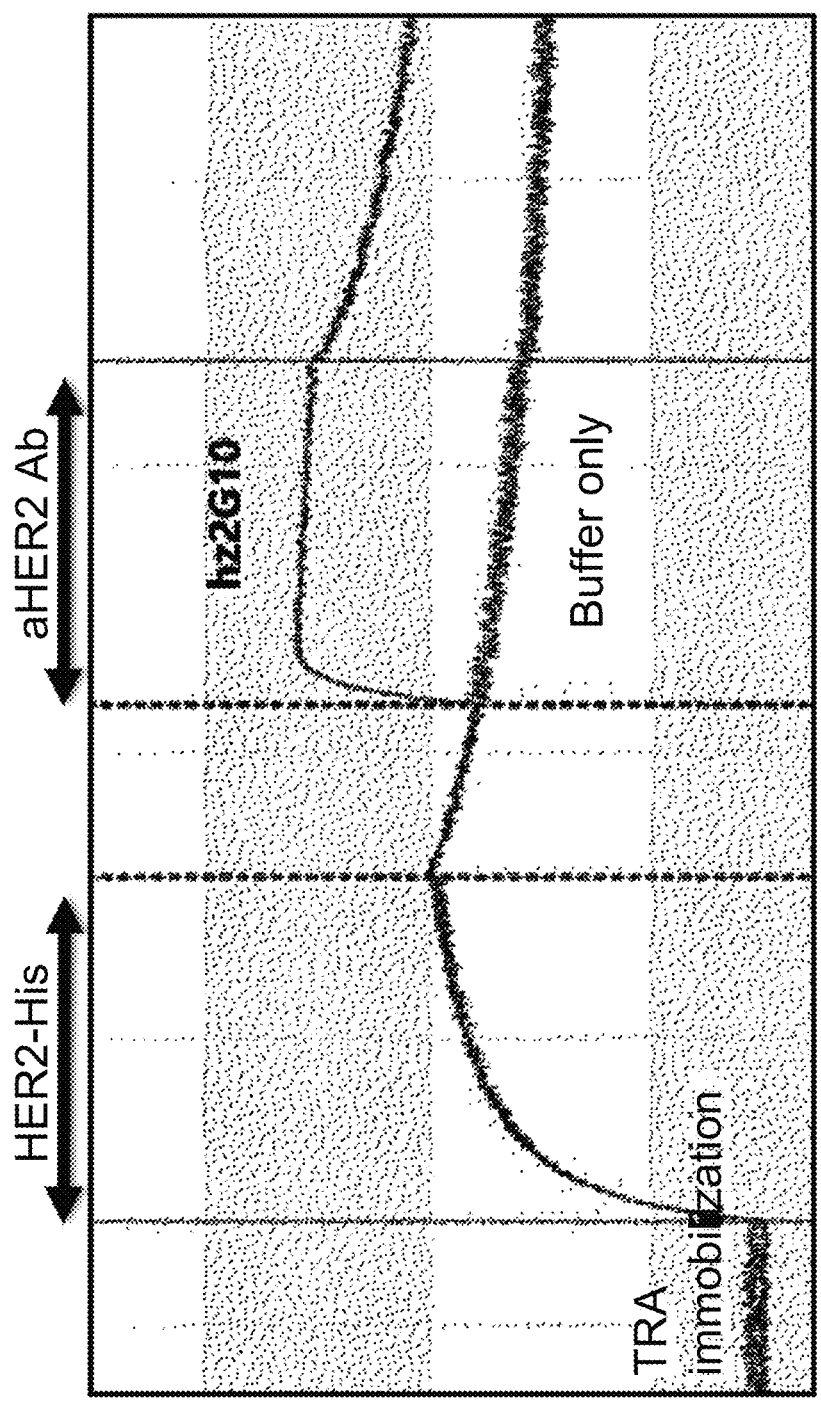
FIGS. 5A-5E are line graphs showing the results of comparing the epitopes of developed antibodies with trastuzumab. For comparison with the epitope of trastuzumab, trastuzumab and HER2-His were immobilized on a sensor chip and then the binding with five antibodies of the present disclosure was analyzed.
Figure 5B:
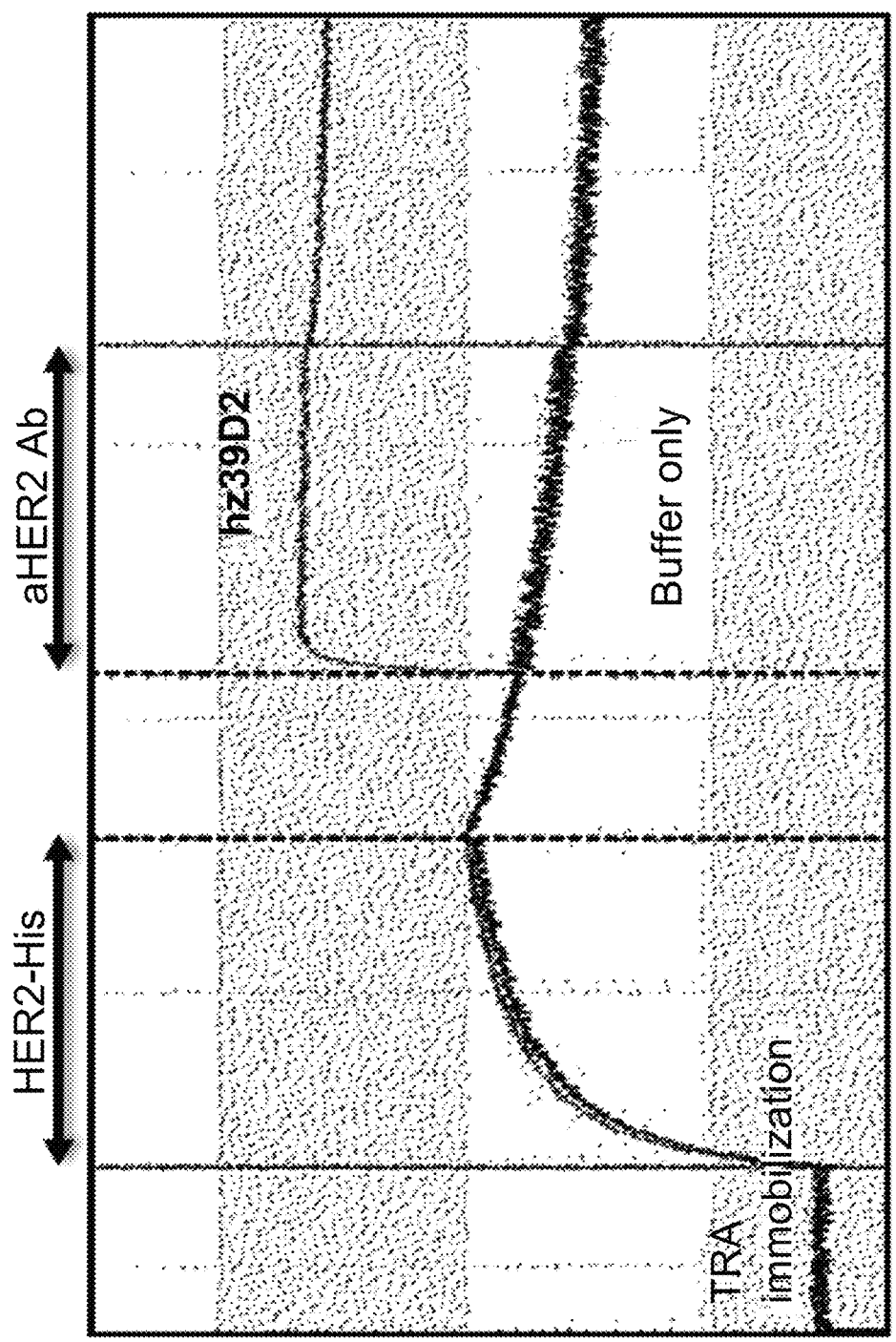
Figure 5C:
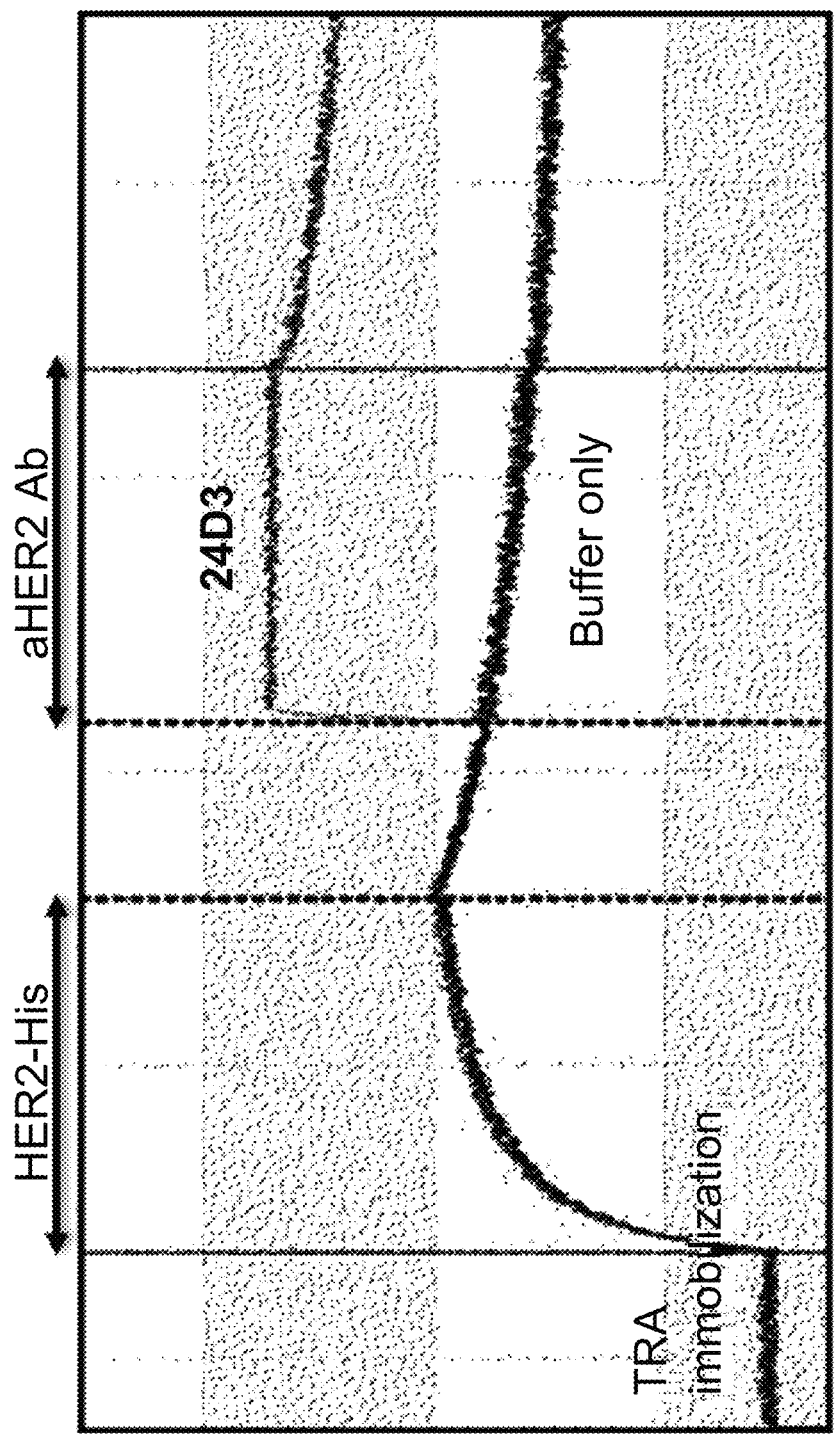
Figure 5D:
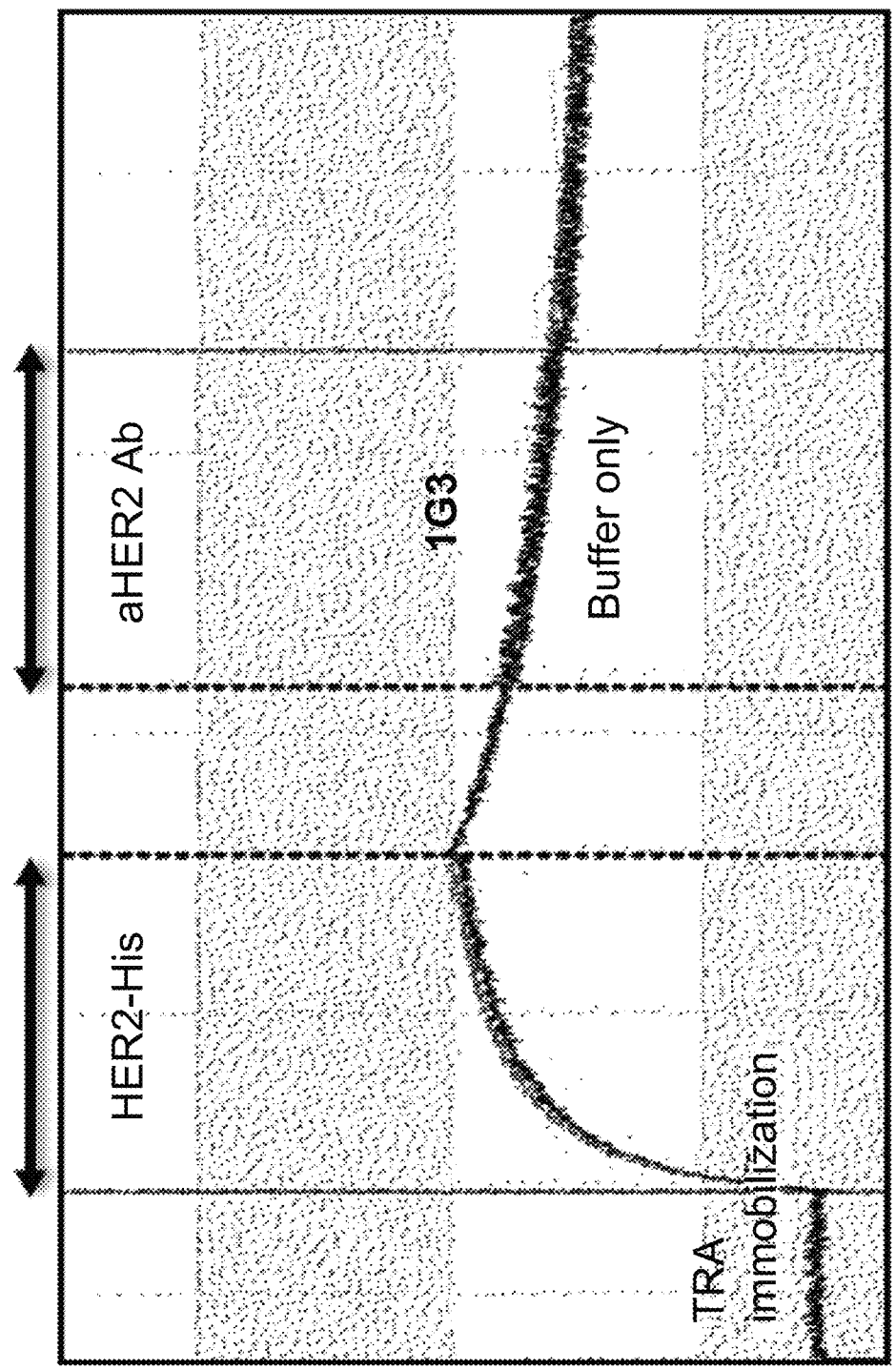
Figure 5E:
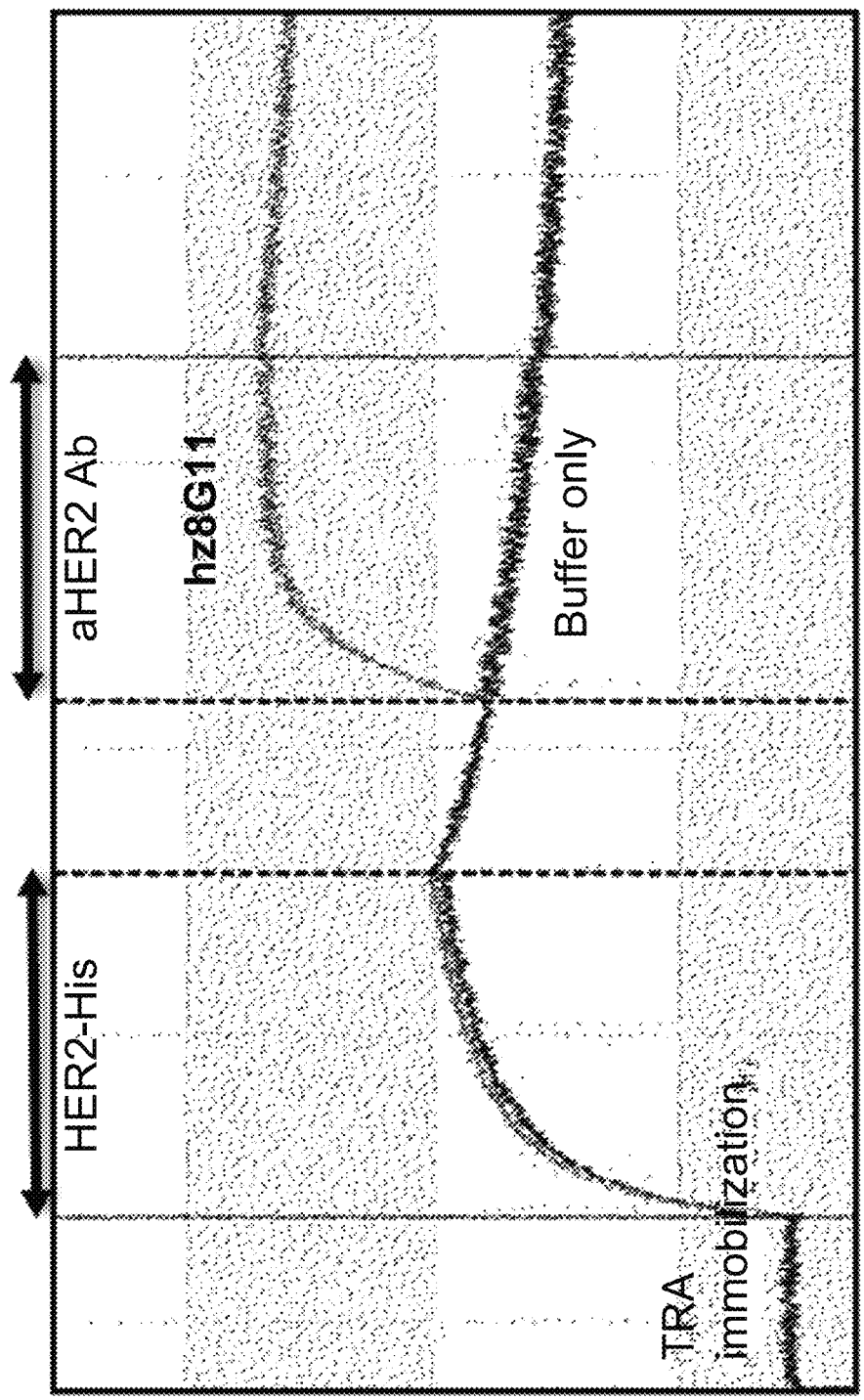

The result is shown in FIG. 4.

As seen from FIG. 4, it was confirmed that the five antibodies of the present disclosure bind specifically to HER2 among the human ErbB family proteins.

Example 6: Comparison of Epitopes of Developed Antibody and Trastuzumab

It is known that the anti-HER2 antibody trastuzumab binds to the domain 4 among the four domains of HER2 ECD. In order to investigate whether the developed antibodies and trastuzumab share the epitope for HER2, epitope binning was conducted using Octet (Pall ForteBio). Trastuzumab was immobilized onto an AR2G sensor chip (ForteBio, Cat. Nos. 18-5092 (tray), 18-5093 (pack), 18-5094 (case)) at a concentration of 10 μg/mL by amine coupling using ECD/NHS. After allowing the HER2-ECD-His protein to bind to the trastuzumab-immobilized sensor chip at a concentration of 10 μg/mL for 10 minutes, the binding between trastuzumab and HER2-ECD was stabilized for 5 minutes. Then, the five antibodies of the present disclosure were bound at a concentration of 10 μg/mL for 10 minutes and the binding between the antigen and the antibodies was stabilized for 10 minutes. After the immobilization of trastuzumab, all the antibodies and antigen were diluted using a kinetics buffer (ForteBio, Cat No. 18-1092). The same buffer was used during the stabilization. If the additionally added antibody binds to the trastuzumab-bound HER2-ECD protein, it can be interpreted that the antibody does not share the epitope with trastuzumab.

The result is shown in FIGS. 5a-5e.

As seen from FIGS. 5a-5e, it was confirmed that the developed antibodies hz2G10, hz39D2, 24D3 and hz8G11 had different epitopes from that of trastuzumab because they were bound to the trastuzumab-bound HER2-ECD. In contrast, 1G3 did not bind to the trastuzumab-bound HER2-ECD, suggesting that it shares the epitope with trastuzumab.

Example 7: Development of hz39D2 Antibody with Increased Affinity

In order to develop antibodies with improved affinity based on the humanized 39D2 antibody (hz39D2), the inventors of the present disclosure have developed a phage antibody library with CDR3 of the light chain or heavy chain randomized (Phage display: a laboratory manual, Carlos Barbas III, et al., Cold Spring Harbor Laboratory Press). D and Y corresponding to D101 and Y102 of the CDR3 of the heavy chain according to Kabat numbering and P, W and T corresponding to P95, W96, T97 of the CDR3 of the light chain according to Kabat numbering were excluded from the randomization because they are commonly observed amino acids in human antibodies. Primers were synthesized such that adenine (A), cytosine (C), guanine (G) and thymine (T) were inserted randomly into the first and second positions of the codon corresponding to the amino acid to be randomized, with the same ratio, and guanine (G) or cytosine (C) was inserted into the third position at the same ratio. From the developed library, the clones with improved affinity were selected through biopanning using the HER2-ECD-His protein. The CDR sequence data of the finally selected three antibodies, hz39D2.14, hz39D2.22 and hz39D2.23, are summarized in Table 6 and Table 7. The amino acid residues modified to improve affinity are underlined.

TABLE 6

| Clones | CDRH1 | CDRH2 | CDRH3 |
|---|---|---|---|
| hz39D2 | NYGVN (SEQ ID NO 7) | WINTHTGEPTYAEEFKG (SEQ ID NO 8) | DDYYVRVDY (SEQ ID NO 9) |
| hz39D2.14 | NYGVN (SEQ ID NO 7) | WINTHTGEPTYAEEFKG (SEQ ID NO 8) | D<u>E</u>YYVR<u>T</u>DY (SEQ ID NO 71) |
| hz39D2.22 | NYGVN (SEQ ID NO 7) | WINTHTGEPTYAEEFKG (SEQ ID NO 8) | D<u>E</u>YYVRVDY (SEQ ID NO 72) |
| hz39D2.23 | NYGVN (SEQ ID NO 7) | WINTHTGEPTYAEEFKG (SEQ ID NO 8) | D<u>E</u>YYVRVDY (SEQ ID NO 73) |

TABLE 7

| Clones | CDRL1 | CDRL2 | CDRL3 |
|---|---|---|---|
| hz39D2 | KASQDINSYLS (SEQ ID NO 10) | RANRLVD (SEQ ID NO 11) | LQYDEFPWT (SEQ ID NO 12) |
| hz39D2.14 | KASQDINSYLS (SEQ ID NO 10) | RANRLVD (SEQ ID NO 11) | LQYDEFPWT (SEQ ID NO 12) |
| hz39D2.22 | KASQDINSYLS (SEQ ID NO 10) | RANRLVD (SEQ ID NO 11) | L<u>EL</u>DEFPWT (SEQ ID NO 73) |
| hz39D2.23 | KASQDINSYLS (SEQ ID NO 10) | RANRLVD (SEQ ID NO 11) | LQ<u>L</u>DEFPWT (SEQ ID NO 74) |

IgG antibodies were produced to verify the increased affinity of the three selected antibodies (hz39D2.14, hz39D2.22 and hz39D2.23). 2000 RU of goat anti-human IgG (Invitrogen, #H10500) was immobilized onto a CM5 sensor chip by ECD/NHS. Then, the antibodies were allowed to bind at a rate of 50 μL/min for 5 minutes and then stabilized for 5 minutes by flowing a buffer. After stabilizing the antibodies, the HER2-ECD-His protein was allowed to bind at a rate of 50 μL/min for 4 minutes and then separated by flowing a buffer for 15 minutes. After analyzing the concentration, the resultant was recycled using 10 mM glycine (pH 1.5) and then subjected to the subsequent assay. The affinity of the antibodies was analyzed using the BIAevaluation software. The analysis result is summarized in Table 8. As seen from Table 8, all of the three selected antibodies (hz39D2.14, hz39D2.22 and hz39D2.23) showed improved affinity as compared to hz39D2.

TABLE 8

| Clones | $K_a$ (1/Ms) | $K_d$ (1/s) | $K_D$ (M) |
| --- | --- | --- | --- |
| hz39D2 | 6.8E+04 | 2.5E−03 | 3.7E−08 |
| hz39D2.14 | 3.7E+04 | 3.0E−04 | 8.0E−09 |
| hz39D2.22 | 8.1E+04 | 1.6E−04 | 2.0E−09 |
| hz39D2.23 | 7.1E+04 | 2.0E−04 | 2.8E−09 |

Figure 6A:
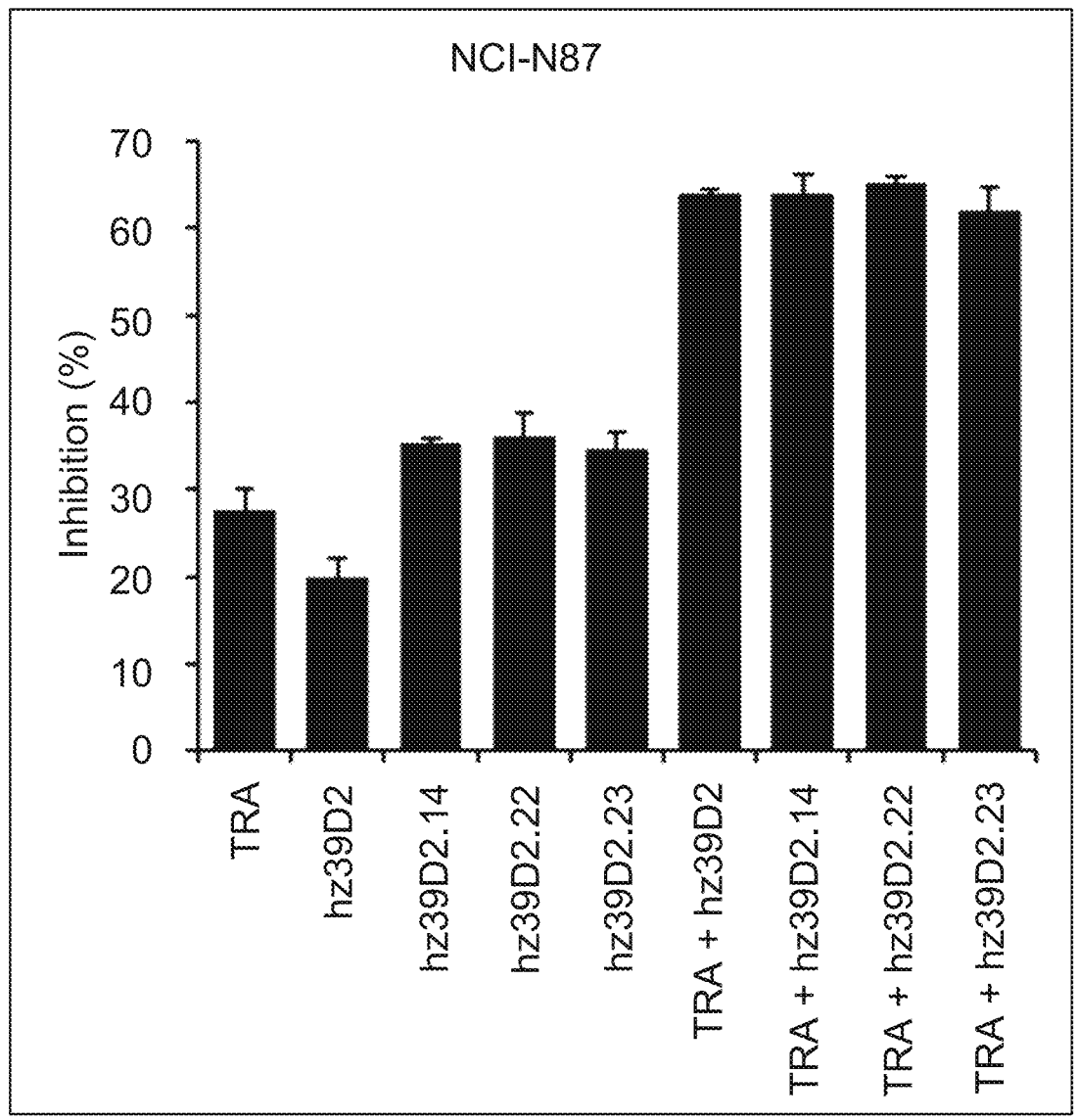
FIGS. 6A-6C are bar graphs showing the results of analyzing the effect of single administration of hz39D2 and affinity-improved clones thereof (hz39D2.14, hz39D2.22 and hz39D2.23) or co-administration with the trastuzumab antibody on the inhibition of the growth of HER2-overexpressed gastric cancer and breast cancer cells.
Figure 6B:
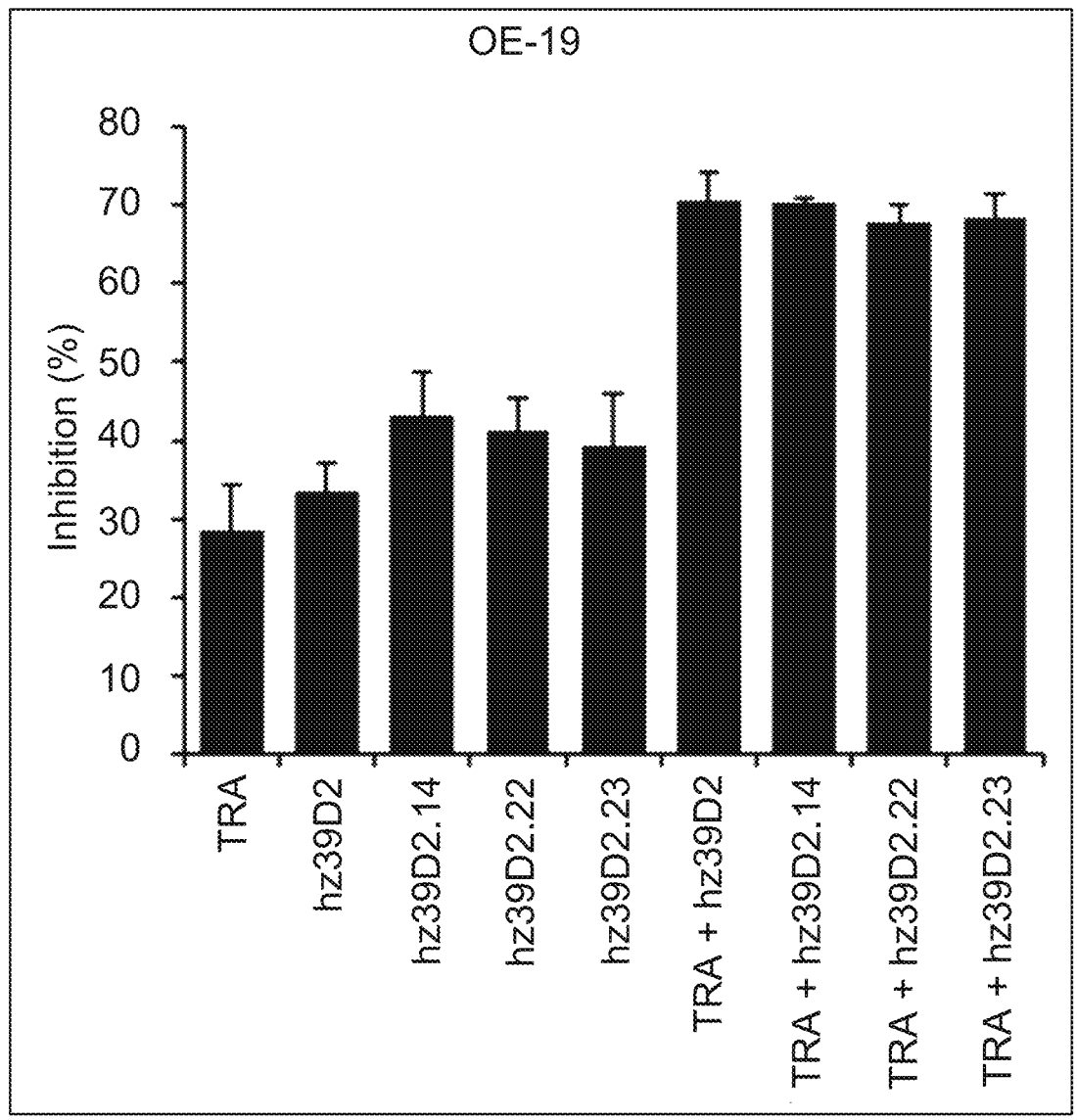
Figure 6C:
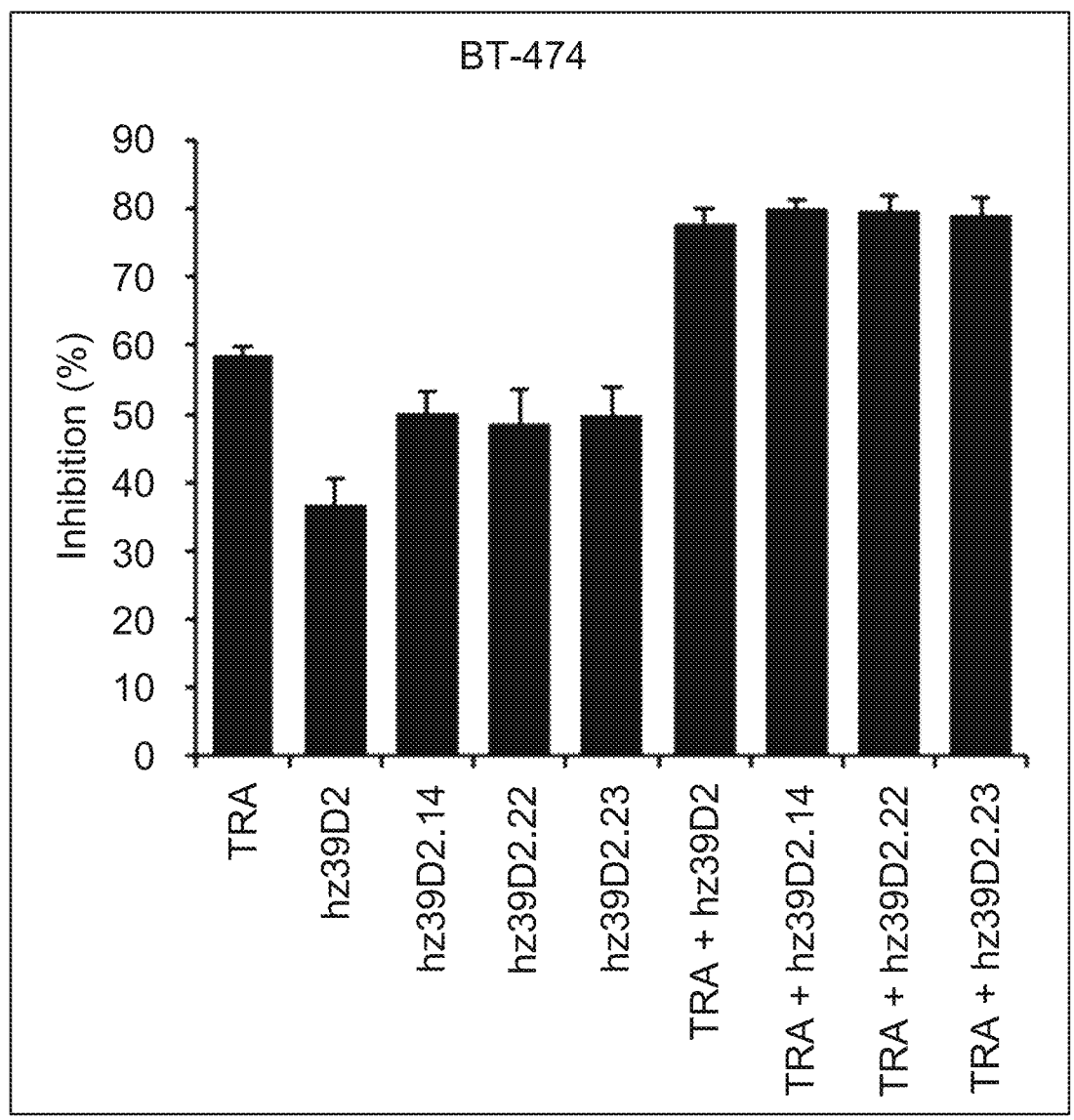
Figure 9B:
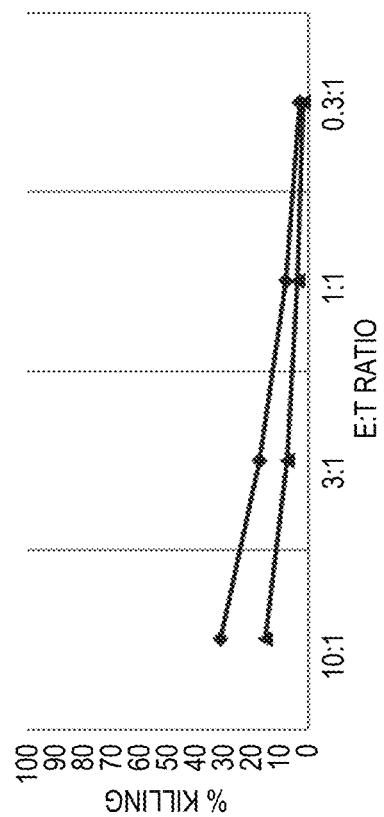
FIGS. 9A-9E are line graphs showing the results of a cell killing assay (Calcein releasing cytotoxicity assay) assessing the cytotoxicity of cord-blood derived NK cells expressing HER2-CAR construct clone #14 against HER2 positive target cancer cell lines.
Figure 9A:
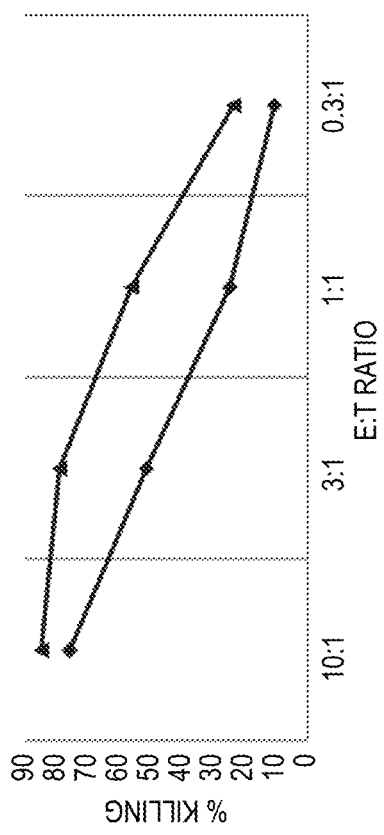
Figure 9C:
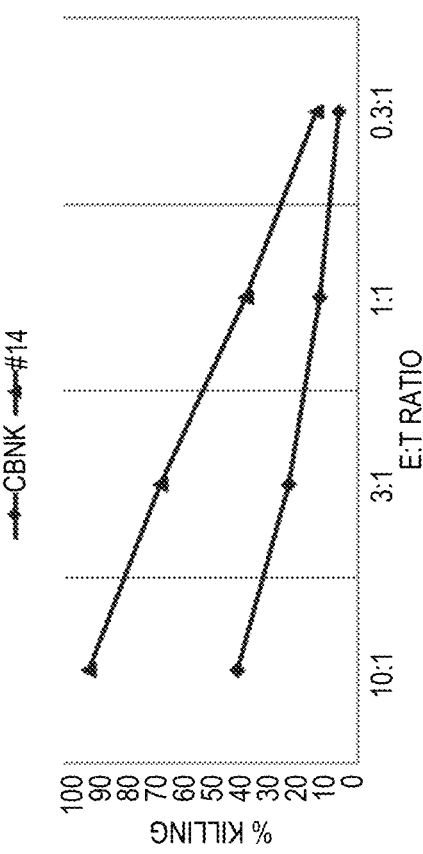
Figure 9D:
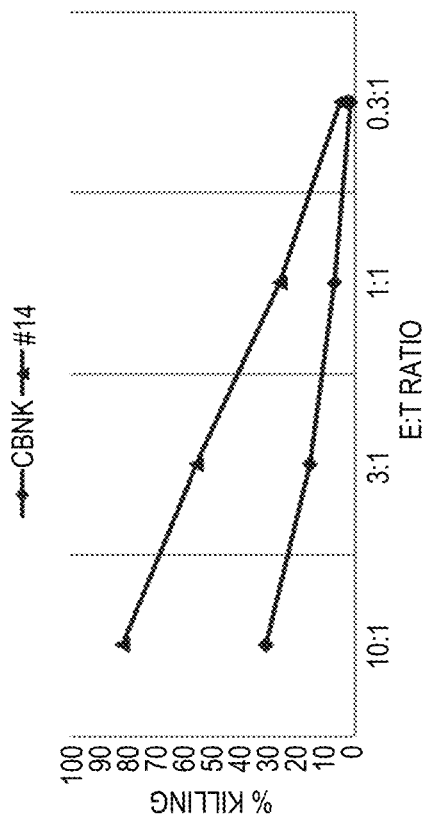
Figure 9E:
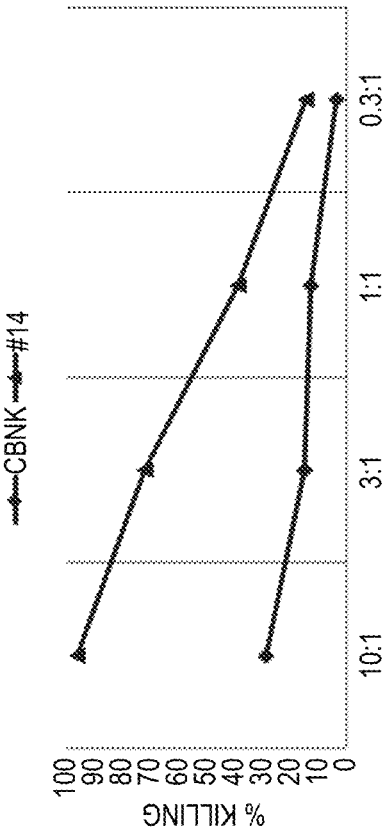

The anticancer effect of the three antibodies (hz39D2.14, hz39D2.22 and hz39D2.23) with improved affinity was analyzed using HER2-overexpressed NCI-N87 and OE-19 gastric cancer cells and BT-474 breast cancer cells. After treating the cells with each antibody at a concentration of 5 µg/mL either alone or in combination with trastuzumab, the viability of the cancer cells was analyzed (FIGS. 6a-6c). As seen from FIGS. 6a-6c, it was confirmed that the hz39D2.14, hz39D2.22, and hz39D2.23 antibodies with improved affinity showed improved effect of inhibiting cancer cell proliferation when treated alone.

Example 8: Construction of Chimeric Antigen Receptors (CAR) Targeting Human HER2

Various CAR domain structures were constructed, cloned into lentivral expression systems, expressed in Umbilical Cord Blood-derived Natural Killer cells and tested in assays of tumor cell engagement and cytotoxic killing. The Anti-Her2 antibody disclosed herein was constructed as a scFv structure and used in combination with various CAR costimulatory domains as described herein.

Plasmid Construction:

A signal sequence comprising the scFv of Her2 specific hz39D2 (VL-GS linker-VH), a hinge and transmembrane domain of CD8a, and intracellular domains of 4-1BB, OX40, OX40 ligand, and CD3ζ were each independently synthesized. These molecules were assembled in various combinations using splicing by overlap extension PCR (SOE-PCR). The sequences of the PCR products were confirmed by direct sequencing. Each PCR product was cut into Nhe1 and EcoRI, and then inserted into Nhe1 and EcoRI sites of a 3rd generation self-inactivating lentiviral expression vector such as MSCV-EF1α-GFP vector or EF1a-MCS vector.

Her2-Z CAR (Clone #2) (SEQ ID NO: 129) was produced by connecting: the signal sequence domain of CD8α (nucleotides 890-952, GenBank NM 001768.6, SEQ ID NO: 112); the extracellular domain of Her2 specific hz39D2 scFv (VL-GS linker-VH) (SEQ ID NO: 114); human CD8α-derived hinge and transmembrane domains (nucleotides 1292-1507, GenBank NM 001768.6, SEQ ID NO: 116 and SEQ ID NO: 118); CD3ζ-derived intracellular signaling domain (nucleotides 299-634, GenBank NM 000734.3, SEQ ID NO: 122); and stop codon TGA.

Her2-BBZ CAR (Clone #3) (SEQ ID NO: 131) was produced by connecting: the signal sequence domain of CD8α (nucleotides 890-952, GenBank NM 001768.6, SEQ ID NO: 112); the extracellular domain of Her2 specific hz39D2 scFv (VL-GS linker-VH) (SEQ ID NO: 114); human CD8α-derived hinge and transmembrane domains (nucleotides 1292-1507, GenBank NM 001768.6, SEQ ID NO: 116 and SEQ ID NO: 118); CD13ζ (4-1BB)-derived intracellular signaling domain (nucleotides 901-1026, GenBank NM 001561.5, SEQ ID NO: 124); CD3ζ-derived intracellular signaling domain (nucleotides 299-634, GenBank NM 000734.3, SEQ ID NO: 122; and stop codon TGA.

Her2-28Z CAR (Clone #6) (SEQ ID NO: 133) was produced by connecting the signal sequence domain of CD8α (nucleotides 890-952, GenBank NM 001768.6, SEQ ID NO: 112); the extracellular domain of Her2 specific hz39D2 scFv (VL-GS linker-VH) (SEQ ID NO: 114); human CD8α-derived hinge domain (nucleotides 1292-1435, GenBank NM 001768.6, SEQ ID NO: 116; CD28-derived transmembrane and intracellular signaling domains (nucleotides 679-882, GenBank NM 006139.3, SEQ ID NO: 120 and SEQ ID NO: 126); CD3ζ-derived intracellular signaling domain (nucleotides 299-634, GenBank NM 000734.3, SEQ ID NO: 122); and stop codon TGA.

Her2-28OX40LZ CAR (Clone #14) (SEQ ID NO: 135) was produced by connecting: the signal sequence domain of CD8α (nucleotides 890-952, GenBank NM 001768.6, SEQ ID NO: 112); the extracellular domain of Her2 specific hz39D2 scFv (VL-GS linker-VH) (SEQ ID NO: 114); CD8α-derived hinge domain (nucleotides 1292-1435, GenBank NM 001768.6, SEQ ID NO: 116); CD28-derived transmembrane and intracellular signaling domains (nucleotides 679-882, GenBank NM 006139.3, SEQ ID NO: 120 and SEQ ID NO: 126); CD252 (OX40 ligand)-derived intracellular signaling domain (nucleotides 141-206, GenBank NM 003326.4, SEQ ID NO: 128); CD3-derived intracellular signaling domain (nucleotides 299-634, GenBank NM 000734.3, SEQ ID NO: 122); and stop codon TGA.

The structures of the HER2 CAR constructs as disclosed herein are summarized in FIG. 7. The domains of the CARs disclosed herein were linked in series (in tandem) to one another and linked in frame.

Virus Production and Gene Transfer:

To prepare VSVG-pseudotyped lentivirus, 293T cells cultured in a DMEM medium were co-transfected with various types of vectors such as PCDH1-MSCV-Her2 specific hz39D2 scFv-construct-EF1-copGFP vector, EF1a-Her2 specific hz39D2 scFv-construct vector, PCDH1-MSCV-EF1-copGFP control vector, or EF1a-GFP control vector (for production of Mock infection virus using empty vector) together with HIV-based pPACKH1 lentivirus Package Kit (System Biosciences). For this purpose, Lipofectamine 2000 reagent (Invitrogen, Carlsbad, Calif.) was used. Each lentivirus was prepared by transfection of 80% dense HEK293T cells in a flask with the various Her2 specific hz39D2 scFv construct expression vectors or a control plasmid together with pPACKH1 lentivirus packaging plasmids. After 6 hours, the medium was replaced by a DMEM medium containing 10% FBS. The conditioned medium containing lentivirus was collected after 48 hours of transfection, followed by filtering with a 0.45 µm filter unit (Milliopore, Billerica, Mass., USA) in order to remove cell debris. A viral supernatant containing the virus was concentrated about 50 times by centrifugation at 3000 rpm and 4° C. for 20 minutes using Amicon Filter (Millipore). The concentrated virus was stored at −80° C.

For the lentiviral infection, PBMC derived NK cells or cord blood derived NK cells in an exponential growth phase were adjusted to a concentration of 1×10$^6$ cells/ml using Cellgro (Cellgenix) including 1% human plasma and 500 IU/mL interleukin-2, and then a lentiviral supernatant in 10 to 50 MOI was added in the presence of 4 µM BX795, 1:400 Lentiboost and 20 ng/ml IL-21 followed by centrifugation at 1000 g for 60 minutes. After centrifugation, the cells were left in a humidified incubator at 37° C. and 5% $CO_2$ conditions. After 24 hours of transduction, the culture medium was replaced: plate was centrifuged at 400 g for 5 minutes and transduction medium was aspirated. Equal volume fresh Cellgro (Cellgenix) including 1% human plasma and 500 IU/mL interleukin-2 was added for future use. Control cells were transduced with a vector only.

Expression Analysis of Anti-HER2-CAR (hz39D2 scFv):

Her2 specific hz39D2 scFv CAR-transduced NK cells, the control vector-transduced NK (NK-Mock) or NK parent cells were washed twice with FACS buffer, and the washed cells were stained using 7-AAD (Beckman coulter), anti-CD3, anti-CD56, and recombinant histidine tagged human HER2 proteins (R&D systems) with PE-conjugated anti-histidne (Abcam) mAbs. An expression ratio and a mean fluorescence intensity (MFI) of the stained cells were measured using a BD LSRFortessa.

First, NK cells were gated in regard to singlet, and then gated in regard to 7AAD- and CD3-CD56+. The transduction efficiency of the Her2 specific hz39D2 scFv CAR constructs was determined by flow cytometric analysis of cells expressing CAR among CD3-CD56+ cells.

Example 9: Cytotoxic Activity of Anti-Her2 CAR Constructs in NK Cells

Cells:

The human breast cancer cell line HCC1954, SKBR3 and MDA-MB 468, ovarian cancer cell line SKOV-3, gastric cancer cell line N87 and human erythroleukemic cell line K562 were obtained from the American Type Culture Collection (ATCC) (Manassas, Va., USA). HCC1954, N87, SKOV-3 and K562 were maintained in RPMI-1640 (ATCC) (Manassas, Va.) with 10% fetal bovine serum (FBS; Gibco, Grand Island, N.Y., USA). SKBR3 and MDA-MB 468 were maintained in DMEM (Gibco, Grand Island, N.Y., USA) with 10% FBS. PBMC or cord blood derived NK cells and transduced NK cells were maintained in CellGro® serum-free media+1% human plasma+500 IU/mL interleukin-2. Human embryonic kidney fibroblast 293T cells were obtained from the ATCC and maintained in DMEM (Gibco, Grand Island, N.Y., USA) supplemented with 10% FBS % (Gibco, Grand Island, N.Y., USA).

Calcein Releasing Cytotoxicity Assay:

Target cells were labeled at 37° C. for 1 hour with 30 μM calcein-acetoxymethyl ester (Calcein-AM; Molecular probes). After washing, the labeled target cells were dispensed to $1 \times 10^4$ cells per well in 96-well plates. Control or CAR transduced NK cells were harvested, washed, and then were added at different E/T (effector-to-target) ratios. After 2 hours, the plates were centrifuged at 2000 rpm for 3 minutes, and a supernatant of 100 μL was collected and subjected to measurement of calcein release using a fluorescence microplate reader (Victor3, PerkinElmer) at an excitation wavelength of 485 nm and an emission wavelength of 535 nm. Specific calcein release amount was calculated by the following equation: percent specific lysis= (test release−spontaneous release)×100/(maximal release−spontaneous release). For maximal lysis, a 1% Triton X-100 solution was used.

Comparison of CAR Constructs In Vitro Her2+ Cell Killing:

The cell killing activities of clone #2, #6 and #14 were compared against various target cells. Cord-blood derived NK (CBNK) cells were transduced with each construct using lentiviral vector system at 40 multiplicity of infection (MOI) at day 7 after culture, followed on day 11 by a positive magnetic activated cell sorting (MACS) process for HER-2-CAR-NK expressing cells. As controls, we used unmodified CBNK and mock-transduced CBNK that was transduced with lentivirus vector harboring GFP gene instead of the CAR genes. Killing assay (Calcein releasing cytotoxicity assay) was performed using HER2 positive target cancer cell lines: SKBR3 (breast cancer), HCC1954 (breast cancer, trastuzumab resistant), NCI-N87 (gastric cancer) at different ratios of effector to target cells (5:1, 2.5:1, 1:1). All of the HER-2-CAR-NKs showed higher cytotoxicity to HER-2 expressing target cells than non-transduced or mock vector transduced NK cells. Clone #14 showed unexpectedly the highest cytotoxicity to all three target cells (FIGS. 8A-8C).

The killing activity of clone #14 was further assessed by testing its cytotoxicity to various cancer cell lines: K562 (lymphoblast, HER-2 negative, but NK susceptible control), MDA-MB-468 (breast cancer, HER-2 negative), SKOV3 (ovarian cancer, HER-2 positive), NCI-N87 (gastric cancer, HER-2 positive), and trastuzumab-resistant cell line HCC1954 (breast cancer, HER-2 positive). The cytotoxicity of clone #14 was compared with unmodified CBNK at various ratios of effector to target cells (10:1, 3:1, 1:1 & 0.3:1). Clone #14 showed significantly higher and unexpected cytotoxicity against HER2 positive cancer cell lines than unmodified CBNKs. HER2-CAR-NK was also active on HCC1954 (breast cancer, HER-2 positive), which has previously seen to be resistant to trastuzumab mAb treatment (FIGS. 9A-9E).

Figures 10A, 10B:
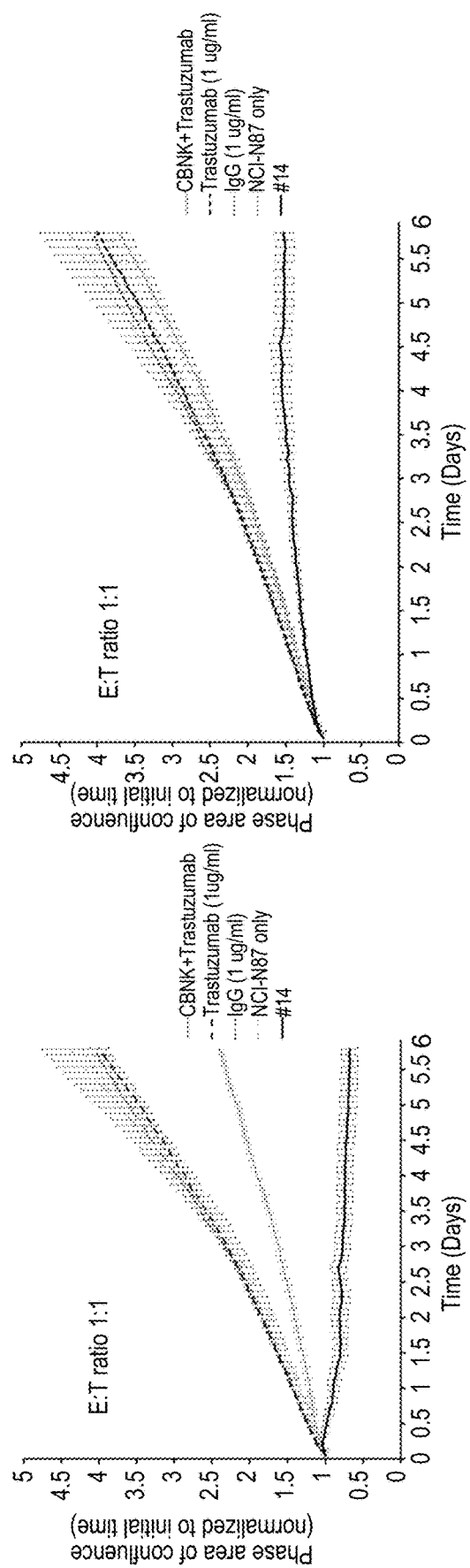
FIGS. 10A-10B are line graphs showing the long-term serial killing activity of HER2-CAR clones #6 and #14 assessed using the Incucyte live cell imaging system.

In Vitro Long-Term Her2+ Cell Killing:

The long-term serial killing activity of clones #6 & #14 was assessed using the Incucyte live cell imaging system. NCI-N87 Her2+ gastric carcinoma target cells were grown and monitored in the Incucyte system for 6 days in the presence of: control, non-specific IgG, trastuzumab (anti-Her2 monoclonal antibody), CBNK cells, CBNK cells in combination with trastuzumab, or CBNK transduced with clone #14 CAR construct. The experiment was completed at effector to the target (E:T) cellular ratios of 1:1 and 0.3:1. Unexpectedly, clone #14 killed significantly more Her2+ target cells than either CBNKs or CBNK in combination with tastuzumab for both the E:T 1:1 and 0.3:1 conditions (FIGS. 10A and 10B).

Example 10: NK Cell Activation by Anti-Her2-CAR Constructs in Response to Target Cells Intercellular Cytokine Staining (ICS) Assay for CD107a, IFN-γ, and TNF-α:

To measure intracellular cytokines and CD107a of NK cells, NK cells were co-cultured with tumor targets at 1:1 ratio for 4 h in the presence of anti-CD107a-APC (H4A3; BD Biosciences, USA), GolgiStop™ and GolgiPlug™ (BD Bioscience, USA). After 4 hours, cells were washed with BD FACS flow buffer and stained with anti-CD3-FITC, anti-CD56-APC-eFluor®780, and 7-AAD permeabilized by BD CytoFix/CytoPerm™ and then stained with anti-IFN-γ-PE (B27; BD Biosciences) and anti-TNF-α-PE-Cy7 (Mab 11; eBioscience). Stained cells were acquired on LSR Fortessa and data analysis was conducted using FlowJo software (TreeStar Inc., OR).

NK cell degranulation activity and cytotoxic cytokine expression with the various CAR constructs was evaluated by comparing intercellular expression level of CD107a & IFN-γ. Umbilical Cord blood-derived NK (CBNK) cells transduced with clone #3, clone #14 lentivirus were compared with control CBNK cells and CBNK cells with mock lentiviral transduction. NK cells expressing clone #3, clone #14 and control cells were co-cultured with target cancer cells: K562 (HER2-negative, but susceptible to NK cell), NCI-N87, SKOV3, HCC1954, MKN74 (HER-2 negative), and MDA-MB-468 (HER-2 negative) at 1:1 ratio of effector to target cells for 2 hrs, followed by FACS analysis gating CD56+/CD107a or CD56+/IFN-γ. Both clones #3 & #14 showed an increase in intercellular expression of CD107a & IFN-γ in response to HER-2 positive target cells. Unexpectedly, clone #14 showed consistently greater degranulation activity and IFN-γ expression than clone #3 (FIG. 11A and FIG. 11B).

Figure 12A:
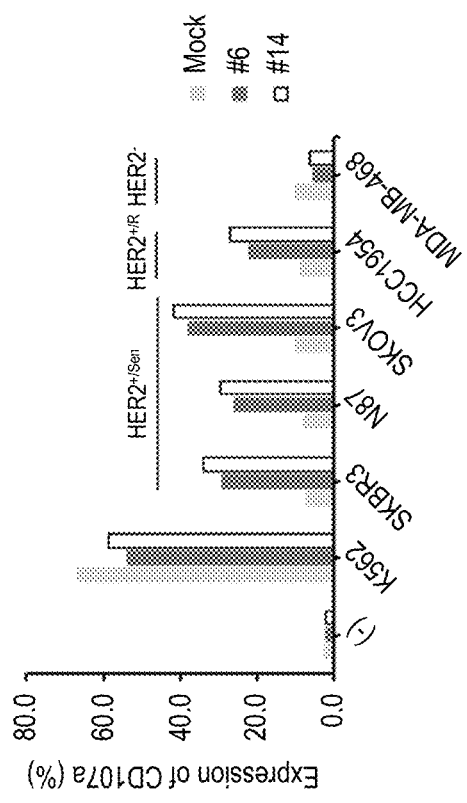
FIGS. 12A-12C are bar graphs showing NK cell degranulation activity and cytotoxic cytokine expression of HER2-CAR clones #6 and #14 evaluated by comparing intercellular expression level of CD107a, IFN-γ, and TNF-α.
Figure 12B:
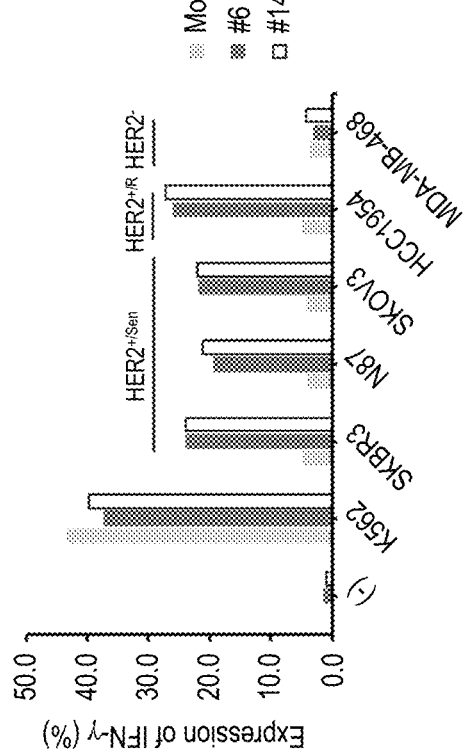
Figure 12C:
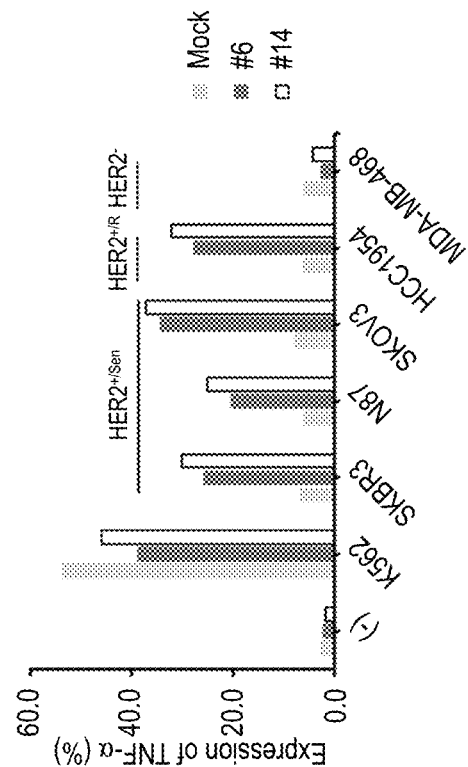

A similar assay was performed comparing Clone #6 and Clone #14 transduced CBNK cells with mock transduced CBNK cells. Again, degranulation and IFN-γ expression was unexpectedly greater in the anti-Her2 CAR transduced CBNK cells compared with control cells in response to Her2+ target cells. Further, intracellular expression of TNF-α was unexpectedly greater in the anti-Her2 CAR transduced CBNK cells compared with Control cells in response to Her2+ target cells (FIG. 12A, FIG. 12B, FIG. 12C).

Figure 13:
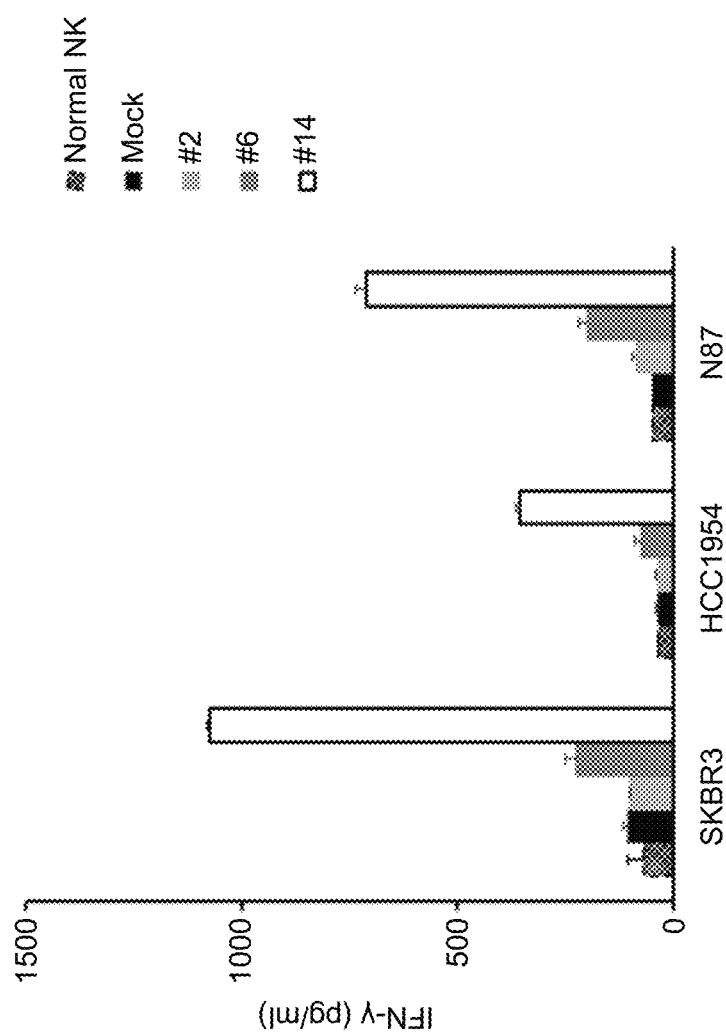
FIG. 13 is a bar graph showing the secretion of IFN-γ from anti-HER2-CAR-CBNKs (clones #2, #6, #14) when co-cultured with target cells.

IFN-γ Secretion:

The secretion of IFN-γ from anti-HER2-CAR-CBNKs (clones #2, #6, #14) was compared by co-culturing with target cells. Cell culture supernatants from the 4 hr killing assay (FIG. 8A-8C) were assayed for secreted IFN-γ using an ELISA assay. CBNK cells expressing Clone #14 unexpectedly secreted significantly more IFN-γ when co-cultured with target cancer cells than all other clones and controls. Clone #6 consistently secreted more IFN-γ in response to target cancer cells in comparison with control cells and Clone #2 (FIG. 13).

Example 11: In Vivo Anti-Tumor Activity of Anti-Her2-CAR-NK Cells

Figure 14A:
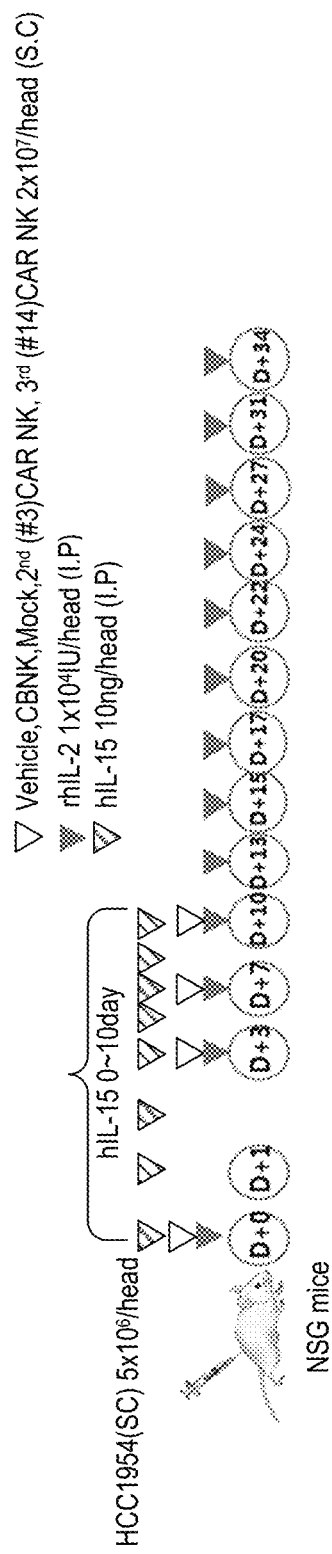
FIGS. 14A-14B are a scheme and line graph, respectively, showing the in vivo efficacy of anti-Her2-CAR clones #3 and #14 Xenograft models in NSG mice were generated by injecting $5 \times 10^6$ HCC1954 cells/mouse (HER-2 positive, trastuzumab resistant cells) subcutaneously. Tumor volume was assessed every 3-4 days after injection.
Figure 14B:
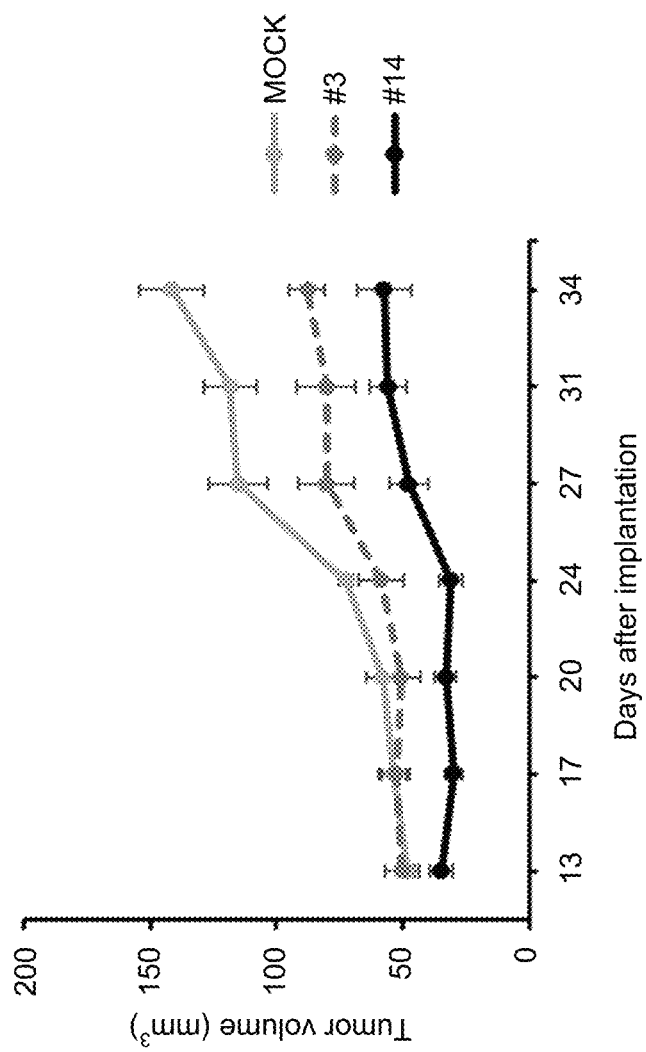

To evaluate in vivo efficacy of anti-Her2-CAR clones #3 and #14, Xenograft models in NSG mice were generated by injecting $5 \times 10^6$ HCC1954 cells/mouse (HER-2 positive, trastuzumab resistant cells) subcutaneously at Day 0. Subsequently, $2 \times 10^7$ cells of clone #3, #14, or mock-transduced CBNK were administered to the mice subcutaneously at day 0, 3, 7, 10. Additionally, Human IL-15 (10 ng/head) was intraperitoneally injected 8 times every 1-2 days up to day 10 and human IL-2 ($1 \times 10^4$ IU/head) was intraperitoneally injected 13 times every 2-4 days up to day 34. Tumor volume was assessed every 3-4 days after injection. Both clone #3 & #14 significantly suppressed tumor growth in mice on comparison with control, Mock-transduced CBNKs. Unexpectedly, clone #14 showed significantly better suppression of tumor growth than clone #3 (FIG. 14A and FIG. 14B).

Example 12: Culturing and Characterization of Anti-Her2-CAR-NK Cells

NK Cell Isolation From Umbilical Cord Blood or Peripheral Blood: CD3+ cells were removed by magnetic sorting system VarioMACS (Miltenyi Biotec, Germany) for NK cell enrichment from healthy donor derived UCB or PBMCs.

Generation of Feeder Cell Lines:

HuT 78 cells were transduced with 4-1BBL, mTNF-α, or mbIL-21 in combination. The 4-1BBL insert was prepared from 4-1BB expressing vector (Origene, USA) by PCR. OX40L was synthesized from Bioneer (South Korea). mbIL-21 was synthesized with the sequence of IL-21 active protein, CD8 signal peptide, CD8 hinge, and CD8 transmembrane and further codon optimized. cDNA of mTNF-α was prepared by reverse transcription-polymerase chain reaction (RT-PCR) from PBMCs. TNF-α converting enzyme (TACE) recognition site mutation was introduced by replacing Ala-Val (A-V) with Pro-Val (P-V) by site directed mutagenesis kit (Agilent Technologies, USA). Inserted genes and lentiviral vectors (SBI, USA) were digested by EcoRI and BamHI (New England BioLabs, USA) and ligated by In-Fusion HD cloning kit (Clontech, USA). Lentiviral concentrate was produced in 293T by lipofectamine 2000 (Thermofisher Scientific, USA) and concentrated by Amicon Ultra-15 Centrifugal Filter Unit with Ultracel-100 membrane (Merckmillipore, USA). $0.5 \times 10^6$ cells/mL HuT 78 cells were suspended in 1 mL OPTU-MEM containing 50 uL lentiviral concentrate and 10 μg/mL polybrene (Santa Cruz Biotechnology, USA) and spinoculated at 1800 g, 32° for 90 minutes. HuT 78 cells transduced with lentiviral system were selected with antibiotics. 4-1BBL/mTNF-α mbIL-21 positive HuT 78 cells were isolated by flow cytometry-guided sorting (FACSMelody™ Cell Sorter, BD bioscience, USA).

Ex Vivo Expansion and Cryopreservation of NK Cells:

CD3+ depleted cells ($1 \times 10^6$ cells/mL) were seeded in CellGro SCGM medium (CellGenix, Germany) containing 1% 2% donor-plasma, γ-irradiated (2,000 rad) eHuT 78 ($2.5 \times 10^6$ cells/mL) in CellGro SCGM medium containing 2% donor plasma, 1000 IU/mL IL-2 and 10 ng/mL anti-CD3 monoclonal antibody OKT3. Depending on culture duration, eHuT 78 cells were stimulated every 2 weeks. Cultured cells were fed with Cellgro SCGM containing 1% donor-plasma and 1000 IU/mL IL-2 (culture medium) to maintain cell concentration of $1-2 \times 10^6$ cells/mL for 14 days or 28 days. For cryopreservation of NK cells, harvested cells were suspended in freezing media and stored in a liquid nitrogen tank.

Immunostaining and Flow Cytometric Analysis:

The following monoclonal antibodies were used to stain NK cells: anti-CD56-APC-eFluor®780 (CMSSB), and anti-CD62L-PE (DREG-56) (eBioscience, USA), anti-CD3-FITC (UCHT1), anti-CD14-FITC (M5E2) anti-CD16-PE (3G8), anti-DNAM-1-PE (DX11), anti-CD25-PE (M-A251), anti-CD44-PE (515), anti-CD56-PE-Cy5 (B159), anti-CXCR3-PE(1C6/CXCR3), anti-NKp30-PE (P30-15), anti-NKp44-PE (P44-8.1), anti-NKp46-PE (9E2/NKp46) antiOX40L-PE (ik-1), anti-4-1BBL-PE (C65-485), anti-4-1BB-PE (C65-485), anti-OX40-PE (ACT35), anti-CD27-PE (MT-271), anti-CD27L-PE (Ki-24), anti-CD30-PE (BerH8), anti-CD30L-PE, anti-CD3-PE-cy5.5 (SP34-2), anti-CD4-FITC (RPA-T4) (BD Biosciences, USA), anti-NKG2A-PE (131411), anti-NKG2C-PE (134591), anti-NKG2D-PE (149810), anti-TNF-α (membrane)-PE (6401) anti-TNF-a (membrane)-PE (6401), anti-TNFRII-PE (22235) (R&D systems, USA), anti-CD30L-PE (RM153) (Biolegend, USA). Live cells were gated with 7-AAD (Beckman-Coulter, USA). T cells and HuT 78 cells were stained with anti-TcRα/β-FITC (WT31), anti-CD2-PE (RPA-2.10), anti-CD7-FITC (4H9), anti-CD11a-FITC (G43-258), anti-CD25-PE (M-A251), anti-CD28-FITC (CD28.2), anti-CD44-PE (515) and anti-CD49d-PE (9F10) (BD Bioscience, USA). e-HuT 78 cells were stained with anti-TNF-α (membrane)-PE (6401), (R&D systems, USA), anti-OX40L-PE (ik-1), anti-4-1BBL-PE (C65-485) (BD bioscience, USA), and anti-IL21-PE (3A3-N2) (eBioscience, USA). Stained cells were acquired on LSR Fortessa and data were analyzed using FlowJo software (TreeStar Inc., OR).

Figure 15A:
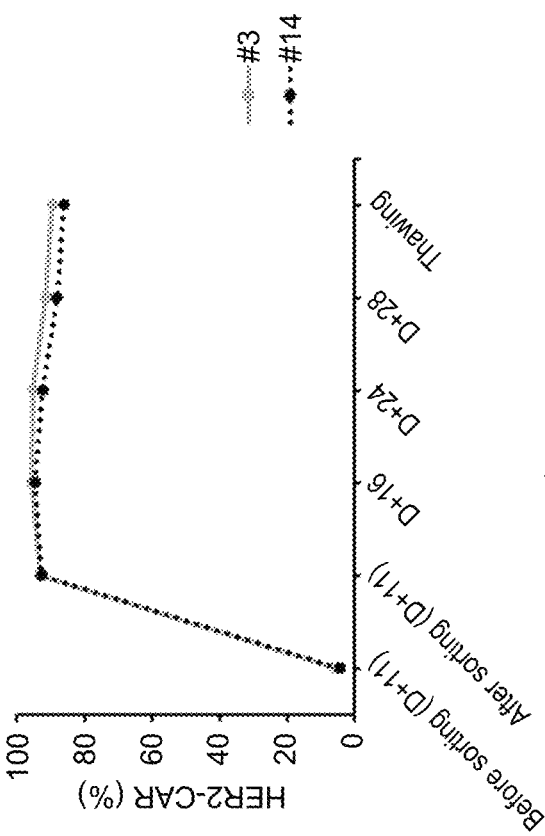
FIG. 15A is a line graph showing the proliferation of HER2-CAR-NK cells.

Comparison of Proliferation of HER2-CAR-NK Cells:

The growth of CBNK cells, mock-transduced CBNK cells, or HER-2-CAR clones #6 and #14 was compared in culture for 28 days. During the culture period, cells were stimulated with irradiated feeder cells (eHut 78) twice at day 0 & day 14. Both clone #6 and #14 showed comparable growth pattern to unmodified and mock-transduced CBNKs (FIG. 15A).

Figure 15B:
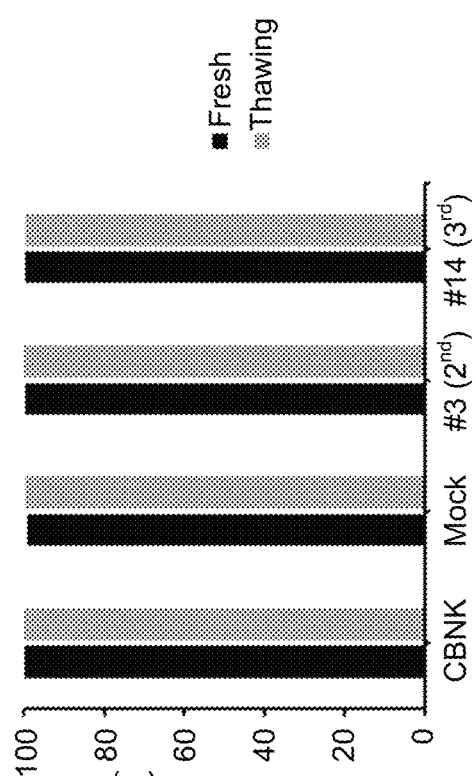
FIGS. 15B-15D are line graphs (FIG. 15B) and bar graphs (FIGS. 15C and 15D) showing the CAR expression levels, viability, and purity of HER2-CAR-NK cells during expansion, culture and cryopreservation.

Assessment of CAR Expression During Expansion, Culture, and Cryopreservation:

To assess the CAR expression level in Lentiviral transduced CBNK cells, the HER-2 CAR population was analyzed by flow cytometry at day 11, day 16, day 24, day 28 and after freezing and thawing. Both clone #6 and #14 maintained more than 80% of CAR expression up to 28 day and through freezing and thawing (FIG. 15B).

Figure 15C:
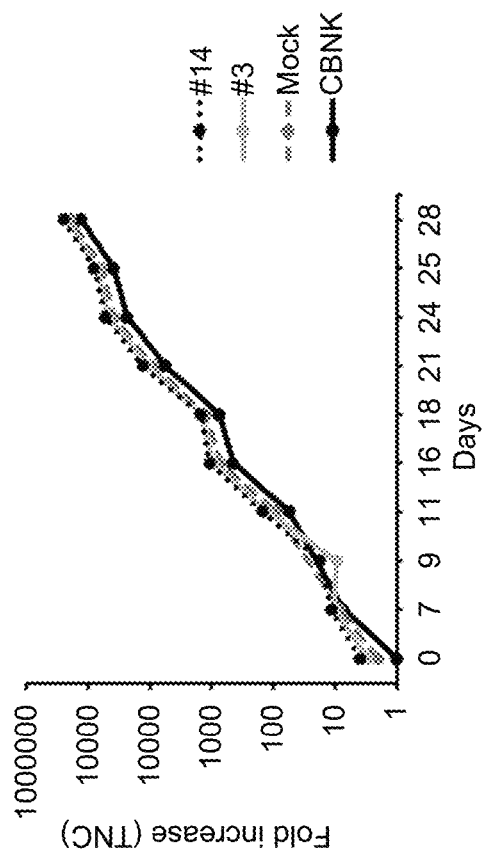
Figure 15D:
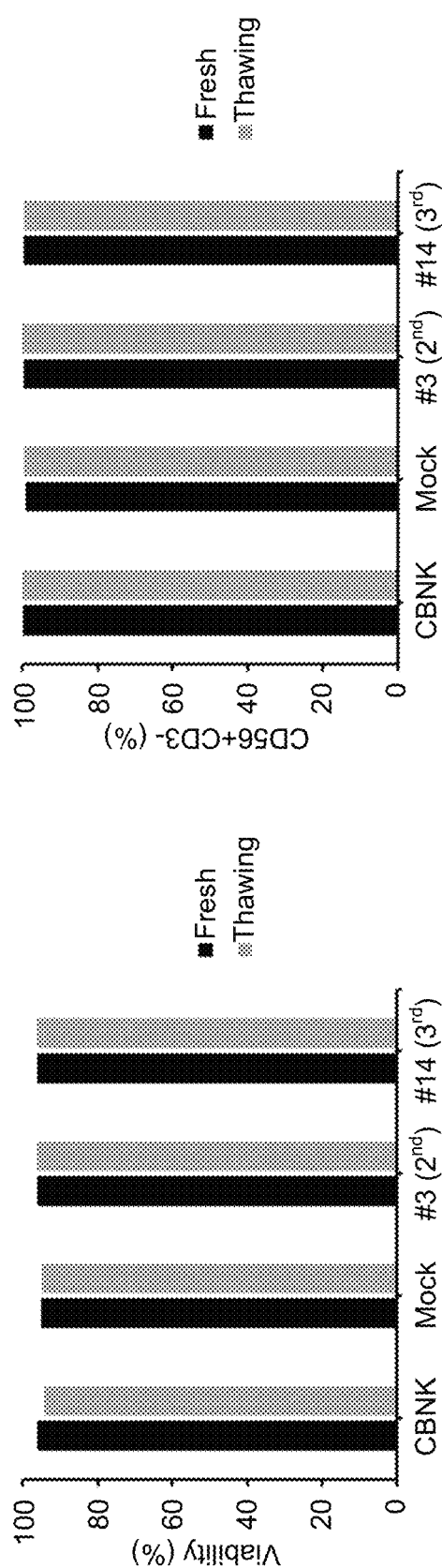

Viability of HER2-CAR-NK Cells During Expansion, Culture, and Cryopreservation:

The cell viability for HER-2CAR-NK was analyzed after 28 day-culture and freezing and thawing using propidium iodide staining-based live cell counting. Both clone #6 and #14 showed more than 95% of cell viability and no viability changes were observed in the process of freezing and thawing at 28 days after culture (FIG. 15C and FIG. 15D).

Purity of HER2-CAR-NK Cells During Expansion Culture and Cryopreservation:

The cell purity for HER-2CAR-NK was analysed after expansion culture and the freezing and thawing process using flow cytometry analysis. Counts for CD56+/CD3− cells were assessed. Both clone #6 and #14 maintained near 100% of CD56+/CD3− cell population at 28 days after culture and post the process of freezing and thawing process (FIG. 15D).

Figure 16:
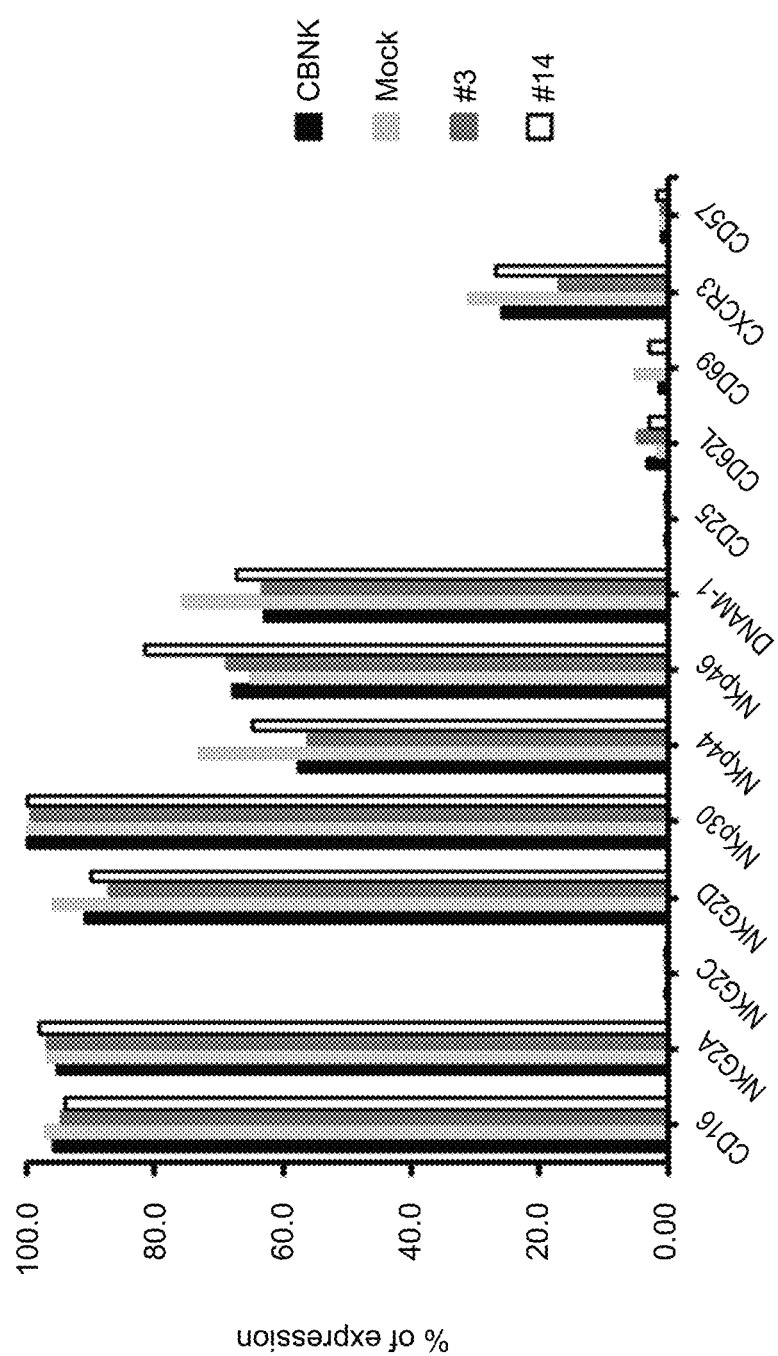
FIG. 16 is a bar graph showing the phenotypic cell surface marker expression of HER2-CAR-NK cells.

Phenotypic Cell Surface Marker Expression Analysis of HER2-CAR-NK Cells:

The expression NK cell surface markers on unmodified, mock-transduced CBNK and clone #6 and #14 was assessed by flow cytometry analysis (CD16, NKG2A, NKG2C, NKG2D, NKp30, NKp44, NKp46, CD25, CD62L, CD69, CXCR3, CD57). The expression levels of all markers tested in both HER2-CAR-NK cells expressing clones #6 and #14 were comparable to those of control NK cells (FIG. 16).

What is claimed is:

1. A method for treating a HER2 positive cancer, the method comprising:
administering to a subject in need thereof
a therapeutically effective amount of a pharmaceutical composition comprising natural killer cells expressing a chimeric antigen receptor targeting human HER2, the chimeric antigen receptor comprising an amino acid sequence comprising, from N- to C-terminus:
an extracellular antigen binding domain comprising a heavy chain variable region comprising the amino acid sequences of SEQ ID NO: 7, SEQ ID NO: 8, and SEQ ID NO: 9, and a light chain variable region comprising the amino acid sequences of SEQ ID NO: 10, SEQ ID NO: 11, and SEQ ID NO: 12;
a CD8a hinge domain;
a CD28 transmembrane domain; and
an intracellular signaling domain comprising:
(i) a CD28 intracellular signaling domain,
(ii) a OX4OL intracellular signaling domain, and
(iii) a CD3z intracellular signaling domain; and
a pharmaceutically acceptable carrier.

2. The method of claim 1, wherein the OX4OL intracellular signaling domain comprises an amino acid sequence having at least 90% sequence identity with SEQ ID NO: 127.

3. The method of claim 2, wherein the OX4OL intracellular signaling domain comprises the amino acid sequence of SEQ ID NO: 127.

4. The method of claim 1, wherein the CD3z intracellular signaling domain comprises an amino acid sequence having at least 90% sequence identity with SEQ ID NO: 121.

5. The method of claim 1, wherein the CD3z intracellular signaling domain comprises the amino acid sequence of SEQ ID NO: 121.

6. The method of claim 4, wherein the CD28 intracellular signaling domain comprises an amino acid sequence having at least 90% sequence identity with SEQ ID NO: 125.

7. The method of claim 4, wherein the CD28 intracellular signaling domain comprises the amino acid sequence of SEQ ID NO: 125.

8. The method of claim 6, wherein the CD28 transmembrane domain comprises an amino acid sequence having at least 90% sequence identity with SEQ ID NO: 119.

9. The method of claim 8, wherein the CD28 transmembrane domain comprises the amino acid sequence of SEQ ID NO: 119.

10. The method of claim 8, wherein the CD8a hinge domain comprises an amino acid sequence having at least 90% identity with SEQ ID NO: 115.

11. The method of claim 10, wherein the CD8a hinge domain comprises the amino acid sequence of SEQ ID NO: 115.

12. The method of claim 10, wherein the chimeric antigen receptor further comprises a CD8a extracellular signaling domain.

13. The method of claim 12, wherein the CD8a extracellular signaling domain comprises the amino acid sequence of SEQ ID NO: 111.

14. The method of claim 1, wherein the extracellular antigen binding domain comprises an amino acid sequence having at least 90% sequence identity to SEQ ID NO: 113.

15. The method of claim 14, wherein the extracellular antigen binding domain comprises an amino acid sequence having at least 95% sequence identity to SEQ ID NO: 113.

16. The method of claim 15, wherein the extracellular antigen binding domain comprises an amino acid sequence having at least 99% sequence identity to SEQ ID NO: 113.

17. The method of claim 16, wherein the extracellular antigen binding domain comprises the amino acid sequence of SEQ ID NO: 113.

18. The method of claim 13, wherein the chimeric antigen receptor comprises an amino acid sequence having at least 90% sequence identity to SEQ ID NO: 135.

19. The method of claim 14, wherein the chimeric antigen receptor comprises an amino acid sequence having at least 95% sequence identity to SEQ ID NO: 135.

20. The method of claim 15, wherein the chimeric antigen receptor comprises an amino acid sequence having at least 99% sequence identity to SEQ ID NO: 135.

21. The method of claim 16, wherein the chimeric antigen receptor comprises the amino acid sequence of SEQ ID NO: 135.

22. The method of claim 1, wherein the HER2 positive cancer is selected from the group consisting of breast cancer, ovarian cancer, gastric cancer, lung cancer, liver cancer, bronchial cancer, nasopharyngeal cancer, laryngeal cancer, pancreatic cancer, bladder cancer, colorectal cancer, colon cancer, cervical cancer, brain cancer, prostate cancer, bone cancer, head and neck cancer, skin cancer, thyroid cancer, parathyroid cancer and ureteral cancer.

23. The method of claim 18, wherein the HER2 positive cancer is selected from the group consisting of breast cancer, ovarian cancer, and gastric cancer.

24. The method of claim 19, wherein the HER2 positive cancer is trastuzumab resistant.

\* \* \* \* \*

SEQUENCE LISTING

```
<160> NUMBER OF SEQ ID NOS: 136

<210> SEQ ID NO 1
<211> LENGTH: 5
<212> TYPE: PRT
<213> ORGANISM: Artificial Sequence
<220> FEATURE:
<223> OTHER INFORMATION: CDRH1 of hz2G10 antibody

<400> SEQUENCE: 1

Asp Tyr Tyr Met Tyr
1               5

<210> SEQ ID NO 2
<211> LENGTH: 17
<212> TYPE: PRT
<213> ORGANISM: Artificial Sequence
<220> FEATURE:
<223> OTHER INFORMATION: CDRH2 of hz2G10 antibody

<400> SEQUENCE: 2

Tyr Ile Asn Ser Gly Gly Gly Ser Thr Tyr Tyr Pro Asp Thr Val Lys
1               5                   10                  15

Gly

<210> SEQ ID NO 3
<211> LENGTH: 12
<212> TYPE: PRT
<213> ORGANISM: Artificial Sequence
<220> FEATURE:
<223> OTHER INFORMATION: CDRH3 of hz2G10 antibody

<400> SEQUENCE: 3

Glu Ala Leu Tyr Asp Tyr Asp Tyr Ala Met Asp Tyr
1               5                   10

<210> SEQ ID NO 4
<211> LENGTH: 16
<212> TYPE: PRT
<213> ORGANISM: Artificial Sequence
<220> FEATURE:
<223> OTHER INFORMATION: CDRL1 of hz2G10 antibody
```

```
<400> SEQUENCE: 4

Lys Ser Ser Gln Ser Leu Leu Tyr Ser Asn Gly Lys Thr Tyr Leu Asn
1               5                   10                  15

<210> SEQ ID NO 5
<211> LENGTH: 7
<212> TYPE: PRT
<213> ORGANISM: Artificial Sequence
<220> FEATURE:
<223> OTHER INFORMATION: CDRL2 of hz2G10 antibody

<400> SEQUENCE: 5

Leu Val Ser Lys Leu Asp Ser
1               5

<210> SEQ ID NO 6
<211> LENGTH: 9
<212> TYPE: PRT
<213> ORGANISM: Artificial Sequence
<220> FEATURE:
<223> OTHER INFORMATION: CDRL3 of hz2G10 antibody

<400> SEQUENCE: 6

Val Gln Gly Thr His Phe Pro Leu Thr
1               5

<210> SEQ ID NO 7
<211> LENGTH: 5
<212> TYPE: PRT
<213> ORGANISM: Artificial Sequence
<220> FEATURE:
<223> OTHER INFORMATION: CDRH1 of hz39D2 antibody

<400> SEQUENCE: 7

Asn Tyr Gly Val Asn
1               5

<210> SEQ ID NO 8
<211> LENGTH: 17
<212> TYPE: PRT
<213> ORGANISM: Artificial Sequence
<220> FEATURE:
<223> OTHER INFORMATION: CDRH2 of hz39D2 antibody

<400> SEQUENCE: 8

Trp Ile Asn Thr His Thr Gly Glu Pro Thr Tyr Ala Glu Glu Phe Lys
1               5                   10                  15

Gly

<210> SEQ ID NO 9
<211> LENGTH: 9
<212> TYPE: PRT
<213> ORGANISM: Artificial Sequence
<220> FEATURE:
<223> OTHER INFORMATION: CDRH3 of hz39D2 antibody

<400> SEQUENCE: 9

Asp Asp Tyr Tyr Val Arg Val Asp Tyr
1               5

<210> SEQ ID NO 10
<211> LENGTH: 11
<212> TYPE: PRT
<213> ORGANISM: Artificial Sequence
<220> FEATURE:
```

<223> OTHER INFORMATION: CDRL1 of hz39D2 antibody

<400> SEQUENCE: 10

Lys Ala Ser Gln Asp Ile Asn Ser Tyr Leu Ser
1               5                   10

<210> SEQ ID NO 11
<211> LENGTH: 7
<212> TYPE: PRT
<213> ORGANISM: Artificial Sequence
<220> FEATURE:
<223> OTHER INFORMATION: CDRL2 of hz39D2 antibody

<400> SEQUENCE: 11

Arg Ala Asn Arg Leu Val Asp
1               5

<210> SEQ ID NO 12
<211> LENGTH: 9
<212> TYPE: PRT
<213> ORGANISM: Artificial Sequence
<220> FEATURE:
<223> OTHER INFORMATION: CDRL3 of hz39D2 antibody

<400> SEQUENCE: 12

Leu Gln Tyr Asp Glu Phe Pro Trp Thr
1               5

<210> SEQ ID NO 13
<211> LENGTH: 5
<212> TYPE: PRT
<213> ORGANISM: Artificial Sequence
<220> FEATURE:
<223> OTHER INFORMATION: CDRH1 of 24D3 antibody

<400> SEQUENCE: 13

Ser Cys Ala Met Ser
1               5

<210> SEQ ID NO 14
<211> LENGTH: 17
<212> TYPE: PRT
<213> ORGANISM: Artificial Sequence
<220> FEATURE:
<223> OTHER INFORMATION: CDRH2 of 24D3 antibody

<400> SEQUENCE: 14

Thr Ile Ser Gly Gly Gly Ser Tyr Thr Tyr Tyr Pro Asp Ser Val Lys
1               5                   10                  15

Gly

<210> SEQ ID NO 15
<211> LENGTH: 10
<212> TYPE: PRT
<213> ORGANISM: Artificial Sequence
<220> FEATURE:
<223> OTHER INFORMATION: CDRH3 of 24D3 antibody

<400> SEQUENCE: 15

His Gly Gly Tyr Glu Ser Trp Phe Pro Tyr
1               5                   10

<210> SEQ ID NO 16
<211> LENGTH: 16
<212> TYPE: PRT
<213> ORGANISM: Artificial Sequence
<220> FEATURE:
<223> OTHER INFORMATION: CDRL1 of 24D3 antibody

<400> SEQUENCE: 16

Arg Ser Ser Gln Ser Leu Val His Ser Asn Gly Asn Thr Tyr Leu His
1               5                   10                  15

<210> SEQ ID NO 17
<211> LENGTH: 7
<212> TYPE: PRT
<213> ORGANISM: Artificial Sequence
<220> FEATURE:
<223> OTHER INFORMATION: CDRL2 of 24D3 antibody

<400> SEQUENCE: 17

Lys Val Ser Asn Arg Phe Ser
1               5

<210> SEQ ID NO 18
<211> LENGTH: 10
<212> TYPE: PRT
<213> ORGANISM: Artificial Sequence
<220> FEATURE:
<223> OTHER INFORMATION: CDRL3 of 24D3 antibody

<400> SEQUENCE: 18

Ser Gln Ser Thr His Val Pro Pro Trp Thr
1               5                   10

<210> SEQ ID NO 19
<211> LENGTH: 5
<212> TYPE: PRT
<213> ORGANISM: Artificial Sequence
<220> FEATURE:
<223> OTHER INFORMATION: CDRH1 of 1G3 antibody

<400> SEQUENCE: 19

Asp Thr Tyr Met His
1               5

<210> SEQ ID NO 20
<211> LENGTH: 17
<212> TYPE: PRT
<213> ORGANISM: Artificial Sequence
<220> FEATURE:
<223> OTHER INFORMATION: CDRH2 of 1G3 antibody

<400> SEQUENCE: 20

Arg Ile Asp Pro Ala Asn Gly Tyr Thr Arg Tyr Asp Pro Asn Phe Gln
1               5                   10                  15

Gly

<210> SEQ ID NO 21
<211> LENGTH: 10
<212> TYPE: PRT
<213> ORGANISM: Artificial Sequence
<220> FEATURE:
<223> OTHER INFORMATION: CDRH3 of 1G3 antibody

<400> SEQUENCE: 21

Tyr Tyr Tyr Gly Phe Tyr Ala Met Asp Tyr
1               5                   10

<210> SEQ ID NO 22
<211> LENGTH: 11
<212> TYPE: PRT

<213> ORGANISM: Artificial Sequence
<220> FEATURE:
<223> OTHER INFORMATION: CDRL1 of 1G3 antibody

<400> SEQUENCE: 22

Lys Ala Ser Gln Asp Val Ser Thr Ala Val Ala
1               5                   10

<210> SEQ ID NO 23
<211> LENGTH: 7
<212> TYPE: PRT
<213> ORGANISM: Artificial Sequence
<220> FEATURE:
<223> OTHER INFORMATION: CDRL2 of 1G3 antibody

<400> SEQUENCE: 23

Ser Ala Ser Tyr Arg Tyr Thr
1               5

<210> SEQ ID NO 24
<211> LENGTH: 9
<212> TYPE: PRT
<213> ORGANISM: Artificial Sequence
<220> FEATURE:
<223> OTHER INFORMATION: CDRL3 of 1G3 antibody

<400> SEQUENCE: 24

Gln Gln His Tyr Ser Thr Pro Pro Thr
1               5

<210> SEQ ID NO 25
<211> LENGTH: 5
<212> TYPE: PRT
<213> ORGANISM: Artificial Sequence
<220> FEATURE:
<223> OTHER INFORMATION: CDRH1 of hz8G11 antibody

<400> SEQUENCE: 25

Gly Tyr Tyr Met His
1               5

<210> SEQ ID NO 26
<211> LENGTH: 17
<212> TYPE: PRT
<213> ORGANISM: Artificial Sequence
<220> FEATURE:
<223> OTHER INFORMATION: CDRH2 of hz8G11 antibody

<400> SEQUENCE: 26

His Ile Asn Pro Asn Asn Gly Gly Thr Ser Tyr Asn Gln Lys Phe Lys
1               5                   10                  15

Gly

<210> SEQ ID NO 27
<211> LENGTH: 6
<212> TYPE: PRT
<213> ORGANISM: Artificial Sequence
<220> FEATURE:
<223> OTHER INFORMATION: CDRH3 of hz8G11 antibody

<400> SEQUENCE: 27

Glu Glu Ala Phe Ala Tyr
1               5

<210> SEQ ID NO 28
<211> LENGTH: 11

```
<212> TYPE: PRT
<213> ORGANISM: Artificial Sequence
<220> FEATURE:
<223> OTHER INFORMATION: CDRL1 of hz8G11 antibody

<400> SEQUENCE: 28

Arg Ala Ser Gln Asp Ile Ser Asn Tyr Leu Asn
1               5                   10

<210> SEQ ID NO 29
<211> LENGTH: 7
<212> TYPE: PRT
<213> ORGANISM: Artificial Sequence
<220> FEATURE:
<223> OTHER INFORMATION: CDRL2 of hz8G11 antibody

<400> SEQUENCE: 29

Tyr Thr Ser Arg Leu His Ser
1               5

<210> SEQ ID NO 30
<211> LENGTH: 9
<212> TYPE: PRT
<213> ORGANISM: Artificial Sequence
<220> FEATURE:
<223> OTHER INFORMATION: CDRL3 of hz8G11 antibody

<400> SEQUENCE: 30

Gln Gln Gly Ile Thr Pro Pro Trp Thr
1               5

<210> SEQ ID NO 31
<211> LENGTH: 121
<212> TYPE: PRT
<213> ORGANISM: Artificial Sequence
<220> FEATURE:
<223> OTHER INFORMATION: Amino acid sequence of hz2G10 heavy chain
      variable region

<400> SEQUENCE: 31

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Leu Tyr Asp Tyr Asp Tyr Ala Met Asp Tyr Trp Gly
            100                 105                 110

Gln Gly Thr Thr Val Thr Val Ser Ser
        115                 120

<210> SEQ ID NO 32
<211> LENGTH: 363
<212> TYPE: DNA
<213> ORGANISM: Artificial Sequence
<220> FEATURE:
<223> OTHER INFORMATION: Nucleic acid sequence of hz2G10 heavy chain
      variable region
```

<400> SEQUENCE: 32

```
gaggtgcagt tggtcgagtc tggaggaggt ctggtacagc caggggggaag tctgagactg    60
agctgcgccg cttctggttt tacctttagc gattactata tgtattgggt aagacaggca   120
cctggtaaag gtttggaatg ggtggcctac ataaactcgg gcgggggcag cacctactac   180
ccggataccg tgaagggccg cttcaccatc tcccgagaca acgcgaaaaa ttcattgtat   240
ctgcaaatga actcacttag agctgaagat actgccgttt actactgcgc cagagaagca   300
ctctatgact atgattacgc tatggattac tgggggcagg gcacaaccgt cactgtttct   360
agt                                                                 363
```

<210> SEQ ID NO 33
<211> LENGTH: 451
<212> TYPE: PRT
<213> ORGANISM: Artificial Sequence
<220> FEATURE:
<223> OTHER INFORMATION: Amino acid sequence of hz2G10 heavy chain

<400> SEQUENCE: 33

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser Asp Tyr
            20                  25                  30

Tyr Met Tyr Trp Val Arg Gln Ala Pro Gly Lys Gly Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Ser Leu Tyr
65                  70                  75                  80

Leu Gln Met Asn Ser Leu Arg Ala Glu Asp Thr Ala Val Tyr Tyr Cys
                85                  90                  95

Ala Arg Glu Ala Leu Tyr Asp Tyr Asp Tyr Ala Met Asp Tyr Trp Gly
            100                 105                 110

Gln Gly Thr Thr Val Thr Val Ser Ser Ala Ser Thr Lys Gly Pro Ser
        115                 120                 125

Val Phe Pro Leu Ala Pro Ser Ser Lys Ser Thr Ser Gly Gly Thr Ala
    130                 135                 140

Ala Leu Gly Cys Leu Val Lys Asp Tyr Phe Pro Glu Pro Val Thr Val
145                 150                 155                 160

Ser Trp Asn Ser Gly Ala Leu Thr Ser Gly Val His Thr Phe Pro Ala
                165                 170                 175

Val Leu Gln Ser Ser Gly Leu Tyr Ser Leu Ser Ser Val Val Thr Val
            180                 185                 190

Pro Ser Ser Ser Leu Gly Thr Gln Thr Tyr Ile Cys Asn Val Asn His
        195                 200                 205

Lys Pro Ser Asn Thr Lys Val Asp Lys Val Glu Pro Lys Ser Cys
    210                 215                 220

Asp Lys Thr His Thr Cys Pro Pro Cys Pro Ala Pro Glu Leu Leu Gly
225                 230                 235                 240

Gly Pro Ser Val Phe Leu Phe Pro Pro Lys Pro Lys Asp Thr Leu Met
                245                 250                 255

Ile Ser Arg Thr Pro Glu Val Thr Cys Val Val Val Asp Val Ser His
            260                 265                 270
```

Glu Asp Pro Glu Val Lys Phe Asn Trp Tyr Val Asp Gly Val Glu Val
            275                 280                 285

His Asn Ala Lys Thr Lys Pro Arg Glu Glu Gln Tyr Asn Ser Thr Tyr
    290                 295                 300

Arg Val Val Ser Val Leu Thr Val Leu His Gln Asp Trp Leu Asn Gly
305                 310                 315                 320

Lys Glu Tyr Lys Cys Lys Val Ser Asn Lys Ala Leu Pro Ala Pro Ile
                325                 330                 335

Glu Lys Thr Ile Ser Lys Ala Lys Gly Gln Pro Arg Glu Pro Gln Val
            340                 345                 350

Tyr Thr Leu Pro Pro Ser Arg Asp Glu Leu Thr Lys Asn Gln Val Ser
        355                 360                 365

Leu Thr Cys Leu Val Lys Gly Phe Tyr Pro Ser Asp Ile Ala Val Glu
    370                 375                 380

Trp Glu Ser Asn Gly Gln Pro Glu Asn Asn Tyr Lys Thr Thr Pro Pro
385                 390                 395                 400

Val Leu Asp Ser Asp Gly Ser Phe Phe Leu Tyr Ser Lys Leu Thr Val
                405                 410                 415

Asp Lys Ser Arg Trp Gln Gln Gly Asn Val Phe Ser Cys Ser Val Met
            420                 425                 430

His Glu Ala Leu His Asn His Tyr Thr Gln Lys Ser Leu Ser Leu Ser
        435                 440                 445

Pro Gly Lys
    450

<210> SEQ ID NO 34
<211> LENGTH: 1353
<212> TYPE: DNA
<213> ORGANISM: Artificial Sequence
<220> FEATURE:
<223> OTHER INFORMATION: Nucleic acid sequence of hz2G10 heavy chain

<400> SEQUENCE: 34
gaggtgcagt tggtcgagtc tggaggaggt ctggtacagc caggggggaag tctgagactg      60 agctgcgccg cttctggttt tacctttagc gattactata tgtattgggt aagacaggca     120
cctggtaaag gtttggaatg ggtggcctac ataaactcgg gcgggggcag cacctactac     180
ccggataccg tgaagggccg cttcaccatc tcccgagaca cgcgaaaaa ttcattgtat     240 ctgcaaatga actcacttag agctgaagat actgccgttt actactgcgc cagagaagca     300
ctctatgact atgattacgc tatggattac tgggggcagg gcacaaccgt cactgttcct     360
agtgcctcca ccaagggccc ctccgtgttc cctctggccc cctccagcaa gtccacctct     420
ggcggcacag ccgccctggg ctgcctggtg aaagactact cccccgagcc cgtgaccgtg     480
tcctggaact ctggcgccct gaccctccggc gtgcacacct ccctgccgcgt gctgcagtcc     540 tccggcctgt actccctgtc ctccgtggtg accgtgccct ccagctctct gggcacccag     600
acctacatct gtaacgtgaa ccacaagccc tccaacacca aggtggacaa gaaggtggaa     660
cccaagtcct gcgacaagac ccacacctgt cccccctgcc ctgcccctga actgctgggc     720
ggaccttccg tgttcctgtt ccccccaaag cccaaggaca ccctgatgat ctcccggacc     780
cccgaagtga cctgcgtggt ggtggacgtg tcccacgagg accctgaagt gaagttcaat     840
tggtacgtgg acggcgtgga agtgcacaat gccaagacca gcccagaga ggaacagtac     900 aactccacct accgggtggt gtctgtgctg accgtgctgc accaggactg gctgaacggc     960

```
aaagaataca agtgcaaagt ctccaacaag ccctgcctg ccccatcga aagaccatc     1020 tccaaggcca agggccagcc cgcgagccc caggtgtaca ccctgccccc tagccgggac    1080
gagctgacca agaaccaggt gtccctgacc tgtctggtga aaggcttcta cccctccgac    1140
attgccgtgg aatgggagtc caacggccag cccgagaaca actacaagac caccccccct    1200
gtgctggact ccgacggctc attcttcctg tactccaagc tgaccgtgga caagtcccgg    1260
tggcagcagg gcaacgtgtt ctcctgctcc gtgatgcacg aggccctgca caaccactac    1320
acccagaagt ccctgtccct gagccccggc aag                                1353

<210> SEQ ID NO 35
<211> LENGTH: 112
<212> TYPE: PRT
<213> ORGANISM: Artificial Sequence
<220> FEATURE:
<223> OTHER INFORMATION: Amino acid sequence of hz2G10 light chain
      variable region

<400> SEQUENCE: 35

Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Leu Thr Phe Gly Gly Gly Thr Lys Val Glu Ile Lys
            100                 105                 110

<210> SEQ ID NO 36
<211> LENGTH: 336
<212> TYPE: DNA
<213> ORGANISM: Artificial Sequence
<220> FEATURE:
<223> OTHER INFORMATION: Nucleic acid sequence of hz2G10 light chain
      variable region

<400> SEQUENCE: 36
gacattgtca tgacgcagag cccccttca ctcagcgtga ctcccggtca gccgccagc      60 atttcctgta aaagctctca gtcgctcctg tacagcaatg gcaagactta tctgaattgg   120
ctgttacaga aaccaggcca aagccctcaa aggcttatct acctggtgag taagttagac   180
agcggggtgc ctgacagatt tagcggatct ggaagcggga ccgatttcac actaaaaatc   240
agcagggttg aggcagagga cgtgggcgtg tattattgtg tgcagggcac acacttccca   300
ctcacattcg ggggaggcac aaaggtggaa atcaag                             336

<210> SEQ ID NO 37
<211> LENGTH: 219
<212> TYPE: PRT
<213> ORGANISM: Artificial Sequence
<220> FEATURE:
<223> OTHER INFORMATION: Amino acid sequence of hz2G10 light chain
```

<400> SEQUENCE: 37

Asp Ile Val Met Thr Gln Ser Pro Leu Ser Leu Ser Val Thr Pro Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Lys Pro Gly Gln Ser
        35                  40                  45

Pro Gln Arg Leu Ile Tyr Leu Val Ser Lys Leu Asp Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Val Gly Val Tyr Tyr Cys Val Gln Gly
                85                  90                  95

Thr His Phe Pro Leu Thr Phe Gly Gly Gly Thr Lys Val Glu Ile Lys
            100                 105                 110

Arg Thr Val Ala Ala Pro Ser Val Phe Ile Phe Pro Pro Ser Asp Glu
        115                 120                 125

Gln Leu Lys Ser Gly Thr Ala Ser Val Val Cys Leu Leu Asn Asn Phe
    130                 135                 140

Tyr Pro Arg Glu Ala Lys Val Gln Trp Lys Val Asp Asn Ala Leu Gln
145                 150                 155                 160

Ser Gly Asn Ser Gln Glu Ser Val Thr Glu Gln Asp Ser Lys Asp Ser
                165                 170                 175

Thr Tyr Ser Leu Ser Ser Thr Leu Thr Leu Ser Lys Ala Asp Tyr Glu
            180                 185                 190

Lys His Lys Val Tyr Ala Cys Glu Val Thr His Gln Gly Leu Ser Ser
        195                 200                 205

Pro Val Thr Lys Ser Phe Asn Arg Gly Glu Cys
    210                 215

<210> SEQ ID NO 38
<211> LENGTH: 657
<212> TYPE: DNA
<213> ORGANISM: Artificial Sequence
<220> FEATURE:
<223> OTHER INFORMATION: Nucleic acid sequence of hz2G10 light chain

<400> SEQUENCE: 38

```
gacattgtca tgacgcagag ccccctttca ctcagcgtga ctcccggtca gcccgccagc      60
atttcctgta aaagctctca gtcgctcctg tacagcaatg gcaagactta tctgaattgg     120
ctgttacaga aaccaggcca aagccctcaa aggcttatct acctggtgag taagttagac     180
agcggggtgc ctgacagatt tagcggatct ggaagcggga ccgatttcac actaaaaatc     240
agcagggttg aggcagagga cgtgggcgtg tattattgtg tgcagggcac acacttccca     300
ctcacattcg gggaggcac aaaggtggaa atcaagcgga ccgtggccgc tcccctcgtg     360
ttcatcttcc caccctccga cgagcagctg aagtccggca ccgccagcgt ggtctgcctg     420
ctgaacaact ctaccccccg cgaggccaag gtgcagtgga aggtggacaa cgccctgcag     480
tccggcaact cccaggaatc cgtcaccgag caggactcca aggacagcac ctactccctg     540
tcctccaccc tgaccctgtc caaggccgac tacgagaagc acaaggtgta cgcctgcgaa     600
gtgacccacc agggcctgtc cagccccgtg accaagtcct tcaaccgggg cgagtgc       657
```

<210> SEQ ID NO 39

```
<211> LENGTH: 118
<212> TYPE: PRT
<213> ORGANISM: Artificial Sequence
<220> FEATURE:
<223> OTHER INFORMATION: Amino acid sequence of hz39D2 heavy chain
      variable region

<400> SEQUENCE: 39

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Asp Tyr Tyr Val Arg Val Asp Tyr Trp Gly Gln Gly Thr
            100                 105                 110

Thr Val Thr Val Ser Ser
        115

<210> SEQ ID NO 40
<211> LENGTH: 354
<212> TYPE: DNA
<213> ORGANISM: Artificial Sequence
<220> FEATURE:
<223> OTHER INFORMATION: Nucleic acid sequence of hz39D2 heavy chain
      variable region

<400> SEQUENCE: 40
caagtccaac tcgtgcagtc aggatctgaa ctgaagaaac ctggagcgag cgttaaggtt    60
tcctgcaagg ccagcggcta cgttcact   aactatggtg tcaactgggt gagacaggca   120
cccggccagg gctggagtg  gatgggttgg atcaatactc acacagggga accaacatat   180
gctgaggagt tcaaaggacg gtttgttttt agtctggaca cctccgtgtc taccgcctac   240
ctgcagattt ccagccttaa agcagaggac actgctgtat actactgtgc cagagacgat   300
tactatgtga gggtggatta ctgggggcag gggaccaccg tgacagtctc aagt         354

<210> SEQ ID NO 41
<211> LENGTH: 448
<212> TYPE: PRT
<213> ORGANISM: Artificial Sequence
<220> FEATURE:
<223> OTHER INFORMATION: Amino acid sequence of hz39D2 heavy chain

<400> SEQUENCE: 41

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60
```

```
Lys Gly Arg Phe Val Phe Ser Leu Asp Thr Ser Val Ser Thr Ala Tyr
 65                  70                  75                  80

Leu Gln Ile Ser Ser Leu Lys Ala Glu Asp Thr Ala Val Tyr Tyr Cys
                 85                  90                  95

Ala Arg Asp Asp Tyr Tyr Val Arg Val Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 42
<211> LENGTH: 1344
<212> TYPE: DNA
<213> ORGANISM: Artificial Sequence
<220> FEATURE:
```

<223> OTHER INFORMATION: Nucleic acid sequence of hz39D2 heavy chain

<400> SEQUENCE: 42

```
caagtccaac tcgtgcagtc aggatctgaa ctgaagaaac ctggagcgag cgttaaggtt      60
tcctgcaagg ccagcggcta tacgttcact aactatggtg tcaactgggt gagacaggca     120
cccggccagg gcctggagtg gatgggttgg atcaatactc acacagggga accaacatat     180
gctgaggagt tcaaaggacg gtttgttttt agtctggaca cctccgtgtc taccgcctac     240
ctgcagattt ccagccttaa agcagaggac actgctgtat actactgtgc cagagacgat     300
tactatgtga gggtggatta ctgggggcag ggaccaccg tgacagtctc aagtgcctcc      360
accaagggcc cctccgtgtt ccctctggcc ccctccagca gtccacctc tggcggcaca      420
gccgccctgg gctgcctggt gaaagactac ttccccgagc ccgtgaccgt gtcctggaac     480
tctggcgccc tgacctccgg cgtgcacacc ttccctgccg tgctgcagtc ctccggcctg     540
tactccctgt cctccgtggt gaccgtgccc tccagctctc tgggcaccca gacctacatc     600
tgtaacgtga accacaagcc ctccaacacc aaggtggaca gaaggtgga acccaagtcc      660
tgcgacaaga cccacacctg tccccctgc cctgcccctg aactgctggg cggaccttcc      720
gtgttcctgt tccccccaaa gcccaaggac accctgatga tctcccggac ccccgaagtg     780
acctgcgtgg tggtggacgt gtcccacgag accctgaag tgaagttcaa ttggtacgtg      840
gacggcgtgg aagtgcacaa tgccaagacc aagcccagag gaacagta caactccacc       900
taccgggtgg tgtctgtgct gaccgtgctg caccaggact ggctgaacgg caaagaatac     960
aagtgcaaag tctccaacaa ggccctgcct gcccccatcg aaaagaccat ctccaaggcc    1020
aagggccagc ccgcgagcc ccaggtgtac accctgcccc ctagccggga cgagctgacc      1080
aagaaccagg tgtccctgac ctgtctggtg aaaggcttct accctccga cattgccgtg     1140
gaatgggagt ccaacggcca gcccgagaac aactacaaga ccacccccc tgtgctggac     1200
tccgacggct cattcttcct gtactccaag ctgaccgtgg acaagtcccg gtggcagcag    1260
ggcaacgtgt tctcctgctc cgtgatgcac gaggccctgc acaaccacta cacccagaag    1320
tccctgtccc tgagccccgg caag                                           1344
```

<210> SEQ ID NO 43
<211> LENGTH: 107
<212> TYPE: PRT
<213> ORGANISM: Artificial Sequence
<220> FEATURE:
<223> OTHER INFORMATION: Amino acid sequence of hz39D2 light chain variable region

<400> SEQUENCE: 43

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Trp
                85                  90                  95
```

Thr Phe Gly Gln Gly Thr Lys Val Glu Ile Lys
            100                 105

<210> SEQ ID NO 44
<211> LENGTH: 321
<212> TYPE: DNA
<213> ORGANISM: Artificial Sequence
<220> FEATURE:
<223> OTHER INFORMATION: Nucleic acid sequence of hz39D2 light chain
      variable region

<400> SEQUENCE: 44
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat atactctga ccatctcctc tctgcagcct      240
gaagactttg ccacttacta ctgtctgcaa tacgatgagt tcccatggac cttcggccag     300
ggcaccaagg tggagattaa a                                                321

<210> SEQ ID NO 45
<211> LENGTH: 214
<212> TYPE: PRT
<213> ORGANISM: Artificial Sequence
<220> FEATURE:
<223> OTHER INFORMATION: Amino acid sequence of hz39D2 light chain

<400> SEQUENCE: 45

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 46
<211> LENGTH: 642
<212> TYPE: DNA
<213> ORGANISM: Artificial Sequence
<220> FEATURE:
<223> OTHER INFORMATION: Nucleic acid sequence of hz39D2 light chain

<400> SEQUENCE: 46

```
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctgcaa tacgatgagt tcccatggac cttcggccag     300
ggcaccaagg tggagattaa acggaccgtg gccgctccct ccgtgttcat cttcccaccc     360
tccgacgagc agctgaagtc cggcaccgcc agcgtggtct gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga gaagcacaag gtgtacgcct gcgaagtgac ccaccagggc     600
ctgtccagcc ccgtgaccaa gtccttcaac cggggcgagt gc                        642
```

<210> SEQ ID NO 47
<211> LENGTH: 119
<212> TYPE: PRT
<213> ORGANISM: Artificial Sequence
<220> FEATURE:
<223> OTHER INFORMATION: Amino acid sequence of 24D3 heavy chain
      variable region

<400> SEQUENCE: 47

```
Glu Val Lys Leu Val Glu Ser Gly Gly Gly Leu Val Lys Pro Gly Gly
1               5                   10                  15

Ser Leu Lys Leu Ser Cys Ala Ala Ser Gly Phe Thr Phe Ser Ser Cys
            20                  25                  30

Ala Met Ser Trp Val Arg Gln Thr Pro Glu Lys Arg Leu Glu Trp Val
        35                  40                  45

Ala Thr Ile Ser Gly Gly Gly Ser Tyr Thr Tyr Tyr Pro Asp Ser Val
    50                  55                  60

Lys Gly Arg Phe Thr Ile Ser Arg Asp Asn Ala Lys Asn Thr Leu Tyr
65                  70                  75                  80

Leu Gln Met Ser Ser Leu Arg Ser Glu Asp Thr Ala Met Tyr Tyr Cys
                85                  90                  95

Ala Arg His Gly Gly Tyr Glu Ser Trp Phe Pro Tyr Trp Gly Gln Gly
            100                 105                 110

Thr Leu Val Thr Val Ser Ala
        115
```

<210> SEQ ID NO 48
<211> LENGTH: 357
<212> TYPE: DNA
<213> ORGANISM: Artificial Sequence
<220> FEATURE:
<223> OTHER INFORMATION: Nucleic acid sequence of 24D3 heavy chain
      variable region

<400> SEQUENCE: 48

```
gaggtgaagc tggtggagtc tgggggaggc ttagtgaagc ctggagggtc cctgaaactc      60
tcctgtgcag cctctggatt cactttcagt agctgtgcca tgtcttgggt ccgccagact     120
ccggagaaga ggctggagtg ggtcgcaacc attagtggtg gtggtagtta cacctactat     180
ccagacagtg tgaaggggcg attcaccatc tccagagaca atgccaagaa caccctgtac     240
ctgcaaatga gcagtctgag gtctgaggac acggccatgt attactgtgc aagacatggc     300
gggtacgagt cctggtttcc ttactgggcc aagggactc tggtcactgt ctctgca         357
```

<210> SEQ ID NO 49
<211> LENGTH: 449
<212> TYPE: PRT
<213> ORGANISM: Artificial Sequence
<220> FEATURE:
<223> OTHER INFORMATION: Amino acid sequence of 24D3 heavy chain

<400> SEQUENCE: 49

| | | | | | | | | | | | | | | | |
|---|---|---|---|---|---|---|---|---|---|---|---|---|---|---|---|
| Glu | Val | Lys | Leu | Val | Glu | Ser | Gly | Gly | Gly | Leu | Val | Lys | Pro | Gly | Gly |
| 1 | | | | 5 | | | | | 10 | | | | | 15 | |
| Ser | Leu | Lys | Leu | Ser | Cys | Ala | Ala | Ser | Gly | Phe | Thr | Phe | Ser | Ser | Cys |
| | | | 20 | | | | | 25 | | | | | 30 | | |
| Ala | Met | Ser | Trp | Val | Arg | Gln | Thr | Pro | Glu | Lys | Arg | Leu | Glu | Trp | Val |
| | | 35 | | | | | 40 | | | | | 45 | | | |
| Ala | Thr | Ile | Ser | Gly | Gly | Gly | Ser | Tyr | Thr | Tyr | Tyr | Pro | Asp | Ser | Val |
| | 50 | | | | | 55 | | | | | 60 | | | | |
| Lys | Gly | Arg | Phe | Thr | Ile | Ser | Arg | Asp | Asn | Ala | Lys | Asn | Thr | Leu | Tyr |
| 65 | | | | | 70 | | | | | 75 | | | | | 80 |
| Leu | Gln | Met | Ser | Ser | Leu | Arg | Ser | Glu | Asp | Thr | Ala | Met | Tyr | Tyr | Cys |
| | | | | 85 | | | | | 90 | | | | | 95 | |
| Ala | Arg | His | Gly | Gly | Tyr | Glu | Ser | Trp | Phe | Pro | Tyr | Trp | Gly | Gln | Gly |
| | | | 100 | | | | | 105 | | | | | 110 | | |
| Thr | Leu | Val | Thr | Val | Ser | Ala | Ala | Ser | Thr | Lys | Gly | Pro | Ser | Val | Phe |
| | | 115 | | | | | 120 | | | | | 125 | | | |
| Pro | Leu | Ala | Pro | Ser | Ser | Lys | Ser | Thr | Ser | Gly | Gly | Thr | Ala | Ala | Leu |
| | 130 | | | | | 135 | | | | | 140 | | | | |
| Gly | Cys | Leu | Val | Lys | Asp | Tyr | Phe | Pro | Glu | Pro | Val | Thr | Val | Ser | Trp |
| 145 | | | | | 150 | | | | | 155 | | | | | 160 |
| Asn | Ser | Gly | Ala | Leu | Thr | Ser | Gly | Val | His | Thr | Phe | Pro | Ala | Val | Leu |
| | | | | 165 | | | | | 170 | | | | | 175 | |
| Gln | Ser | Ser | Gly | Leu | Tyr | Ser | Leu | Ser | Ser | Val | Val | Thr | Val | Pro | Ser |
| | | | 180 | | | | | 185 | | | | | 190 | | |
| Ser | Ser | Leu | Gly | Thr | Gln | Thr | Tyr | Ile | Cys | Asn | Val | Asn | His | Lys | Pro |
| | | 195 | | | | | 200 | | | | | 205 | | | |
| Ser | Asn | Thr | Lys | Val | Asp | Lys | Lys | Val | Glu | Pro | Lys | Ser | Cys | Asp | Lys |
| | 210 | | | | | 215 | | | | | 220 | | | | |
| Thr | His | Thr | Cys | Pro | Pro | Cys | Pro | Ala | Pro | Glu | Leu | Leu | Gly | Gly | Pro |
| 225 | | | | | 230 | | | | | 235 | | | | | 240 |
| Ser | Val | Phe | Leu | Phe | Pro | Pro | Lys | Pro | Lys | Asp | Thr | Leu | Met | Ile | Ser |
| | | | | 245 | | | | | 250 | | | | | 255 | |
| Arg | Thr | Pro | Glu | Val | Thr | Cys | Val | Val | Val | Asp | Val | Ser | His | Glu | Asp |
| | | | 260 | | | | | 265 | | | | | 270 | | |
| Pro | Glu | Val | Lys | Phe | Asn | Trp | Tyr | Val | Asp | Gly | Val | Glu | Val | His | Asn |
| | | 275 | | | | | 280 | | | | | 285 | | | |

```
Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 50
<211> LENGTH: 1347
<212> TYPE: DNA
<213> ORGANISM: Artificial Sequence
<220> FEATURE:
<223> OTHER INFORMATION: Nucleic acid sequence of 24D3 heavy chain

<400> SEQUENCE: 50
gaggtgaagc tggtggagtc tgggggaggc ttagtgaagc tggagggtc cctgaaactc      60 tcctgtgcag cctctggatt cactttcagt agctgtgcca tgtcttggt ccgccagact     120 ccggagaaga ggctggagtg gtcgcaacc attagtggtg gtggtagtta cacctactat     180
ccagacagtg tgaaggggcg attcaccatc tccagagaca tgccaagaa caccctgtac     240 ctgcaaatga gcagtctgag gtctgaggac acggccatgt attactgtgc aagacatggc     300
gggtacgagt cctggtttcc ttactggggc caagggactc tggtcactgt ctctgcagcc     360
tccaccaagg gcccctccgt gttccctctg gccccctcca gcaagtccac ctctggcggc     420
acagccgccc tgggctgcct ggtgaaagac tacttcccg agcccgtgac cgtgtcctgg     480
aactctggcg ccctgacctc cggcgtgcac accttccctg ccgtgctgca gtcctccggc     540
ctgtactccc tgtcctccgt ggtgaccgtg ccctccagct ctctgggcac ccagacctac     600
atctgtaacg tgaaccacaa gccctccaac accaaggtgg acaagaaggt ggaacccaag     660
tcctgcgaca gacccacac ctgtcccccc tgccctgccc tgaactgct gggcggacct     720 tccgtgttcc tgttccccccc aaagcccaag gacaccctga tgatctcccg gacccccgaa     780
gtgacctgcg tggtggtgga cgtgtcccac gaggaccctg aagtgaagtt caattggtac     840
gtggacggcg tggaagtgca caatgccaag accaagccca gagaggaaca gtacaactcc     900
acctaccggg tggtgtctgt gctgaccgtg ctgcaccagg actggctgaa cggcaagaa     960 tacaagtgca aagtctccaa caaggccctg cctgccccca tcgaaaagac catctccaag    1020
gccaaggggc agccccgcga gccccaggtg tacaccctgc ccctagccg ggacgagctg    1080 accaagaacc aggtgtccct gacctgtctg gtgaaaggct tctaccctc cgacattgcc    1140
```

```
gtggaatggg agtccaacgg ccagcccgag aacaactaca agaccacccc ccctgtgctg    1200
gactccgacg gctcattctt cctgtactcc aagctgaccg tggacaagtc ccggtggcag    1260
cagggcaacg tgttctcctg ctccgtgatg cacgaggccc tgcacaacca ctacacccag    1320
aagtccctgt ccctgagccc cggcaag                                        1347
```

<210> SEQ ID NO 51
<211> LENGTH: 113
<212> TYPE: PRT
<213> ORGANISM: Artificial Sequence
<220> FEATURE:
<223> OTHER INFORMATION: Amino acid sequence of 24D3 light chain
      variable region

<400> SEQUENCE: 51

```
Asp Ile Val Met Thr Gln Ser Pro Leu Ser Leu Pro Val Ser Leu Gly
1               5                   10                  15

Asp Gln Ala Ser Ile Ser Cys Arg Ser Ser Gln Ser Leu Val His Ser
            20                  25                  30

Asn Gly Asn Thr Tyr Leu His Trp Tyr Leu Gln Lys Pro Gly Gln Ser
        35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys
```

<210> SEQ ID NO 52
<211> LENGTH: 339
<212> TYPE: DNA
<213> ORGANISM: Artificial Sequence
<220> FEATURE:
<223> OTHER INFORMATION: Nucleic acid sequence of 24D3 light chain
      variable region

<400> SEQUENCE: 52

```
gatattgtga tgacccagtc tccactctcc ctgcctgtca gtcttggaga tcaagcctcc     60
atctcttgca gatctagtca gagccttgta cacagtaatg gaaacaccta tttacattgg    120
tacctgcaga agccaggcca gtctccaaag ctcctgatct acaaagtttc caaccgattt    180
tctggggttc cagacaggtt cagtggcagt ggatcaggga cagatttcac actcaagatc    240
agcagagtgg aggctgagga tctgggagtt tatttctgct ctcaaagtac acatgttcct    300
ccgtggacgt tcggtggagg gaccaagctg gaaatcaaa                           339
```

<210> SEQ ID NO 53
<211> LENGTH: 220
<212> TYPE: PRT
<213> ORGANISM: Artificial Sequence
<220> FEATURE:
<223> OTHER INFORMATION: Amino acid sequence of 24D3 light chain

<400> SEQUENCE: 53

```
Asp Ile Val Met Thr Gln Ser Pro Leu Ser Leu Pro Val Ser Leu Gly
1               5                   10                  15
```

Asp Gln Ala Ser Ile Ser Cys Arg Ser Ser Gln Ser Leu Val His Ser
        20                  25                  30

Asn Gly Asn Thr Tyr Leu His Trp Tyr Leu Gln Lys Pro Gly Gln Ser
            35                  40                  45

Pro Lys Leu Leu Ile Tyr Lys Val Ser Asn Arg Phe Ser Gly Val Pro
    50                  55                  60

Asp Arg Phe Ser Gly Ser Gly Ser Gly Thr Asp Phe Thr Leu Lys Ile
65                  70                  75                  80

Ser Arg Val Glu Ala Glu Asp Leu Gly Val Tyr Phe Cys Ser Gln Ser
                85                  90                  95

Thr His Val Pro Pro Trp Thr Phe Gly Gly Gly Thr Lys Leu Glu Ile
            100                 105                 110

Lys Arg Thr Val Ala Ala Pro Ser Val Phe Ile Phe Pro Pro Ser Asp
        115                 120                 125

Glu Gln Leu Lys Ser Gly Thr Ala Ser Val Val Cys Leu Leu Asn Asn
    130                 135                 140

Phe Tyr Pro Arg Glu Ala Lys Val Gln Trp Lys Val Asp Asn Ala Leu
145                 150                 155                 160

Gln Ser Gly Asn Ser Gln Glu Ser Val Thr Glu Gln Asp Ser Lys Asp
                165                 170                 175

Ser Thr Tyr Ser Leu Ser Ser Thr Leu Thr Leu Ser Lys Ala Asp Tyr
            180                 185                 190

Glu Lys His Lys Val Tyr Ala Cys Glu Val Thr His Gln Gly Leu Ser
        195                 200                 205

Ser Pro Val Thr Lys Ser Phe Asn Arg Gly Glu Cys
    210                 215                 220

<210> SEQ ID NO 54
<211> LENGTH: 660
<212> TYPE: DNA
<213> ORGANISM: Artificial Sequence
<220> FEATURE:
<223> OTHER INFORMATION: Nucleic acid sequence of 24D3 light chain

<400> SEQUENCE: 54
gatattgtga tgacccagtc tccactctcc ctgcctgtca gtcttggaga tcaagcctcc        60
atctcttgca gatctagtca gagccttgta cacagtaatg gaaacaccta tttacattgg       120
tacctgcaga agccaggcca gtctccaaag ctcctgatct acaaagtttc caaccgattt       180
tctggggttc cagacaggtt cagtggcagt ggatcaggga cagatttcac actcaagatc       240
agcagagtgg aggctgagga tctgggagtt tatttctgct ctcaaagtac acatgttcct       300
ccgtggacgt tcggtggagg gaccaagctg gaaatcaaac ggaccgtggc cgctccctcc       360
gtgttcatct tccacccctc cgacgagcag ctgaagtccg gcaccgccag cgtggtctgc       420
ctgctgaaca acttctaccc ccgcgaggcc aaggtgcagt ggaaggtgga caacgccctg       480
cagtccggca actcccagga atccgtcacc gagcaggact ccaaggacag cacctactcc       540
ctgtcctcca ccctgaccct gtccaaggcc gactacgaga gcacaaggt gtacgcctgc        600 gaagtgaccc accagggcct gtccagcccc gtgaccaagt ccttcaaccg gggcgagtgc       660

<210> SEQ ID NO 55
<211> LENGTH: 119
<212> TYPE: PRT
<213> ORGANISM: Artificial Sequence
<220> FEATURE:
<223> OTHER INFORMATION: Amino acid sequence of 1G3 heavy chain variable
      region

<400> SEQUENCE: 55

Glu Val Gln Leu Gln Gln Ser Gly Ala Glu Leu Val Lys Pro Gly Ala
1               5                   10                  15

Ser Val Lys Leu Ser Cys Thr Ala Ser Asp Phe Asn Ile Val Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Tyr Thr Arg Tyr Asp Pro Asn Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Tyr Tyr Gly Phe Tyr Ala Met Asp Tyr Trp Gly Gln Gly
                100                 105                 110

Thr Thr Val Thr Val Ser Ser
            115

<210> SEQ ID NO 56
<211> LENGTH: 357
<212> TYPE: DNA
<213> ORGANISM: Artificial Sequence
<220> FEATURE:
<223> OTHER INFORMATION: Nucleic acid sequence of 1G3 heavy chain
      variable region

<400> SEQUENCE: 56
gaggttcagc tgcagcagtc tggggcagag cttgtgaagc caggggcctc agtcaagttg      60
tcctgcacag cttctgactt caacattgta gacacctata tgcactgggt gaagcagagg     120
cctgaacagg gcctggagtg gattggaagg attgatcctg cgaatggtta tactagatat     180
gacccgaact tccagggcaa ggccactata acagcagaca catcctccaa cacagcctac     240
ctgcagctca gcagcctgac atctgaggac actgccgtct attactgtgc ccgttattac     300
tacggcttct atgctatgga ctactgggggt caaggaacca cggtcaccgt ctcctca       357

<210> SEQ ID NO 57
<211> LENGTH: 449
<212> TYPE: PRT
<213> ORGANISM: Artificial Sequence
<220> FEATURE:
<223> OTHER INFORMATION: Amino acid sequence of 1G3 heavy chain

<400> SEQUENCE: 57

Glu Val Gln Leu Gln Gln Ser Gly Ala Glu Leu Val Lys Pro Gly Ala
1               5                   10                  15

Ser Val Lys Leu Ser Cys Thr Ala Ser Asp Phe Asn Ile Val Asp Thr
            20                  25                  30

Tyr Met His Trp Val Lys Gln Arg Pro Glu Gln Gly Leu Glu Trp Ile
        35                  40                  45

Gly Arg Ile Asp Pro Ala Asn Gly Tyr Thr Arg Tyr Asp Pro Asn Phe
    50                  55                  60

Gln Gly Lys Ala Thr Ile Thr Ala Asp Thr Ser Ser Asn Thr Ala Tyr
65                  70                  75                  80

Leu Gln Leu Ser Ser Leu Thr Ser Glu Asp Thr Ala Val Tyr Tyr Cys
                85                  90                  95

Ala Arg Tyr Tyr Tyr Gly Phe Tyr Ala Met Asp Tyr Trp Gly Gln Gly
            100                 105                 110

Thr Thr Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Asp Glu Leu Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys

<210> SEQ ID NO 58
<211> LENGTH: 1347
<212> TYPE: DNA
<213> ORGANISM: Artificial Sequence
<220> FEATURE:
<223> OTHER INFORMATION: Nucleic acid sequence of 1G3 heavy chain

<400> SEQUENCE: 58

```
gaggttcagc tgcagcagtc tggggcagag cttgtgaagc caggggcctc agtcaagttg      60
tcctgcacag cttctgactt caacattgta gacacctata tgcactgggt gaagcagagg     120
cctgaacagg gcctggagtg gattggaagg attgatcctg cgaatggtta tactagatat     180
gaccccgaact tccagggcaa ggccactata acagcagaca catcctccaa cacagcctac    240
ctgcagctca gcagcctgac atctgaggac actgccgtct attactgtgc ccgttattac    300
tacggcttct atgctatgga ctactggggt caaggaacca cggtcaccgt ctcctcagcc    360
tccaccaagg gcccctccgt gttccctctg gccccctcca gcaagtccac ctctggcggc    420
acagccgccc tgggctgcct ggtgaaagac tacttccccg agcccgtgac cgtgtcctgg    480
aactctggcg ccctgacctc cggcgtgcac accttccctg ccgtgctgca gtcctccggc    540
ctgtactccc tgtcctccgt ggtgaccgtg ccctccagct ctctgggcac ccagacctac    600
atctgtaacg tgaaccacaa gcctccaac accaaggtgg acaagaaggt ggaacccaag    660
tcctgcgaca gacccacac ctgtcccccc tgccctgccc ctgaactgct gggcggacct     720
tccgtgttcc tgttcccccc aaagcccaag gacaccctga tgatctcccg gacccccgaa    780
gtgacctgcg tggtggtgga cgtgtcccac gaggaccctg aagtgaagtt caattggtac    840
gtggacggcg tggaagtgca caatgccaag accaagccca gagaggaaca gtacaactcc    900
acctaccggg tggtgtctgt gctgaccgtg ctgcaccagg actggctgaa cggcaaagaa    960
tacaagtgca aagtctccaa caaggccctg cctgcccccca tcgaaaagac catctccaag   1020
gccaagggcc agccccgcga gccccaggtg tacaccctgc cccctagccg ggacgagctg   1080
accaagaacc aggtgtccct gacctgtctg gtgaaaggct cttacccctc cgacattgcc   1140
gtggaatggg agtccaacgg ccagcccgag aacaactaca agaccacccc ccctgtgctg   1200
gactccgacg gctcattctt cctgtactcc aagctgaccg tggacaagtc ccggtggcag   1260
cagggcaacg tgttctcctg ctccgtgatg cacgaggccc tgcacaacca ctacacccag   1320
aagtccctgt ccctgagccc cggcaag                                        1347
```

<210> SEQ ID NO 59
<211> LENGTH: 107
<212> TYPE: PRT
<213> ORGANISM: Artificial Sequence
<220> FEATURE:
<223> OTHER INFORMATION: Amino acid sequence of 1G3 light chain variable region

<400> SEQUENCE: 59

```
Asp Ile Val Met Thr Gln Ser His Lys Phe Met Ser Thr Ser Val Gly
  1               5                  10                  15

Asp Arg Val Ser Ile Thr Cys Lys Ala Ser Gln Asp Val Ser Thr Ala
             20                  25                  30

Val Ala Trp Tyr Gln Gln Lys Pro Gly Gln Ser Pro Lys Leu Leu Ile
         35                  40                  45

Tyr Ser Ala Ser Tyr Arg Tyr Thr Gly Val Pro Asp Arg Phe Thr Gly
     50                  55                  60

Ser Gly Ser Gly Thr Asp Phe Thr Phe Thr Ile Ser Ser Val Gln Ala
 65                  70                  75                  80

Glu Asp Leu Ala Val Tyr Tyr Cys Gln Gln His Tyr Ser Thr Pro Pro
                 85                  90                  95
```

Thr Phe Gly Gly Gly Thr Lys Leu Glu Leu Lys
            100                 105

<210> SEQ ID NO 60
<211> LENGTH: 321
<212> TYPE: DNA
<213> ORGANISM: Artificial Sequence
<220> FEATURE:
<223> OTHER INFORMATION: Nucleic acid sequence of 1G3 light chain
      variable region

<400> SEQUENCE: 60
gatattgtga tgacgcagtc tcacaaattc atgtccacat cagtaggaga cagggtcagc    60
atcacctgca aggccagtca ggatgtgagt actgctgtag cctggtatca acagaaacca   120
ggacaatctc ctaaactact gatttactcg gcatcctacc ggtacactgg agtccctgat   180
cgcttcactg gcagtggatc tgggacggat ttcactttca ccatcagcag tgtgcaggct   240
gaagacctgg cagtttatta ctgtcagcaa cattatagta ctcctcccac gttcggaggg   300
gggaccaagc tggagctgaa a                                              321

<210> SEQ ID NO 61
<211> LENGTH: 214
<212> TYPE: PRT
<213> ORGANISM: Artificial Sequence
<220> FEATURE:
<223> OTHER INFORMATION: Amino acid sequence of 1G3 light chain

<400> SEQUENCE: 61

Asp Ile Val Met Thr Gln Ser His Lys Phe Met Ser Thr Ser Val Gly
1               5                   10                  15

Asp Arg Val Ser Ile Thr Cys Lys Ala Ser Gln Asp Val Ser Thr Ala
            20                  25                  30

Val Ala Trp Tyr Gln Gln Lys Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln His Tyr Ser Thr Pro Pro
                85                  90                  95

Thr Phe Gly Gly Gly Thr Lys Leu Glu Leu Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 62
<211> LENGTH: 642
<212> TYPE: DNA
<213> ORGANISM: Artificial Sequence
<220> FEATURE:
<223> OTHER INFORMATION: Nucleic acid sequence of 1G3 light chain

<400> SEQUENCE: 62

| | | |
|---|---|---|
| gatattgtga tgacgcagtc tcacaaattc atgtccacat cagtaggaga cagggtcagc | 60 |
| atcacctgca aggccagtca ggatgtgagt actgctgtag cctggtatca acagaaacca | 120 |
| ggacaatctc ctaaactact gatttactcg gcatcctacc ggtacactgg agtccctgat | 180 |
| cgcttcactg gcagtggatc tgggacggat ttcactttca ccatcagcag tgtgcaggct | 240 |
| gaagacctgg cagtttatta ctgtcagcaa cattatagta ctcctcccac gttcggaggg | 300 |
| gggaccaagc tggagctgaa acggaccgtg gccgctccct ccgtgttcat cttcccaccc | 360 |
| tccgacgagc agctgaagtc cggcaccgcc agcgtggtct gcctgctgaa caacttctac | 420 |
| ccccgcgagg ccaaggtgca gtggaaggtg gacaacgccc tgcagtccgg caactcccag | 480 |
| gaatccgtca ccgagcagga ctccaaggac agcacctact ccctgtcctc caccctgacc | 540 |
| ctgtccaagg ccgactacga aagcacaag gtgtacgcct gcgaagtgac ccaccagggc | 600 |
| ctgtccagcc ccgtgaccaa gtccttcaac cggggcgagt gc | 642 |

<210> SEQ ID NO 63
<211> LENGTH: 115
<212> TYPE: PRT
<213> ORGANISM: Artificial Sequence
<220> FEATURE:
<223> OTHER INFORMATION: Amino acid sequence of hz8G11 heavy chain
      variable region

<400> SEQUENCE: 63

Gln Val Gln Leu Val Gln Ser Gly Gln Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly His Ile Asn Pro Asn Asn Gly Gly Thr Ser Tyr Asn Gln Lys Phe
    50                  55                  60

Lys Gly Arg Thr Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Glu Ala Phe Ala Tyr Trp Gly Gln Gly Thr Leu Val Thr
            100                 105                 110

Val Ser Ser
        115

<210> SEQ ID NO 64
<211> LENGTH: 345
<212> TYPE: DNA
<213> ORGANISM: Artificial Sequence
<220> FEATURE:
<223> OTHER INFORMATION: Nucleic acid sequence of hz8G11 heavy chain
      variable region

<400> SEQUENCE: 64

```
caggtacagc tagtgcagag cggccaggaa gtaaagaagc caggcgcctc tgttaaggtg    60
tcatgtaagg ccagcggtta cagcttcact ggctattaca tgcactgggt ccggcaggca   120
cccggacaag ggctggaatg gataggtcac attaatccaa acaatggcgg taccagttat   180
aaccagaaat ttaaggggag gacaaccctg acagttgata atccatcag tacagcatat   240
atggagctca gcagactgag aagcgacgat actgctgtgt actactgcgc gcgggaggag   300
gctttcgcct actggggcca aggaccttta gtgactgtct catca                   345
```

<210> SEQ ID NO 65
<211> LENGTH: 445
<212> TYPE: PRT
<213> ORGANISM: Artificial Sequence
<220> FEATURE:
<223> OTHER INFORMATION: Amino acid sequence of hz8G11 heavy chain

<400> SEQUENCE: 65

```
Gln Val Gln Leu Val Gln Ser Gly Gln Glu Val Lys Lys Pro Gly Ala
1               5                   10                  15

Ser Val Lys Val Ser Cys Lys Ala Ser Gly Tyr Ser Phe Thr Gly Tyr
            20                  25                  30

Tyr Met His Trp Val Arg Gln Ala Pro Gly Gln Gly Leu Glu Trp Ile
        35                  40                  45

Gly His Ile Asn Pro Asn Asn Gly Gly Thr Ser Tyr Asn Gln Lys Phe
    50                  55                  60

Lys Gly Arg Thr Thr Leu Thr Val Asp Lys Ser Ile Ser Thr Ala Tyr
65                  70                  75                  80

Met Glu Leu Ser Arg Leu Arg Ser Asp Asp Thr Ala Val Tyr Tyr Cys
                85                  90                  95

Ala Arg Glu Glu Ala Phe Ala Tyr Trp Gly Gln Gly Thr Leu Val Thr
            100                 105                 110

Val Ser Ser Ala Ser Thr Lys Gly Pro Ser Val Phe Pro Leu Ala Pro
        115                 120                 125

Ser Ser Lys Ser Thr Ser Gly Gly Thr Ala Ala Leu Gly Cys Leu Val
    130                 135                 140

Lys Asp Tyr Phe Pro Glu Pro Val Thr Val Ser Trp Asn Ser Gly Ala
145                 150                 155                 160

Leu Thr Ser Gly Val His Thr Phe Pro Ala Val Leu Gln Ser Ser Gly
                165                 170                 175

Leu Tyr Ser Leu Ser Ser Val Val Thr Val Pro Ser Ser Ser Leu Gly
            180                 185                 190

Thr Gln Thr Tyr Ile Cys Asn Val Asn His Lys Pro Ser Asn Thr Lys
        195                 200                 205

Val Asp Lys Lys Val Glu Pro Lys Ser Cys Asp Lys Thr His Thr Cys
    210                 215                 220

Pro Pro Cys Pro Ala Pro Glu Leu Leu Gly Gly Pro Ser Val Phe Leu
225                 230                 235                 240

Phe Pro Pro Lys Pro Lys Asp Thr Leu Met Ile Ser Arg Thr Pro Glu
                245                 250                 255

Val Thr Cys Val Val Val Asp Val Ser His Glu Asp Pro Glu Val Lys
            260                 265                 270

Phe Asn Trp Tyr Val Asp Gly Val Glu Val His Asn Ala Lys Thr Lys
        275                 280                 285
```

```
Pro Arg Glu Glu Gln Tyr Asn Ser Thr Tyr Arg Val Val Ser Val Leu
    290                 295                 300
Thr Val Leu His Gln Asp Trp Leu Asn Gly Lys Glu Tyr Lys Cys Lys
305                 310                 315                 320
Val Ser Asn Lys Ala Leu Pro Ala Pro Ile Glu Lys Thr Ile Ser Lys
                325                 330                 335
Ala Lys Gly Gln Pro Arg Glu Pro Gln Val Tyr Thr Leu Pro Pro Ser
            340                 345                 350
Arg Asp Glu Leu Thr Lys Asn Gln Val Ser Leu Thr Cys Leu Val Lys
        355                 360                 365
Gly Phe Tyr Pro Ser Asp Ile Ala Val Glu Trp Glu Ser Asn Gly Gln
370                 375                 380
Pro Glu Asn Asn Tyr Lys Thr Thr Pro Pro Val Leu Asp Ser Asp Gly
385                 390                 395                 400
Ser Phe Phe Leu Tyr Ser Lys Leu Thr Val Asp Lys Ser Arg Trp Gln
                405                 410                 415
Gln Gly Asn Val Phe Ser Cys Ser Val Met His Glu Ala Leu His Asn
            420                 425                 430
His Tyr Thr Gln Lys Ser Leu Ser Leu Ser Pro Gly Lys
        435                 440                 445
```

<210> SEQ ID NO 66
<211> LENGTH: 1335
<212> TYPE: DNA
<213> ORGANISM: Artificial Sequence
<220> FEATURE:
<223> OTHER INFORMATION: Nucleic acid sequence of hz8G11 heavy chain

<400> SEQUENCE: 66

```
caggtacagc tagtgcagag cggccaggaa gtaaagaagc caggcgcctc tgttaaggtg      60
tcatgtaagg ccagcggtta cagcttcact ggctattaca tgcactgggt ccggcaggca     120
cccggacaag gctggaatg gataggtcac attaatccaa acaatggcgg taccagttat      180
aaccagaaat ttaaggggag acaaccctg acagttgata atccatcag tacagcatat       240
atggagctca gcagactgag aagcgacgat actgctgtgt actactgcgc gcggaggag      300
gctttcgcct actggggcca aggaccttta gtgactgtct catcagcctc caccaagggc     360
ccctccgtgt tccctctggc ccctccagc aagtccacct tggcggcac agccgccctg       420
ggctgcctgg tgaaagacta cttccccgag cccgtgaccg tgtcctggaa ctctggcgcc     480
ctgacctccg gcgtgcacac cttcctgcc gtgctgcagt cctccggcct gtactccctg      540
tcctccgtgg tgaccgtgcc ctccagctct ctgggcaccc agacctacat ctgtaacgtg     600
aaccacaagc cctccaacac caaggtggac aagaaggtgg aacccaagtc ctgcgacaag     660
acccacacct gtcccccctg ccctgccct gaactgctgg gcggaccttc cgtgttcctg      720
ttccccccaa agcccaagga caccctgatg atctcccgga ccccccgaagt gacctgcgtg    780
gtggtggacg tgtcccacga ggaccctgaa gtgaagttca attggtacgt ggacggcgtg    840
gaagtgcaca atgccaagac caagcccaga gaggaacagt acaactccac ctaccgggtg     900
gtgtctgtgc tgaccgtgct gcaccaggac tggctgaacg gcaagaata caagtgcaaa     960
gtctccaaca aggccctgcc tgcccccatc gaaaagacca tctccaaggc caagggccag    1020
ccccgcgagc cccaggtgta cacctgccc ctagccggg acgagctgac caagaaccag      1080
gtgtccctga cctgtctggt gaaaggcttc taccctccg acattgccgt ggaatggag      1140
tccaacggcc agcccgagaa caactacaag accacccccc ctgtgctgga ctccgacggc    1200
```

```
tcattcttcc tgtactccaa gctgaccgtg acaagtccc ggtggcagca gggcaacgtg    1260
ttctcctgct ccgtgatgca cgaggccctg cacaaccact acacccagaa gtccctgtcc    1320
ctgagccccg gcaag                                                      1335
```

<210> SEQ ID NO 67
<211> LENGTH: 107
<212> TYPE: PRT
<213> ORGANISM: Artificial Sequence
<220> FEATURE:
<223> OTHER INFORMATION: Amino acid sequence of hz8G11 light chain
      variable region

<400> SEQUENCE: 67

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30

Leu Asn Trp Tyr Gln Gln Lys Pro Gly Lys Ala Pro Lys Leu Leu Ile
        35                  40                  45

Tyr Tyr Thr Ser Arg Leu His Ser Gly Val Pro Ser Arg Phe Ser Gly
    50                  55                  60

Ser Gly Ser Gly Thr Asp Phe Ser Leu Thr Ile Ser Ser Leu Gln Pro
65                  70                  75                  80

Glu Asp Ile Ala Thr Tyr Tyr Cys Gln Gln Gly Ile Thr Pro Pro Trp
                85                  90                  95

Thr Phe Gly Gly Gly Thr Lys Val Glu Ile Lys
            100                 105
```

<210> SEQ ID NO 68
<211> LENGTH: 321
<212> TYPE: DNA
<213> ORGANISM: Artificial Sequence
<220> FEATURE:
<223> OTHER INFORMATION: Nucleic acid sequence of hz8G11 light chain
      variable region

<400> SEQUENCE: 68

```
gacatacaga tgacgcagag ccctagttca ctgtctgcct ccgtcggcga cagagtgacg     60
atcagctgcc gagccagcca agatattagt aactacctca attggtacca gcagaaacct    120
ggaaaagcac ccaagctttt gatctattac accagcaggc tgcatagcgg agtgccgagc    180 agatttcgg gttctggcag cggcaccgat ttctctctga ctatcagtag cctgcaaccc     240
gaagacattg ctacatatta ttgtcagcag ggaatcaccc ctccatggac atttggaggg    300
ggaacaaagg tggagattaa a                                              321
```

<210> SEQ ID NO 69
<211> LENGTH: 214
<212> TYPE: PRT
<213> ORGANISM: Artificial Sequence
<220> FEATURE:
<223> OTHER INFORMATION: Amino acid sequence of hz8G11 light chain

<400> SEQUENCE: 69

```
Asp Ile Gln Met Thr Gln Ser Pro Ser Ser Leu Ser Ala Ser Val Gly
1               5                   10                  15

Asp Arg Val Thr Ile Ser Cys Arg Ala Ser Gln Asp Ile Ser Asn Tyr
            20                  25                  30
```

Leu Asn Trp Tyr Gln Gln Lys Pro Gly Lys Ala Pro Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Ser Leu Thr Ile Ser Ser Leu Gln Pro
65                  70                  75                  80

Glu Asp Ile Ala Thr Tyr Tyr Cys Gln Gln Gly Ile Thr Pro Pro Trp
                85                  90                  95

Thr Phe Gly Gly Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
            130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
    210

<210> SEQ ID NO 70
<211> LENGTH: 642
<212> TYPE: DNA
<213> ORGANISM: Artificial Sequence
<220> FEATURE:
<223> OTHER INFORMATION: Nucleic acid sequence of hz8G11 light chain

<400> SEQUENCE: 70
gacatacaga tgacgcagag ccctagttca ctgtctgcct ccgtcggcga cagagtgacg      60
atcagctgcc gagccagcca agatattagt aactacctca attggtacca gcagaaacct     120
ggaaaagcac ccaagctttt gatctattac accagcaggc tgcatagcgg agtgccgagc     180 agatttcgg gttctggcag cggcaccgat ttctctctga ctatcagtag cctgcaaccc      240
gaagacattg ctacatatta ttgtcagcag ggaatcaccc ctccatggac atttggaggg     300
ggaacaaagg tggagattaa acggaccgtg gccgctccct ccgtgttcat cttcccaccc     360
tccgacgagc agctgaagtc cggcaccgcc agcgtggtct gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga gaagcacaag gtgtacgcct gcgaagtgac ccaccagggc     600
ctgtccagcc ccgtgaccaa gtccttcaac cggggcgagt gc                       642

<210> SEQ ID NO 71
<211> LENGTH: 9
<212> TYPE: PRT
<213> ORGANISM: Artificial Sequence
<220> FEATURE:
<223> OTHER INFORMATION: CDRH3 of hz39D2.14 antibody

```
<400> SEQUENCE: 71

Asp Glu Tyr Tyr Val Arg Thr Asp Tyr
1               5

<210> SEQ ID NO 72
<211> LENGTH: 9
<212> TYPE: PRT
<213> ORGANISM: Artificial Sequence
<220> FEATURE:
<223> OTHER INFORMATION: CDRH3 of hz39D2.22 and hz39D2.23 antibody

<400> SEQUENCE: 72

Asp Glu Tyr Tyr Val Arg Val Asp Tyr
1               5

<210> SEQ ID NO 73
<211> LENGTH: 9
<212> TYPE: PRT
<213> ORGANISM: Artificial Sequence
<220> FEATURE:
<223> OTHER INFORMATION: CDRL3 of hz39D2.22 antibody

<400> SEQUENCE: 73

Leu Glu Leu Asp Glu Phe Pro Trp Thr
1               5

<210> SEQ ID NO 74
<211> LENGTH: 9
<212> TYPE: PRT
<213> ORGANISM: Artificial Sequence
<220> FEATURE:
<223> OTHER INFORMATION: CDRL3 of hz39D2.23 antibody

<400> SEQUENCE: 74

Leu Gln Leu Asp Glu Phe Pro Trp Thr
1               5

<210> SEQ ID NO 75
<211> LENGTH: 121
<212> TYPE: PRT
<213> ORGANISM: Artificial Sequence
<220> FEATURE:
<223> OTHER INFORMATION: Amino acid sequence of 2G10 heavy chain
      variable region

<400> SEQUENCE: 75

Glu Val Lys Leu Leu Glu Ser Gly Gly Gly Leu Val Gln Pro Gly Gly
1               5                   10                  15

Ser Leu Lys Leu Ser Cys Ala Thr Ser Gly Phe Thr Phe Ser Asp Tyr
            20                  25                  30

Tyr Met Tyr Trp Val Arg Gln Thr Pro Glu Met Arg Leu Glu Trp Val
        35                  40                  45

Ala Tyr Ile Asn Ser Gly Gly Gly Ser Thr Tyr Tyr Pro Asp Thr Val
    50                  55                  60

Lys Gly Arg Phe Thr Ile Ser Arg Asp Asn Ala Lys Asn Thr Leu Tyr
65                  70                  75                  80

Leu Gln Met Ser Arg Leu Lys Ser Glu Asp Thr Ala Met Tyr Tyr Cys
                85                  90                  95

Ala Arg Glu Ala Leu Tyr Asp Tyr Asp Tyr Ala Met Asp Tyr Trp Gly
            100                 105                 110

Gln Gly Thr Thr Val Thr Val Ser Ser
        115                 120
```

<210> SEQ ID NO 76
<211> LENGTH: 363
<212> TYPE: DNA
<213> ORGANISM: Artificial Sequence
<220> FEATURE:
<223> OTHER INFORMATION: Nucleic acid sequence of 2G10 heavy chain
    variable region

<400> SEQUENCE: 76

```
gaggtgaagc ttctcgagtc tgggggaggc ttagtgcagc ctggagggtc cctgaaactc      60
tcctgtgcaa cctctggatt cactttcagt gactattaca tgtattgggt tcgccagact     120
ccagagatga ggctggagtg ggtcgcatat attaatagtg gtggtggtag cacctattat     180
ccagacactg taaagggccg attcaccatc tccagagaca atgccaagaa caccctgtac     240
ctgcaaatga gccgtctgaa gtctgaggac acagccatgt attactgtgc aagagaggcc     300
ctctatgatt acgactatgc tatggactac tggggtcaag gaaccacggt caccgtctcc     360
tca                                                                   363
```

<210> SEQ ID NO 77
<211> LENGTH: 112
<212> TYPE: PRT
<213> ORGANISM: Artificial Sequence
<220> FEATURE:
<223> OTHER INFORMATION: Amino acid sequence of 2G10 light chain
    variable region

<400> SEQUENCE: 77

Asp Ile Val Met Thr Gln Ser Pro Leu Thr Leu Ser Val Thr Ile Gly
1               5                   10                  15

Gln Pro Ala Ser Ile Ser Cys Lys Ser Ser Gln Ser Leu Leu Tyr Ser
            20                  25                  30

Asn Gly Lys Thr Tyr Leu Asn Trp Leu Leu Gln Arg Pro Gly Gln Ser
        35                  40                  45

Pro Lys Arg Leu Ile Tyr Leu Val Ser Lys Leu Asp Ser Gly Val Pro
    50                  55                  60

Asp Arg Phe Thr Gly Ser Gly Ser Gly Thr Asp Phe Thr Leu Lys Ile
65                  70                  75                  80

Ser Arg Val Glu Ala Glu Asp Leu Gly Val Tyr Tyr Cys Val Gln Gly
                85                  90                  95

Thr His Phe Pro Leu Thr Phe Gly Ala Gly Thr Lys Leu Glu Leu Lys
            100                 105                 110

<210> SEQ ID NO 78
<211> LENGTH: 336
<212> TYPE: DNA
<213> ORGANISM: Artificial Sequence
<220> FEATURE:
<223> OTHER INFORMATION: Nucleic acid sequence of 2G10 light chain
    variable region

<400> SEQUENCE: 78

```
gatattgtga tgacccagtc tccactcact ttgtcggtta ccattggaca accagcctct      60
atctcttgca agtcaagtca gagcctctta tatagtaatg gaaaaaccta tttgaattgg     120
ttattacaga ggccaggcca gtctccaaag cgcctaatct atctggtgtc taaactggac     180
tctggagtcc ctgacaggtt cactggcagt gggtcaggaa cagatttac actgaaaatc     240
```

```
agcagagtgg aggctgagga tttgggagtt tattactgcg tgcaaggtac acattttccg    300
ctcacgttcg gtgctgggac caagctggag ctgaaa                              336
```

<210> SEQ ID NO 79
<211> LENGTH: 115
<212> TYPE: PRT
<213> ORGANISM: Artificial Sequence
<220> FEATURE:
<223> OTHER INFORMATION: Amino acid sequence of 8G11 heavy chain
      variable region

<400> SEQUENCE: 79

```
Glu Val Gln Leu Gln Gln Ser Gly Pro Asp Leu Val Lys Pro Gly Thr
1               5                   10                  15

Ser Val Lys Ile Ser Cys Lys Ala Ser Gly Tyr Ser Phe Thr Gly Tyr
            20                  25                  30

Tyr Met His Trp Val Lys Gln Ser His Gly Lys Ser Leu Glu Trp Ile
        35                  40                  45

Gly His Ile Asn Pro Asn Asn Gly Gly Thr Ser Tyr Asn Gln Lys Phe
    50                  55                  60

Lys Gly Lys Thr Ile Leu Thr Val Asp Lys Ser Ser Thr Ala Phe
65                  70                  75                  80

Met Glu Leu Arg Ser Leu Thr Ser Glu Asp Ser Ala Val Tyr Tyr Cys
                85                  90                  95

Ala Arg Glu Glu Ala Phe Ala Tyr Trp Gly Gln Gly Thr Leu Val Thr
            100                 105                 110

Val Ser Ala
        115
```

<210> SEQ ID NO 80
<211> LENGTH: 345
<212> TYPE: DNA
<213> ORGANISM: Artificial Sequence
<220> FEATURE:
<223> OTHER INFORMATION: Nucleic acid sequence of 8G11 heavy chain
      variable region

<400> SEQUENCE: 80

```
gaggtgcaac ttcagcagtc tggacctgac ctggtgaagc ctgggacttc agtgaagata    60
tcctgcaagg cttctggtta ctcattcact ggctactaca tgcactgggt gaagcagagc    120
catggaaaga gccttgagtg gattggacat attaatccta acaatggtgg tactagctac    180
aaccagaagt tcaagggcaa gaccatatta actgtggaca gtcttccag cacagccttc     240 atggagctcc gcagcctgac atctgaggac tctgcggtct attactgtgc aagagaagaa    300
gcctttgctt actggggcca aggactctg gtcactgtct ctgca                     345
```

<210> SEQ ID NO 81
<211> LENGTH: 107
<212> TYPE: PRT
<213> ORGANISM: Artificial Sequence
<220> FEATURE:
<223> OTHER INFORMATION: Amino acid sequence of 8G11 light chain
      variable region

<400> SEQUENCE: 81

```
Asp Ile Val Met Thr Gln Ser Thr Ser Ser Leu Ser Ala Ser Leu Gly
1               5                   10                  15

Asp Arg Val Thr Ile Ser Cys Arg Ala Ser Gln Asp Ile Ser Asn Tyr
            20                  25                  30
```

```
Leu Asn Trp Tyr Gln Gln Lys Pro Asp Gly Thr Val Lys Leu Leu Ile
            35                  40                  45

Tyr Tyr Thr Ser Arg Leu His Ser Gly Val Pro Ser Arg Phe Ser Gly
        50                  55                  60

Ser Gly Ser Gly Thr Asp Phe Ser Leu Thr Ile Ser Asn Val Glu Gln
65                  70                  75                  80

Glu Asp Ile Ala Thr Tyr Phe Cys Gln Gln Gly Ile Thr Pro Pro Trp
                85                  90                  95

Thr Phe Gly Gly Gly Thr Lys Leu Glu Leu Lys
            100                 105
```

<210> SEQ ID NO 82
<211> LENGTH: 321
<212> TYPE: DNA
<213> ORGANISM: Artificial Sequence
<220> FEATURE:
<223> OTHER INFORMATION: Nucleic acid sequence of 8G11 light chain
      variable region

<400> SEQUENCE: 82

```
gatattgtga tgacccagtc tacatcctcc ctgtctgcct ctctgggaga cagagtcacc    60
atcagttgca gggcaagtca ggacattagc aattatttaa actggtatca gcagaaacca   120
gatggaactg ttaaactcct gatctactac acatcaagat tacactcagg agtcccatca   180
aggttcagtg gcagtgggtc tggaacagat ttttctctca ccattagcaa cgtggagcaa   240
gaagacattg ccacttactt ttgccaacag ggtattacgc ctccgtggac gttcggtgga   300
gggaccaagc tggagctgaa a                                             321
```

<210> SEQ ID NO 83
<211> LENGTH: 118
<212> TYPE: PRT
<213> ORGANISM: Artificial Sequence
<220> FEATURE:
<223> OTHER INFORMATION: Amino acid sequence of 39D2 heavy chain
      variable region

<400> SEQUENCE: 83

```
Glu Val Gln Leu Gln Gln Ser Gly Pro Glu Leu Lys Lys Pro Gly Glu
1               5                   10                  15

Thr Val Lys Ile Ser Cys Lys Ala Ser Gly Tyr Thr Phe Thr Asn Tyr
            20                  25                  30

Gly Val Asn Trp Val Lys Gln Ala Pro Gly Lys Gly Leu Lys Trp Met
        35                  40                  45

Gly Trp Ile Asn Thr His Thr Gly Glu Pro Thr Tyr Ala Glu Glu Phe
    50                  55                  60

Lys Gly Arg Phe Ala Phe Ser Leu Glu Thr Ser Ala Ser Thr Ala Tyr
65                  70                  75                  80

Leu Gln Ile Asn Asn Leu Lys Asn Glu Asp Thr Ala Thr Tyr Phe Cys
                85                  90                  95

Ala Arg Asp Asp Tyr Tyr Val Arg Val Asp Tyr Trp Gly Gln Gly Thr
            100                 105                 110

Thr Leu Thr Val Ser Ser
            115
```

<210> SEQ ID NO 84
<211> LENGTH: 354
<212> TYPE: DNA
<213> ORGANISM: Artificial Sequence
<220> FEATURE:
<223> OTHER INFORMATION: Nucleic acid sequence of 39D2 heavy chain variable region

<400> SEQUENCE: 84

```
gaggttcagc tgcagcagtc tggacctgag ctgaagaagc ctggagagac agtcaagatc      60
tcctgcaagg cttctgggta taccttcaca actatggag tgaattgggt gaagcaggct      120
ccaggaaagg gtttaaagtg gatgggctgg ataaacaccc acactggaga gccaacatat     180
gctgaagagt tcaagggacg gtttgccttc tctttggaaa cctctgccag cactgcctat     240
ttgcagatca caaccctcaa aaatgaggac acggctacat atttctgtgc aagagatgat     300
tactacgtaa gggtagacta ctgggggccaa ggcaccactc tcacagtctc ctca           354
```

<210> SEQ ID NO 85
<211> LENGTH: 107
<212> TYPE: PRT
<213> ORGANISM: Artificial Sequence
<220> FEATURE:
<223> OTHER INFORMATION: Amino acid sequence of 39D2 light chain variable region

<400> SEQUENCE: 85

```
Asp Ile Val Met Thr Gln Ser Pro Ser Ser Met Tyr Ala Ser Leu Gly
1               5                   10                  15
Glu Arg Val Thr Ile Thr Cys Lys Ala Ser Gln Asp Ile Asn Ser Tyr
            20                  25                  30
Leu Ser Trp Phe Gln Gln Lys Pro Gly Lys Ser Pro Lys Thr Leu Ile
        35                  40                  45
Tyr Arg Ala Asn Arg Leu Val Asp Gly Val Pro Ser Arg Phe Ser Gly
    50                  55                  60
Ser Gly Ser Gly Gln Asp Tyr Ser Leu Thr Ile Ser Ser Leu Glu Tyr
65                  70                  75                  80
Glu Asp Met Gly Ile Tyr Tyr Cys Leu Gln Tyr Asp Glu Phe Pro Trp
                85                  90                  95
Thr Phe Gly Gly Gly Thr Lys Leu Glu Leu Lys
            100                 105
```

<210> SEQ ID NO 86
<211> LENGTH: 321
<212> TYPE: DNA
<213> ORGANISM: Artificial Sequence
<220> FEATURE:
<223> OTHER INFORMATION: Nucleic acid sequence of 39D2 light chain variable region

<400> SEQUENCE: 86

```
gatattgtaa tgacccagtc tccatcttcc atgtatgcat ccctaggaga gagagtcact      60
atcacttgca aggcgagtca ggacattaat agctatttaa gctggttcca gcagaaacca     120
gggaaatctc ctaagaccct gatctatcgt gcaaacagat ggtagatgg ggtcccatca      180
aggttcagtg gcagtggatc tgggcaagat tattctctca ccatcagcag cctggagtat     240
gaagatatgg gaatttatta ttgtctacag tatgatgagt ttccgtggac gttcggtgga     300
gggaccaagc tggagctgaa a                                                321
```

<210> SEQ ID NO 87
<211> LENGTH: 118
<212> TYPE: PRT
<213> ORGANISM: Artificial Sequence
<220> FEATURE:

<223> OTHER INFORMATION: Amino acid sequence of hz39D2.14 heavy chain
      variable region

<400> SEQUENCE: 87

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
            85                  90                  95

Ala Arg Asp Glu Tyr Tyr Val Arg Thr Asp Tyr Trp Gly Gln Gly Thr
            100                 105                 110

Thr Val Thr Val Ser Ser
        115

<210> SEQ ID NO 88
<211> LENGTH: 354
<212> TYPE: DNA
<213> ORGANISM: Artificial Sequence
<220> FEATURE:
<223> OTHER INFORMATION: Nucleic acid sequence of hz39D2.14 heavy chain
      variable region

<400> SEQUENCE: 88
caagtccaac tcgtgcagtc aggatctgaa ctgaagaaac ctggagcgag cgttaaggtt      60
tcctgcaagg ccagcggcta tacgttcact aactatggtg tcaactgggt gagacaggca     120
cccggccagg gcctggagtg gatgggttgg atcaatactc acacagggga accaacatat     180
gctgaggagt tcaaaggacg gtttgttttt agtctggaca cctccgtgtc taccgcctac     240
ctgcagattt ccagccttaa agcagaggac actgctgtat actactgtgc cagagacgag     300
tactatgtga ggaccgatta ctgggggcag gggaccaccg tgacagtctc aagt           354

<210> SEQ ID NO 89
<211> LENGTH: 448
<212> TYPE: PRT
<213> ORGANISM: Artificial Sequence
<220> FEATURE:
<223> OTHER INFORMATION: Amino acid sequence of hz39D2.14 heavy chain

<400> SEQUENCE: 89

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
            85                  90                  95

Ala Arg Asp Glu Tyr Tyr Val Arg Thr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 90
<211> LENGTH: 1344
<212> TYPE: DNA
<213> ORGANISM: Artificial Sequence
<220> FEATURE:
<223> OTHER INFORMATION: Nucleic acid sequence of hz39D2.14 heavy chain

<400> SEQUENCE: 90

```
caagtccaac tcgtgcagtc aggatctgaa ctgaagaaac tggagcgag cgttaaggtt      60
tcctgcaagg ccagcggcta tacgttcact aactatggtg tcaactgggt gagacaggca    120
cccggccagg gctggagtg gatgggttgg atcaatactc acacagggga accaacatat    180
gctgaggagt tcaaaggacg gtttgttttt agtctggaca cctccgtgtc taccgcctac    240
ctgcagattt ccagccttaa agcagaggac actgctgtat actactgtgc cagagacgag    300
tactatgtga ggaccgatta ctgggggcag gggaccaccg tgacagtctc aagtgcctcc    360
accaagggcc cctccgtgtt ccctctggcc cctccagca agtccacctc tggcggcaca    420
gccgccctgg gctgcctggt gaaagactac ttccccgagc ccgtgaccgt gtcctggaac    480
tctggcgccc tgacctccgg cgtgcacacc ttccctgccg tgctgcagtc ctccggcctg    540
tactccctgt cctccgtggt gaccgtgccc tccagctctc tgggcaccca gacctacatc    600
tgtaacgtga accacaagcc ctccaacacc aaggtggaca gaaggtgga acccaagtcc    660
tgcgacaaga cccacacctg tccccctgc cctgccctg aactgctggg cggaccttcc    720
gtgttcctgt tccccccaaa gcccaaggac accctgatga tctcccggac ccccgaagtg    780
acctgcgtgg tggtggacgt gtcccacgag accctgaag tgaagttcaa ttggtacgtg    840
gacggcgtgg aagtgcacaa tgccaagacc aagcccagag aggaacagta caactccacc    900
taccgggtgg tgtctgtgct gaccgtgctg caccaggact ggctgaacgg caaagaatac    960
aagtgcaaag tctccaacaa ggccctgcct gcccccatcg aaaagaccat ctccaaggcc   1020
aagggccagc ccgcgagcc ccaggtgtac accctgcccc ctagccggga cgagctgacc   1080
aagaaccagg tgtccctgac ctgtctggtg aaaggcttct accctccga cattgccgtg   1140
gaatgggagt ccaacggcca gcccgagaac aactacaaga ccaccccccc tgtgctggac   1200
tccgacggct cattcttcct gtactccaag ctgaccgtgg acaagtcccg gtggcagcag   1260
ggcaacgtgt tctcctgctc cgtgatgcac gaggccctgc acaaccacta cacccagaag   1320
tccctgtccc tgagccccgg caag                                         1344
```

<210> SEQ ID NO 91
<211> LENGTH: 107
<212> TYPE: PRT
<213> ORGANISM: Artificial Sequence
<220> FEATURE:
<223> OTHER INFORMATION: Amino acid sequence of hz39D2.14 light chain variable region

<400> SEQUENCE: 91

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Trp
                85                  90                  95
```

```
Thr Phe Gly Gln Gly Thr Lys Val Glu Ile Lys
            100                 105
```

<210> SEQ ID NO 92
<211> LENGTH: 321
<212> TYPE: DNA
<213> ORGANISM: Artificial Sequence
<220> FEATURE:
<223> OTHER INFORMATION: Nucleic acid sequence of hz39D2.14 light chain
      variable region

<400> SEQUENCE: 92

```
cggaccgtgg ccgctccctc cgtgttcatc ttcccaccct ccgacgagca gctgaagtcc    60
ggcaccgcca gcgtggtctg cctgctgaac aacttctacc ccgcgaggc caaggtgcag   120 tggaaggtgg acaacgccct gcagtccggc aactcccagg aatccgtcac cgagcaggac   180
tccaaggaca gcacctactc cctgtcctcc accctgaccc tgtccaaggc cgactacgag   240
aagcacaagg tgtacgcctg cgaagtgacc caccagggcc tgtccagccc cgtgaccaag   300
tccttcaacc ggggcgagtg c                                             321
```

<210> SEQ ID NO 93
<211> LENGTH: 214
<212> TYPE: PRT
<213> ORGANISM: Artificial Sequence
<220> FEATURE:
<223> OTHER INFORMATION: Amino acid sequence of hz39D2.14 light chain

<400> SEQUENCE: 93

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Tyr Asp Glu Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 94
<211> LENGTH: 642
<212> TYPE: DNA
<213> ORGANISM: Artificial Sequence
<220> FEATURE:
<223> OTHER INFORMATION: Nucleic acid sequence of hz39D2.14 light chain

<400> SEQUENCE: 94

```
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctgcaa tacgatgagt tcccatggac cttcggccag     300
ggcaccaagg tggagattaa acggaccgtg gccgctccct ccgtgttcat cttcccaccc     360
tccgacgagc agctgaagtc cggcaccgcc agcgtggtct gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga gaagcacaag gtgtacgcct gcgaagtgac ccaccagggc     600
ctgtccagcc ccgtgaccaa gtccttcaac cggggcgagt gc                        642
```

<210> SEQ ID NO 95
<211> LENGTH: 118
<212> TYPE: PRT
<213> ORGANISM: Artificial Sequence
<220> FEATURE:
<223> OTHER INFORMATION: Amino acid sequence of hz39D2.22 heavy chain
      variable region

<400> SEQUENCE: 95

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Glu Tyr Tyr Val Arg Val Asp Tyr Trp Gly Gln Gly Thr
            100                 105                 110

Thr Val Thr Val Ser Ser
        115
```

<210> SEQ ID NO 96
<211> LENGTH: 354
<212> TYPE: DNA
<213> ORGANISM: Artificial Sequence
<220> FEATURE:
<223> OTHER INFORMATION: Nucleic acid sequence of hz39D2.22 heavy chain
      variable region

<400> SEQUENCE: 96

```
caagtccaac tcgtgcagtc aggatctgaa ctgaagaaac ctggagcgag cgttaaggtt      60
tcctgcaagg ccagcggcta tacgttcact aactatggtg tcaactgggt gagacaggca     120
cccggccagg gctggagtg gatgggttgg atcaatactc acacagggga accaacatat     180
gctgaggagt tcaaaggacg gtttgttttt agtctggaca cctccgtgtc taccgcctac     240
ctgcagattt ccagccttaa agcagaggac actgctgtat actactgtgc cagagacgag     300
tactatgtga gggtggatta ctgggggcag gggaccaccg tgacagtctc aagt           354
```

<210> SEQ ID NO 97
<211> LENGTH: 448
<212> TYPE: PRT
<213> ORGANISM: Artificial Sequence
<220> FEATURE:
<223> OTHER INFORMATION: Amino acid sequence of hz39D2.22 heavy chain

<400> SEQUENCE: 97

```
Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
    50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
                85                  90                  95

Ala Arg Asp Glu Tyr Tyr Val Arg Val Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285
```

```
Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
                340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
                420                 425                 430

Leu His Asn His Tyr Thr Gln Lys Ser Leu Ser Leu Ser Pro Gly Lys
            435                 440                 445
```

<210> SEQ ID NO 98
<211> LENGTH: 1344
<212> TYPE: DNA
<213> ORGANISM: Artificial Sequence
<220> FEATURE:
<223> OTHER INFORMATION: Nucleic acid sequence of hz39D2.22 heavy chain

<400> SEQUENCE: 98

```
caagtccaac tcgtgcagtc aggatctgaa ctgaagaaac ctggagcgag cgttaaggtt      60
tcctgcaagg ccagcggcta cgttcact aactatggtg tcaactgggt gagacaggca      120
cccggccagg gctggagtg atgggttgg atcaatactc acacagggga accaacatat      180
gctgaggagt tcaaaggacg gtttgttttt agtctggaca cctccgtgtc taccgcctac      240
ctgcagattt ccagccttaa agcagaggac actgctgtat actactgtgc cagagacgag      300
tactatgtga gggtggatta ctgggggcag ggaccaccg tgacagtctc aagtgcctcc      360
accaagggcc cctccgtgtt ccctctggcc cctccagca agtccacctc tggcggcaca      420
gccgccctgg gctgcctggt gaaagactac ttccccgagc cgtgaccgt gtcctggaac      480 tctggcgccc tgacctccgg cgtgcacacc ttccctgccg tgctgcagtc ctccggcctg      540
tactccctgt cctccgtggt gaccgtgccc tccagctctc tgggcaccca gacctacatc      600
tgtaacgtga accacaagcc ctccaacacc aaggtggaca gaaggtgga acccaagtcc      660 tgcgacaaga cccacacctg tcccccctgc cctgcccctg aactgctggg cggaccttcc      720
gtgttcctgt tccccccaaa gcccaaggac accctgatga tctcccggac ccccgaagtg      780
acctgcgtgg tggtggacgt gtcccacgag accctgaag tgaagttcaa ttggtacgtg      840
gacggcgtgg aagtgcacaa tgccaagacc aagcccagag aggaacagta caactccacc      900
taccgggtgg tgtctgtgct gaccgtgctg caccaggact ggctgaacgg caaagaatac      960
aagtgcaaag tctccaacaa ggccctgcct gccccatcg aaaagaccat ctccaaggcc      1020
aagggccagc ccgcgagcc ccaggtgtac accctgcccc ctagccggga cgagctgacc      1080
aagaaccagg tgtccctgac ctgtctggtg aaaggcttct acccctccga cattgccgtg      1140
gaatgggagt ccaacggcca gcccgagaac aactacaaga ccaccccccc tgtgctggac      1200
```
tccgacggct cattcttcct gtactccaag ctgaccgtgg acaagtcccg gtggcagcag        1260
ggcaacgtgt tctcctgctc cgtgatgcac gaggccctgc acaaccacta cacccagaag        1320
tccctgtccc tgagccccgg caag                                               1344

<210> SEQ ID NO 99
<211> LENGTH: 107
<212> TYPE: PRT
<213> ORGANISM: Artificial Sequence
<220> FEATURE:
<223> OTHER INFORMATION: Amino acid sequence of hz39D2.22 light chain
      variable region

<400> SEQUENCE: 99

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Glu Leu Asp Glu Phe Pro Trp
                85                  90                  95

Thr Phe Gly Gln Gly Thr Lys Val Glu Ile Lys
            100                 105

<210> SEQ ID NO 100
<211> LENGTH: 321
<212> TYPE: DNA
<213> ORGANISM: Artificial Sequence
<220> FEATURE:
<223> OTHER INFORMATION: Nucleic acid sequence of hz39D2.22 light chain
      variable region

<400> SEQUENCE: 100
gacattcaaa tgacacagtc tcccagctcc cttagtgctt cggtgggcga tcgggtgacc        60
ataacatgca aggcctcaca ggacatcaac agctatctct catggtttca gcagaagcca       120
ggaaaagcac ctaaaacgtt gatctacagg gccaatcgcc tcgttgacgg agtcccctcc       180
agattcagcg ggagtgggtc tggtcaggat tatactctga ccatctcctc tctgcagcct       240
gaagactttg ccacttacta ctgtctggag ctcgatgagt tcccatggac cttcggccag       300
ggcaccaagg tggagattaa a                                                 321

<210> SEQ ID NO 101
<211> LENGTH: 214
<212> TYPE: PRT
<213> ORGANISM: Artificial Sequence
<220> FEATURE:
<223> OTHER INFORMATION: Amino acid sequence of hz39D2.22 light chain

<400> SEQUENCE: 101

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
            35                  40                  45

Tyr Arg Ala Asn Arg Leu Val Asp Gly Val Pro Ser Arg Phe Ser Gly
        50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Glu Leu Asp Glu Phe Pro Trp
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Glu Gln Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 102
<211> LENGTH: 642
<212> TYPE: DNA
<213> ORGANISM: Artificial Sequence
<220> FEATURE:
<223> OTHER INFORMATION: Nucleic acid sequence of hz39D2.22 light chain

<400> SEQUENCE: 102
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctggag ctcgatgagt tcccatggac cttcggccag     300
ggcaccaagg tggagattaa acggaccgtg gccgctccct ccgtgttcat cttcccaccc     360
tccgacgagc agctgaagtc cggcaccgcc agcgtggtct gcctgctgaa caacttctac     420
ccccgcgagg ccaaggtgca gtggaaggtg gacaacgccc tgcagtccgg caactcccag     480
gaatccgtca ccgagcagga ctccaaggac agcacctact ccctgtcctc caccctgacc     540
ctgtccaagg ccgactacga aaagcacaag gtgtacgcct gcgaagtgac ccaccagggc     600
ctgtccagcc ccgtgaccaa gtccttcaac cggggcgagt gc                       642

<210> SEQ ID NO 103
<211> LENGTH: 118
<212> TYPE: PRT
<213> ORGANISM: Artificial Sequence
<220> FEATURE:
<223> OTHER INFORMATION: Amino acid sequence of hz39D2.23 heavy chain
      variable region

<400> SEQUENCE: 103

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
            85                  90                  95

Ala Arg Asp Glu Tyr Tyr Val Arg Val Asp Tyr Trp Gly Gln Gly Thr
        100                 105                 110

Thr Val Thr Val Ser Ser
        115

<210> SEQ ID NO 104
<211> LENGTH: 354
<212> TYPE: DNA
<213> ORGANISM: Artificial Sequence
<220> FEATURE:
<223> OTHER INFORMATION: Nucleic acid sequence of hz39D2.23 heavy chain
      variable region

<400> SEQUENCE: 104
caagtccaac tcgtgcagtc aggatctgaa ctgaagaaac tggagcgag cgttaaggtt      60 tcctgcaagg ccagcggcta tacgttcact aactatggtg tcaactgggt gagacaggca    120
cccggccagg gcctggagtg gatgggttgg atcaatactc acacagggga accaacatat    180
gctgaggagt tcaaaggacg gtttgttttt agtctggaca cctccgtgtc taccgcctac    240
ctgcagattt ccagccttaa agcagaggac actgctgtat actactgtgc cagagacgag    300
tactatgtga gggtggatta ctgggggcag gggaccaccg tgacagtctc aagt           354

<210> SEQ ID NO 105
<211> LENGTH: 448
<212> TYPE: PRT
<213> ORGANISM: Artificial Sequence
<220> FEATURE:
<223> OTHER INFORMATION: Amino acid sequence of hz39D2.23 heavy chain

<400> SEQUENCE: 105

Gln Val Gln Leu Val Gln Ser Gly Ser Glu Leu Lys Lys Pro Gly Ala
1               5                   10                  15

Ser Val Lys Val Ser Cys Lys Ala Ser Gly Tyr Thr Phe Thr Asn Tyr
            20                  25                  30

Gly Val Asn Trp Val Arg Gln Ala Pro Gly Gln Gly Leu Glu Trp Met
        35                  40                  45

Gly Trp Ile Asn Thr His Thr Gly Glu Pro Thr Tyr Ala Glu Glu Phe
50                  55                  60

Lys Gly Arg Phe Val Phe Ser Leu Asp Thr Ser Val Ser Thr Ala Tyr
65                  70                  75                  80

Leu Gln Ile Ser Ser Leu Lys Ala Glu Asp Thr Ala Val Tyr Tyr Cys
            85                  90                  95

Ala Arg Asp Glu Tyr Tyr Val Arg Val Asp Tyr Trp Gly Gln Gly Thr
                100                 105                 110

Thr Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
                180                 185                 190

Ser Leu Gly Thr Gln Thr Tyr Ile Cys Asn Val Asn His Lys Pro Ser
                195                 200                 205

Asn Thr Lys Val Asp Lys Lys Val Glu Pro Lys Ser Cys Asp Lys Thr
            210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
                260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
        290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 106
<211> LENGTH: 1344
<212> TYPE: DNA
<213> ORGANISM: Artificial Sequence
<220> FEATURE:
<223> OTHER INFORMATION: Nucleic acid sequence of hz39D2.23 heavy chain

<400> SEQUENCE: 106

```
caagtccaac tcgtgcagtc aggatctgaa ctgaagaaac tggagcgag cgttaaggtt        60
tcctgcaagg ccagcggcta tacgttcact aactatggtg tcaactgggt gagacaggca       120
cccggccagg gctggagtg gatgggttgg atcaatactc acacagggga accaacatat       180
gctgaggagt tcaaaggacg gtttgttttt agtctggaca cctccgtgtc taccgcctac       240
ctgcagattt ccagccttaa agcagaggac actgctgtat actactgtgc cagagacgag       300
tactatgtga gggtggatta ctgggggcag gggaccaccg tgacagtctc aagtgcctcc       360
accaagggcc cctccgtgtt ccctctggcc cctccagca agtccacctc tggcggcaca       420
gccgccctgg gctgcctggt gaaagactac ttccccgagc ccgtgaccgt gtcctggaac       480
tctggcgccc tgacctccgg cgtgcacacc ttccctgccg tgctgcagtc ctccggcctg       540
tactccctgt cctccgtggt gaccgtgccc tccagctctc tgggcaccca gacctacatc       600
tgtaacgtga accacaagcc ctccaacacc aaggtggaca gaaggtgga acccaagtcc       660
tgcgacaaga cccacacctg tccccctgc cctgccctg aactgctggg cggaccttcc        720
gtgttcctgt tccccccaaa gcccaaggac ccctgatga tctcccggac ccccgaagtg       780
acctgcgtgg tggtggacgt gtcccacgag gaccctgaag tgaagttcaa ttggtacgtg       840
gacggcgtgg aagtgcacaa tgccaagacc aagcccagag aggaacagta caactccacc       900
taccgggtgg tgtctgtgct gaccgtgctg caccaggact ggctgaacgg caaagaatac       960
aagtgcaaag tctccaacaa ggccctgcct gcccccatcg aaaagaccat ctccaaggcc      1020
aagggccagc ccgcgagcc ccaggtgtac accctgcccc ctagccggga cgagctgacc       1080
aagaaccagg tgtccctgac ctgtctggtg aaaggcttct accctccga cattgccgtg       1140
gaatgggagt ccaacggcca gcccgagaac aactacaaga ccacccccc tgtgctggac       1200
tccgacggct cattcttcct gtactccaag ctgaccgtgg acaagtcccg gtggcagcag      1260
ggcaacgtgt tctcctgctc cgtgatgcac gaggccctgc acaaccacta cacccagaag      1320
tccctgtccc tgagccccgg caag                                             1344
```

<210> SEQ ID NO 107
<211> LENGTH: 107
<212> TYPE: PRT
<213> ORGANISM: Artificial Sequence
<220> FEATURE:
<223> OTHER INFORMATION: Amino acid sequence of hz39D2.23 light chain
    variable region

<400> SEQUENCE: 107

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Leu Asp Glu Phe Pro Trp
            85                  90                  95
```

```
Thr Phe Gly Gln Gly Thr Lys Val Glu Ile Lys
            100                 105
```

<210> SEQ ID NO 108
<211> LENGTH: 321
<212> TYPE: DNA
<213> ORGANISM: Artificial Sequence
<220> FEATURE:
<223> OTHER INFORMATION: Nucleic acid sequence of hz39D2.23 light chain
      variable region

<400> SEQUENCE: 108

```
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtcccctcc     180
agattcagcg ggagtgggtc tggtcaggat tatactctga ccatctcctc tctgcagcct     240
gaagactttg ccacttacta ctgtctgcaa ctcgatgagt tcccatggac cttcggccag     300
ggcaccaagg tggagattaa a                                               321
```

<210> SEQ ID NO 109
<211> LENGTH: 214
<212> TYPE: PRT
<213> ORGANISM: Artificial Sequence
<220> FEATURE:
<223> OTHER INFORMATION: Amino acid sequence of hz39D2.23 light chain

<400> SEQUENCE: 109

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
    50                  55                  60

Ser Gly Ser Gly Gln Asp Tyr Thr Leu Thr Ile Ser Ser Leu Gln Pro
65                  70                  75                  80

Glu Asp Phe Ala Thr Tyr Tyr Cys Leu Gln Leu Asp Glu Phe Pro Trp
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 110
<211> LENGTH: 642
<212> TYPE: DNA
<213> ORGANISM: Artificial Sequence
<220> FEATURE:
<223> OTHER INFORMATION: Nucleic acid sequence of hz39D2.23 light chain

<400> SEQUENCE: 110

```
gacattcaaa tgacacagtc tcccagctcc cttagtgctt cggtgggcga tcgggtgacc      60
ataacatgca aggcctcaca ggacatcaac agctatctct catggtttca gcagaagcca     120
ggaaaagcac ctaaaacgtt gatctacagg gccaatcgcc tcgttgacgg agtccccctcc    180
agattcagcg ggagtgggtc tggtcaggat tatactctga ccatctcctc tctgcagcct    240
gaagactttg ccacttacta ctgtctgcaa ctcgatgagt tcccatggac cttcggccag    300
ggcaccaagg tggagattaa acggaccgtg gccgctccct ccgtgttcat cttcccaccc    360
tccgacgagc agctgaagtc cggcaccgcc agcgtggtct gcctgctgaa caacttctac    420
ccccgcgagg ccaaggtgca gtggaaggtg acaacgccc tgcagtccgg caactcccag     480
gaatccgtca ccgagcagga ctccaaggac agcacctact ccctgtcctc caccctgacc    540
ctgtccaagg ccgactacga aagcacaag gtgtacgcct gcgaagtgac ccaccagggc    600
ctgtccagcc ccgtgaccaa gtccttcaac cggggcgagt gc                       642
```

<210> SEQ ID NO 111
<211> LENGTH: 21
<212> TYPE: PRT
<213> ORGANISM: Artificial Sequence
<220> FEATURE:
<223> OTHER INFORMATION: Signal peptide (CD8alpha)

<400> SEQUENCE: 111

Met Ala Leu Pro Val Thr Ala Leu Leu Leu Pro Leu Ala Leu Leu Leu
1               5                   10                  15

His Ala Ala Arg Pro
            20

<210> SEQ ID NO 112
<211> LENGTH: 63
<212> TYPE: DNA
<213> ORGANISM: Artificial Sequence
<220> FEATURE:
<223> OTHER INFORMATION: Signal peptide (CD8alpha)

<400> SEQUENCE: 112

```
atggctctgc cagtgactgc actgctgctg ccactggccc tgctgctgca cgcagctcga     60
cct                                                                   63
```

<210> SEQ ID NO 113
<211> LENGTH: 240
<212> TYPE: PRT
<213> ORGANISM: Artificial Sequence
<220> FEATURE:
<223> OTHER INFORMATION: Anti-HER2 scFv

<400> SEQUENCE: 113

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Ile Asn Ser Tyr
            20                  25                  30

Leu Ser Trp Phe Gln Gln Lys Pro Gly Lys Ala Pro Lys Thr Leu Ile
        35                  40                  45

Tyr Arg Ala Asn Arg Leu Val Asp Gly Val Pro Ser Arg Phe Ser Gly
 50                  55                  60

Ser Gly Ser Gly Gln Asp Tyr Thr Leu Thr Ile Ser Ser Leu Gln Pro
 65                  70                  75                  80

Glu Asp Phe Ala Thr Tyr Tyr Cys Leu Gln Tyr Asp Glu Phe Pro Trp
                 85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Gln Val Gln Leu Val Gln
            115                 120                 125

Ser Gly Ser Glu Leu Lys Lys Pro Gly Ala Ser Val Lys Val Ser Cys
130                 135                 140

Lys Ala Ser Gly Tyr Thr Phe Thr Asn Tyr Gly Val Asn Trp Val Arg
145                 150                 155                 160

Gln Ala Pro Gly Gln Gly Leu Glu Trp Met Gly Trp Ile Asn Thr His
                165                 170                 175

Thr Gly Glu Pro Thr Tyr Ala Glu Glu Phe Lys Gly Arg Phe Val Phe
            180                 185                 190

Ser Leu Asp Thr Ser Val Ser Thr Ala Tyr Leu Gln Ile Ser Ser Leu
        195                 200                 205

Lys Ala Glu Asp Thr Ala Val Tyr Tyr Cys Ala Arg Asp Asp Tyr Tyr
    210                 215                 220

Val Arg Val Asp Tyr Trp Gly Gln Gly Thr Thr Val Thr Val Ser Ser
225                 230                 235                 240

<210> SEQ ID NO 114
<211> LENGTH: 720
<212> TYPE: DNA
<213> ORGANISM: Artificial Sequence
<220> FEATURE:
<223> OTHER INFORMATION: Anti-HER2 scFv

<400> SEQUENCE: 114
gacatccaga tgacccagag ccccagcagc ctgagcgcca gcgtgggcga cagagtgacc      60
atcacctgca aggccagcca ggacatcaac agctacctga ctggttcca gcagaagccc     120 ggcaaggccc ccaagaccct gatctacaga gccaacagac tggtggacgg cgtgcccagc     180
agattcagcg gcagcggcag cggccaggac tacaccctga ccatcagcag cctgcagccc     240
gaggacttcg ccacctacta ctgcctgcag tacgacgagt tcccctggac cttcggccag     300
ggcaccaagg tggagatcaa gggtggcggt ggatcgggcg gtggtggatc tggaggaggt     360
ggctcccagg tgcagctggt gcagagcggc agcgagctga agaagcccgg cgccagcgtg     420
aaggtgagct gcaaggccag cggctacacc ttcaccaact acggcgtgaa ctgggtgaga     480
caggcccccg gccagggcct ggagtggatg ggctggatca cacccacac cggcgagccc     540 acctacgccg aggagttcaa gggcagattc gtgttcagcc tggacaccag cgtgagcacc     600
gcctacctgc agatcagcag cctgaaggcc gaggacaccg ccgtgtacta ctgcgccaga     660
gacgactact acgtgagagt ggactactgg ggccagggca ccaccgtgac cgtgagcagc     720

<210> SEQ ID NO 115
<211> LENGTH: 48
<212> TYPE: PRT
<213> ORGANISM: Artificial Sequence
<220> FEATURE:
<223> OTHER INFORMATION: Hinge (CD8alpha)

<400> SEQUENCE: 115

Ala Lys Pro Thr Thr Thr Pro Ala Pro Arg Pro Pro Thr Pro Ala Pro
1               5                   10                  15

Thr Ile Ala Ser Gln Pro Leu Ser Leu Arg Pro Glu Ala Cys Arg Pro
            20                  25                  30

Ala Ala Gly Gly Ala Val His Thr Arg Gly Leu Asp Phe Ala Cys Asp
        35                  40                  45

<210> SEQ ID NO 116
<211> LENGTH: 144
<212> TYPE: DNA
<213> ORGANISM: Artificial Sequence
<220> FEATURE:
<223> OTHER INFORMATION: Hinge (CD8alpha)

<400> SEQUENCE: 116
gcaaaaccta ccacaactcc tgcaccacgc ccccctactc cagcacctac catcgcatct    60
cagccactga gtctgcgacc agaggcctgc ggcccgccg ccggcggggc cgtccatacc    120
agagggctgg actttgcctg cgat                                         144

<210> SEQ ID NO 117
<211> LENGTH: 24
<212> TYPE: PRT
<213> ORGANISM: Artificial Sequence
<220> FEATURE:
<223> OTHER INFORMATION: Transmembrane (CD8alpha)

<400> SEQUENCE: 117

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 118
<211> LENGTH: 72
<212> TYPE: DNA
<213> ORGANISM: Artificial Sequence
<220> FEATURE:
<223> OTHER INFORMATION: Transmembrane (CD8alpha)

<400> SEQUENCE: 118
atctacattt gggcccctct ggctggaaca tgtggcgtgc tgctgctgtc cctggtcatt    60
actctgtatt gt                                                      72

<210> SEQ ID NO 119
<211> LENGTH: 27
<212> TYPE: PRT
<213> ORGANISM: Artificial Sequence
<220> FEATURE:
<223> OTHER INFORMATION: Transmembrane (CD28)

<400> SEQUENCE: 119

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 120
<211> LENGTH: 81

```
<212> TYPE: DNA
<213> ORGANISM: Artificial Sequence
<220> FEATURE:
<223> OTHER INFORMATION: Transmembrane (CD28)

<400> SEQUENCE: 120
ttttgggtcc tggtggtcgt gggaggggtg ctggcatgtt actcactgct ggtcaccgtg      60
gccttcatca tcttctgggt g                                                81

<210> SEQ ID NO 121
<211> LENGTH: 112
<212> TYPE: PRT
<213> ORGANISM: Artificial Sequence
<220> FEATURE:
<223> OTHER INFORMATION: Intracellular stimulatory Signal- (CD3-lambda)

<400> SEQUENCE: 121
```

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Arg Arg Lys Asn Pro Gln Glu Gly Leu Tyr Asn Glu Leu Gln Lys
    50                  55                  60

Asp Lys Met Ala Glu Ala Tyr Ser Glu Ile Gly Met Lys Gly Glu Arg
65                  70                  75                  80

Arg Arg Gly Lys Gly His Asp Gly Leu Tyr Gln Gly Leu Ser Thr Ala
                85                  90                  95

Thr Lys Asp Thr Tyr Asp Ala Leu His Met Gln Ala Leu Pro Pro Arg
            100                 105                 110

```
<210> SEQ ID NO 122
<211> LENGTH: 339
<212> TYPE: DNA
<213> ORGANISM: Artificial Sequence
<220> FEATURE:
<223> OTHER INFORMATION: Intracellular stimulatory Signal- (CD3-lambda)

<400> SEQUENCE: 122
cgagtgaagt tcagcaggtc cgccgacgct cctgcatacc agcagggaca gaaccagctg      60
tataacgagc tgaatctggg ccggagagag gaatacgacg tgctggacaa aaggcggggc     120
cgggaccccg aaatgggagg gaagccacga cggaaaaacc cccaggaggg cctgtacaat     180
gagctgcaaa aggacaaaat ggccgaggct tattctgaaa tcgggatgaa gggagagaga     240
aggcgcggaa aaggccacga tggcctgtac caggggctga gcaccgctac aaaggacacc     300
tatgatgcac tgcacatgca ggccctgccc cctcggtga                            339

<210> SEQ ID NO 123
<211> LENGTH: 42
<212> TYPE: PRT
<213> ORGANISM: Artificial Sequence
<220> FEATURE:
<223> OTHER INFORMATION: Intracellular stimulatory signal (4-1BB)

<400> SEQUENCE: 123
```

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 124
<211> LENGTH: 126
<212> TYPE: DNA
<213> ORGANISM: Artificial Sequence
<220> FEATURE:
<223> OTHER INFORMATION: Intracellular stimulatory signal (4-1BB)

<400> SEQUENCE: 124
aagcggggaa gaaagaaact gctgtacatc ttcaaacagc cctttatgag gcctgtgcag    60
accacacagg aggaagacgg ctgctcctgc cggttccccg aggaagagga aggcgggtgc   120
gagctg                                                             126

<210> SEQ ID NO 125
<211> LENGTH: 41
<212> TYPE: PRT
<213> ORGANISM: Artificial Sequence
<220> FEATURE:
<223> OTHER INFORMATION: Intracellular stimulatory signal (CD28)

<400> SEQUENCE: 125

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 126
<211> LENGTH: 123
<212> TYPE: DNA
<213> ORGANISM: Artificial Sequence
<220> FEATURE:
<223> OTHER INFORMATION: Intracellular stimulatory signal (CD28)

<400> SEQUENCE: 126
cggagcaaga ggtcccgcct gctgcacagc gactatatga acatgacccc acggagaccc    60
ggccctacac ggaaacatta ccagccctat gctccacccc gggacttcgc agcttacaga   120
agt                                                                123

<210> SEQ ID NO 127
<211> LENGTH: 22
<212> TYPE: PRT
<213> ORGANISM: Artificial Sequence
<220> FEATURE:
<223> OTHER INFORMATION: Intracellular stimulatory signal (OX40 ligand)

<400> SEQUENCE: 127

Glu Arg Val Gln Pro Leu Glu Glu Asn Val Gly Asn Ala Ala Arg Pro
1               5                   10                  15

Arg Phe Glu Arg Asn Lys
            20

<210> SEQ ID NO 128
<211> LENGTH: 66
<212> TYPE: DNA
<213> ORGANISM: Artificial Sequence
<220> FEATURE:
<223> OTHER INFORMATION: Intracellular stimulatory signal (OX40 ligand)

<400> SEQUENCE: 128

```
gaaagagtgc agcccctgga agagaatgtc gggaatgccg ctcgcccaag atttgaaagg    60
aacaaa                                                                66
```

<210> SEQ ID NO 129
<211> LENGTH: 445
<212> TYPE: PRT
<213> ORGANISM: Artificial Sequence
<220> FEATURE:
<223> OTHER INFORMATION: Her2-Z CAR (Clone #2)

<400> SEQUENCE: 129

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Lys Ala Ser Gln
        35                  40                  45

Asp Ile Asn Ser Tyr Leu Ser Trp Phe Gln Gln Lys Pro Gly Lys Ala
    50                  55                  60

Pro Lys Thr Leu Ile Tyr Arg Ala Asn Arg Leu Val Asp Gly Val Pro
65                  70                  75                  80

Ser Arg Phe Ser Gly Ser Gly Ser Gly Gln Asp Tyr Thr Leu Thr Ile
                85                  90                  95

Ser Ser Leu Gln Pro Glu Asp Phe Ala Thr Tyr Tyr Cys Leu Gln Tyr
            100                 105                 110

Asp Glu Phe Pro Trp Thr Phe Gly Gln Gly Thr Lys Val Glu Ile Lys
        115                 120                 125

Gly Gly Gly Gly Ser Gly Gly Gly Gly Ser Gly Gly Gly Gly Ser Gln
    130                 135                 140

Val Gln Leu Val Gln Ser Gly Ser Glu Leu Lys Lys Pro Gly Ala Ser
145                 150                 155                 160

Val Lys Val Ser Cys Lys Ala Ser Gly Tyr Thr Phe Thr Asn Tyr Gly
                165                 170                 175

Val Asn Trp Val Arg Gln Ala Pro Gly Gln Gly Leu Glu Trp Met Gly
            180                 185                 190

Trp Ile Asn Thr His Thr Gly Glu Pro Thr Tyr Ala Glu Glu Phe Lys
        195                 200                 205

Gly Arg Phe Val Phe Ser Leu Asp Thr Ser Val Ser Thr Ala Tyr Leu
    210                 215                 220

Gln Ile Ser Ser Leu Lys Ala Glu Asp Thr Ala Val Tyr Tyr Cys Ala
225                 230                 235                 240

Arg Asp Asp Tyr Tyr Val Arg Val Asp Tyr Trp Gly Gln Gly Thr Thr
                245                 250                 255

Val Thr Val Ser Ser Ala Lys Pro Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Ile Tyr Ile Trp Ala Pro Leu Ala Gly Thr Cys
305                 310                 315                 320

Gly Val Leu Leu Leu Ser Leu Val Ile Thr Leu Tyr Cys Arg Val Lys
                325                 330                 335
```

```
Phe Ser Arg Ser Ala Asp Ala Pro Ala Tyr Gln Gln Gly Gln Asn Gln
                340                 345                 350

Leu Tyr Asn Glu Leu Asn Leu Gly Arg Arg Glu Glu Tyr Asp Val Leu
            355                 360                 365

Asp Lys Arg Arg Gly Arg Asp Pro Glu Met Gly Gly Lys Pro Arg Arg
        370                 375                 380

Lys Asn Pro Gln Glu Gly Leu Tyr Asn Glu Leu Gln Lys Asp Lys Met
385                 390                 395                 400

Ala Glu Ala Tyr Ser Glu Ile Gly Met Lys Gly Glu Arg Arg Arg Gly
                405                 410                 415

Lys Gly His Asp Gly Leu Tyr Gln Gly Leu Ser Thr Ala Thr Lys Asp
                420                 425                 430

Thr Tyr Asp Ala Leu His Met Gln Ala Leu Pro Pro Arg
            435                 440                 445

<210> SEQ ID NO 130
<211> LENGTH: 1338
<212> TYPE: DNA
<213> ORGANISM: Artificial Sequence
<220> FEATURE:
<223> OTHER INFORMATION: Her2-Z CAR (Clone #2)

<400> SEQUENCE: 130
```

| | | | | | |
|---|---|---|---|---|---|
| atggctctgc | cagtgactgc | actgctgctg | ccactggccc | tgctgctgca | cgcagctcga | 60 |
| cctgacatcc | agatgaccca | gagccccagc | agcctgagcg | ccagcgtggg | cgacagagtg | 120 |
| accatcacct | gcaaggccag | ccaggacatc | aacagctacc | tgagctggtt | ccagcagaag | 180 |
| cccggcaagg | cccccaagac | cctgatctac | agagccaaca | gactggtgga | cggcgtgccc | 240 |
| agcagattca | gcggcagcgg | cagcggccag | gactacaccc | tgaccatcag | cagcctgcag | 300 |
| cccgaggact | tcgccaccta | ctactgcctg | cagtacgacg | agttcccctg | gaccttcggc | 360 |
| cagggcacca | aggtggagat | caagggtggc | ggtggatcgg | cggtggtgg | atctggagga | 420 |
| ggtggctccc | aggtgcagct | ggtgcagagc | ggcagcgagc | tgaagaagcc | cggcgccagc | 480 |
| gtgaaggtga | gctgcaaggc | cagcggctac | accttcacca | actacggcgt | gaactgggtg | 540 |
| agacaggccc | ccgccagggg | cctggagtgg | atgggctgga | tcaacaccca | caccggcgag | 600 |
| cccacctacg | ccgaggagtt | caagggcaga | ttcgtgttca | gcctggacac | cagcgtgagc | 660 |
| accgccacct | gcagatcag | cagcctgaag | gccgaggaca | ccgccgtgta | ctactgcgcc | 720 |
| agagacgact | actacgtgag | agtggactac | tggggccagg | gcaccaccgt | gaccgtgagc | 780 |
| agcgcaaaac | ctaccacaac | tcctgcacca | cgccccccta | ctccagcacc | taccatcgca | 840 |
| tctcagccac | tgagtctgcg | accagaggcc | tgccggcccg | ccgccggcgg | ggccgtccat | 900 |
| accgagggc | tggactttgc | ctgcgatatc | tacatttggg | cccctctggc | tggaacatgt | 960 |
| ggcgtgctgc | tgctgtccct | ggtcattact | ctgtattgtc | gagtgaagtt | cagcaggtcc | 1020 |
| gccgacgctc | ctgcatacca | gcagggacag | aaccagctgt | ataacgagct | gaatctgggc | 1080 |
| cggagagagg | aatacgacgt | gctggacaaa | aggcggggcc | gggaccccga | atgggagggg | 1140 |
| aagccacgac | ggaaaaaccc | ccaggagggc | ctgtacaatg | agctgcaaaa | ggacaaaatg | 1200 |
| gccgaggctt | attctgaaat | cgggatgaag | ggagagagaa | ggcgcggaaa | aggccacgat | 1260 |
| ggcctgtacc | aggggctgag | caccgctaca | aaggacacct | atgatgcact | gcacatgcag | 1320 |
| gccctgcccc | ctcggtga | | | | | 1338 |

```
<210> SEQ ID NO 131
```

```
<211> LENGTH: 487
<212> TYPE: PRT
<213> ORGANISM: Artificial Sequence
<220> FEATURE:
<223> OTHER INFORMATION: Her2-BBZ CAR (Clone #3)

<400> SEQUENCE: 131
```

| Met<br>1 | Ala | Leu | Pro | Val<br>5 | Thr | Ala | Leu | Leu | Leu<br>10 | Pro | Leu | Ala | Leu | Leu<br>15 | Leu |
|---|---|---|---|---|---|---|---|---|---|---|---|---|---|---|---|
| His | Ala | Ala | Arg<br>20 | Pro | Asp | Ile | Gln | Met<br>25 | Thr | Gln | Ser | Pro | Ser<br>30 | Ser | Leu |
| Ser | Ala | Ser<br>35 | Val | Gly | Asp | Arg | Val<br>40 | Thr | Ile | Thr | Cys | Lys<br>45 | Ala | Ser | Gln |
| Asp | Ile<br>50 | Asn | Ser | Tyr | Leu | Ser<br>55 | Trp | Phe | Gln | Gln | Lys<br>60 | Pro | Gly | Lys | Ala |
| Pro<br>65 | Lys | Thr | Leu | Ile | Tyr<br>70 | Arg | Ala | Asn | Arg | Leu<br>75 | Val | Asp | Gly | Val | Pro<br>80 |
| Ser | Arg | Phe | Ser | Gly<br>85 | Ser | Gly | Ser | Gly | Gln<br>90 | Asp | Tyr | Thr | Leu | Thr<br>95 | Ile |
| Ser | Ser | Leu | Gln<br>100 | Pro | Glu | Asp | Phe | Ala<br>105 | Thr | Tyr | Tyr | Cys | Leu<br>110 | Gln | Tyr |
| Asp | Glu<br>115 | Phe | Pro | Trp | Thr | Phe<br>120 | Gly | Gln | Gly | Thr | Lys<br>125 | Val | Glu | Ile | Lys |
| Gly<br>130 | Gly | Gly | Gly | Ser | Gly<br>135 | Gly | Gly | Gly | Ser | Gly<br>140 | Gly | Gly | Gly | Ser | Gln |
| Val<br>145 | Gln | Leu | Val | Gln | Ser<br>150 | Gly | Ser | Glu | Leu | Lys<br>155 | Lys | Pro | Gly | Ala | Ser<br>160 |
| Val | Lys | Val | Ser | Cys<br>165 | Lys | Ala | Ser | Gly | Tyr<br>170 | Thr | Phe | Thr | Asn | Tyr<br>175 | Gly |
| Val | Asn | Trp | Val<br>180 | Arg | Gln | Ala | Pro | Gly<br>185 | Gln | Gly | Leu | Glu | Trp<br>190 | Met | Gly |
| Trp | Ile | Asn | Thr | His<br>195 | Thr | Gly | Glu | Pro | Thr<br>200 | Tyr | Ala | Glu | Glu<br>205 | Phe | Lys |
| Gly | Arg<br>210 | Phe | Val | Phe | Ser | Leu<br>215 | Asp | Thr | Ser | Val | Ser<br>220 | Thr | Ala | Tyr | Leu |
| Gln<br>225 | Ile | Ser | Ser | Leu | Lys<br>230 | Ala | Glu | Asp | Thr | Ala<br>235 | Val | Tyr | Tyr | Cys | Ala<br>240 |
| Arg | Asp | Asp | Tyr | Val<br>245 | Arg | Val | Asp | Tyr | Trp<br>250 | Gly | Gln | Gly | Thr | Thr<br>255 |  |
| Val | Thr | Val | Ser<br>260 | Ser | Ala | Lys | Pro | Thr<br>265 | Thr | Thr | Pro | Ala | Pro<br>270 | Arg | Pro |
| Pro | Thr<br>275 | Pro | Ala | Pro | Thr | Ile<br>280 | Ala | Ser | Gln | Pro | Leu<br>285 | Ser | Leu | Arg | Pro |
| Glu | Ala<br>290 | Cys | Arg | Pro | Ala | Ala<br>295 | Gly | Gly | Ala | Val | His<br>300 | Thr | Arg | Gly | Leu |
| Asp<br>305 | Phe | Ala | Cys | Asp | Ile<br>310 | Tyr | Ile | Trp | Ala | Pro<br>315 | Leu | Ala | Gly | Thr | Cys<br>320 |
| Gly | Val | Leu | Leu | Leu<br>325 | Ser | Leu | Val | Ile | Thr<br>330 | Leu | Tyr | Cys | Lys | Arg<br>335 | Gly |
| Arg | Lys | Lys | Leu<br>340 | Leu | Tyr | Ile | Phe | Lys<br>345 | Gln | Pro | Phe | Met | Arg<br>350 | Pro | Val |
| Gln | Thr | Thr<br>355 | Gln | Glu | Glu | Asp | Gly<br>360 | Cys | Ser | Cys | Arg | Phe<br>365 | Pro | Glu | Glu |
| Glu | Glu<br>370 | Gly | Gly | Cys | Glu | Leu<br>375 | Arg | Val | Lys | Phe | Ser<br>380 | Arg | Ser | Ala | Asp |

```
Ala Pro Ala Tyr Gln Gln Gly Gln Asn Gln Leu Tyr Asn Glu Leu Asn
385                 390                 395                 400

Leu Gly Arg Arg Glu Glu Tyr Asp Val Leu Asp Lys Arg Arg Gly Arg
            405                 410                 415

Asp Pro Glu Met Gly Gly Lys Pro Arg Arg Lys Asn Pro Gln Glu Gly
        420                 425                 430

Leu Tyr Asn Glu Leu Gln Lys Asp Lys Met Ala Glu Ala Tyr Ser Glu
            435                 440                 445

Ile Gly Met Lys Gly Glu Arg Arg Arg Gly Lys Gly His Asp Gly Leu
    450                 455                 460

Tyr Gln Gly Leu Ser Thr Ala Thr Lys Asp Thr Tyr Asp Ala Leu His
465                 470                 475                 480

Met Gln Ala Leu Pro Pro Arg
                485
```

<210> SEQ ID NO 132
<211> LENGTH: 1464
<212> TYPE: DNA
<213> ORGANISM: Artificial Sequence
<220> FEATURE:
<223> OTHER INFORMATION: Her2-BBZ CAR (Clone #3)

<400> SEQUENCE: 132

```
atggctctgc cagtgactgc actgctgctg ccactggccc tgctgctgca cgcagctcga    60
cctgacatcc agatgaccca gagccccagc agcctgagcg ccagcgtggg cgacagagtg   120
accatcacct gcaaggccag ccaggacatc aacagctacc tgagctggtt ccagcagaag   180
cccggcaagg cccccaagac cctgatctac agagccaaca gactggtgga cggcgtgccc   240
agcagattca gcggcagcgg cagcggccag gactacaccc tgaccatcag cagcctgcag   300
cccgaggact cgccaccta ctactgcctg cagtacgacg agttccctg gaccttcggc    360 cagggcacca aggtggagat caagggtggc ggtggatcgg gcggtggtgg atctggagga   420
ggtggctccc aggtgcagct ggtgcagagc ggcagcgagc tgaagaagcc cggcgccagc   480
gtgaaggtga gctgcaaggc cagcggctac accttcacca actacggcgt gaactgggtg   540
agacaggccc ccggccaggg cctggagtgg atgggctgga tcaacaccca caccggcgag   600
cccacctacg ccgaggagtt caagggcaga ttcgtgttca gcctggacac cagcgtgagc   660
accgcctacc tgcagatcag cagcctgaag gccgaggaca ccgccgtgta ctactgcgcc   720
agagacgact actacgtgag agtggactac tggggccagg gcaccaccgt gaccgtgagc   780
agcgcaaaac ctaccacaac tcctgcacca cgcccccta ctccagcacc taccatcgca   840
tctcagccac tgagtctgcg accagaggcc tgccggcccg ccgccggcgg ggccgtccat   900
accagagggc tggactttgc ctgcgatatc tacatttggg cccctctggc tggaacatgt   960
ggcgtgctgc tgctgtccct ggtcattact ctgtattgta gcggggaag aaagaaactg  1020 ctgtacatct tcaaacagcc ctttatgagg cctgtgcaga ccacacagga ggaagacggc  1080
tgctcctgcc ggttccccga ggaagaggaa ggcgggtgcg agctgcgagt gaagttcagc  1140
aggtccgccg acgctcctgc ataccagcag ggacagaacc agctgtataa cgagctgaat  1200
ctgggccgga gagaggaata cgacgtgctg gacaaaaggc ggggccggga ccccgaaatg  1260
ggagggaagc cacgacggaa aaaccccag gagggcctgt acaatgagct gcaaaaggac  1320
aaaatggccg aggcttattc tgaaatcggg atgaagggag agagaaggcg cggaaaaggc  1380
```

```
cacgatggcc tgtaccaggg gctgagcacc gctacaaagg acacctatga tgcactgcac    1440
atgcaggccc tgccccctcg gtga                                           1464
```

<210> SEQ ID NO 133
<211> LENGTH: 489
<212> TYPE: PRT
<213> ORGANISM: Artificial Sequence
<220> FEATURE:
<223> OTHER INFORMATION: Her2-28Z CAR (Clone #6)

<400> SEQUENCE: 133

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Lys Ala Ser Gln
        35                  40                  45

Asp Ile Asn Ser Tyr Leu Ser Trp Phe Gln Gln Lys Pro Gly Lys Ala
    50                  55                  60

Pro Lys Thr Leu Ile Tyr Arg Ala Asn Arg Leu Val Asp Gly Val Pro
65                  70                  75                  80

Ser Arg Phe Ser Gly Ser Gly Ser Gly Gln Asp Tyr Thr Leu Thr Ile
                85                  90                  95

Ser Ser Leu Gln Pro Glu Asp Phe Ala Thr Tyr Tyr Cys Leu Gln Tyr
            100                 105                 110

Asp Glu Phe Pro Trp Thr Phe Gly Gln Gly Thr Lys Val Glu Ile Lys
        115                 120                 125

Gly Gly Gly Gly Ser Gly Gly Gly Ser Gly Gly Gly Gly Ser Gln
    130                 135                 140

Val Gln Leu Val Gln Ser Gly Ser Glu Leu Lys Lys Pro Gly Ala Ser
145                 150                 155                 160

Val Lys Val Ser Cys Lys Ala Ser Gly Tyr Thr Phe Thr Asn Tyr Gly
                165                 170                 175

Val Asn Trp Val Arg Gln Ala Pro Gly Gln Gly Leu Glu Trp Met Gly
            180                 185                 190

Trp Ile Asn Thr His Thr Gly Glu Pro Thr Tyr Ala Glu Glu Phe Lys
        195                 200                 205

Gly Arg Phe Val Phe Ser Leu Asp Thr Ser Val Ser Thr Ala Tyr Leu
    210                 215                 220

Gln Ile Ser Ser Leu Lys Ala Glu Asp Thr Ala Val Tyr Tyr Cys Ala
225                 230                 235                 240

Arg Asp Asp Tyr Tyr Val Arg Val Asp Tyr Trp Gly Gln Gly Thr Thr
                245                 250                 255

Val Thr Val Ser Ser Ala Lys Pro Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300

Asp Phe Ala Cys Asp Phe Trp Val Leu Val Val Val Gly Gly Val Leu
305                 310                 315                 320

Ala Cys Tyr Ser Leu Leu Val Thr Val Ala Phe Ile Ile Phe Trp Val
                325                 330                 335
```

Arg Ser Lys Arg Ser Arg Leu Leu His Ser Asp Tyr Met Asn Met Thr
            340                 345                 350
Pro Arg Arg Pro Gly Pro Thr Arg Lys His Tyr Gln Pro Tyr Ala Pro
        355                 360                 365
Pro Arg Asp Phe Ala Ala Tyr Arg Ser Arg Val Lys Phe Ser Arg Ser
    370                 375                 380
Ala Asp Ala Pro Ala Tyr Gln Gln Gly Gln Asn Gln Leu Tyr Asn Glu
385                 390                 395                 400
Leu Asn Leu Gly Arg Arg Glu Glu Tyr Asp Val Leu Asp Lys Arg Arg
                405                 410                 415
Gly Arg Asp Pro Glu Met Gly Gly Lys Pro Arg Arg Lys Asn Pro Gln
            420                 425                 430
Glu Gly Leu Tyr Asn Glu Leu Gln Lys Asp Lys Met Ala Glu Ala Tyr
        435                 440                 445
Ser Glu Ile Gly Met Lys Gly Glu Arg Arg Arg Gly Lys Gly His Asp
    450                 455                 460
Gly Leu Tyr Gln Gly Leu Ser Thr Ala Thr Lys Asp Thr Tyr Asp Ala
465                 470                 475                 480
Leu His Met Gln Ala Leu Pro Pro Arg
                485

```
<210> SEQ ID NO 134
<211> LENGTH: 1470
<212> TYPE: DNA
<213> ORGANISM: Artificial Sequence
<220> FEATURE:
<223> OTHER INFORMATION: Her2-28Z CAR (Clone #6)

<400> SEQUENCE: 134
atggctctgc cagtgactgc actgctgctg ccactggccc tgctgctgca cgcagctcga    60
cctgacatcc agatgaccca gagccccagc agcctgagcg ccagcgtggg cgacagagtg   120
accatcacct gcaaggccag ccaggacatc aacagctacc tgagctggtt ccagcagaag   180
cccggcaagg cccccaagac cctgatctac agagccaaca actggtgga cggcgtgccc   240 agcagattca gcggcagcgg cagcggccag gactacaccc tgaccatcag cagcctgcag   300
cccgaggact tcgccaccta ctactgcctg cagtacgacg agttccccctg gaccttcggc   360 cagggcacca aggtggagat caagggtggc ggtggatcgg cggtggtgg atctggagga   420 ggtggctccc aggtgcagct ggtgcagagc ggcagcgagc tgaagaagcc cggcgccagc   480
gtgaaggtga gctgcaaggc cagcggctac accttcacca actacggcgt gaactgggtg   540
agacaggccc ccggccaggg cctggagtgg atgggctgga tcaacaccca caccggcgag   600
cccacctacg ccgaggagtt caagggcaga ttcgtgttca gcctggacac cagcgtgagc   660
accgcctacc tgcagatcag cagcctgaag gccgaggaca ccgccgtgta ctactgcgcc   720
agagacgact actacgtgag agtggactac tggggccagg gcaccaccgt gaccgtgagc   780
agcgcaaaac ctaccacaac tcctgcacca cgccccccta ctccagcacc taccatcgca   840
tctcagccac tgagtctgcg accagaggcc tgccggcccg ccgccggcgg ggccgtccat   900
accagagggc tggactttgc ctgcgatttt gggtcctgg tggtcgtggg aggggtgctg   960
gcatgttact cactgctggt caccgtggcc ttcatcatct ctgggtgcg agcaagagg   1020 tcccgcctgc tgcacagcga ctatatgaac atgaccccac ggagaccgg ccctacacgg   1080 aaacattacc agccctatgc tccaccccgg gacttcgcag cttacagaag tcgagtgaag   1140
```

```
ttcagcaggt ccgccgacgc tcctgcatac cagcagggac agaaccagct gtataacgag    1200
ctgaatctgg gccggagaga ggaatacgac gtgctggaca aaggcgggg ccgggacccc    1260 gaaatgggag ggaagccacg acggaaaaac ccccaggagg gcctgtacaa tgagctgcaa    1320
aaggacaaaa tggccgaggc ttattctgaa atcgggatga agggagagag aaggcgcgga    1380
aaaggccacg atggcctgta ccagggggctg agcaccgcta caaggacac ctatgatgca    1440 ctgcacatgc aggccctgcc ccctcggtga                                     1470
```

<210> SEQ ID NO 135
<211> LENGTH: 511
<212> TYPE: PRT
<213> ORGANISM: Artificial Sequence
<220> FEATURE:
<223> OTHER INFORMATION: Her2-28OX40LZ CAR (Clone #14)

<400> SEQUENCE: 135

```
Met Ala Leu Pro Val Thr Ala Leu Leu Leu Pro Leu Ala Leu Leu Leu
1               5                   10                  15

His Ala Ala Arg Pro Asp Ile Gln Met Thr Gln Ser Pro Ser Ser Leu
            20                  25                  30

Ser Ala Ser Val Gly Asp Arg Val Thr Ile Thr Cys Lys Ala Ser Gln
        35                  40                  45

Asp Ile Asn Ser Tyr Leu Ser Trp Phe Gln Gln Lys Pro Gly Lys Ala
    50                  55                  60

Pro Lys Thr Leu Ile Tyr Arg Ala Asn Arg Leu Val Asp Gly Val Pro
65                  70                  75                  80

Ser Arg Phe Ser Gly Ser Gly Ser Gly Gln Asp Tyr Thr Leu Thr Ile
                85                  90                  95

Ser Ser Leu Gln Pro Glu Asp Phe Ala Thr Tyr Tyr Cys Leu Gln Tyr
            100                 105                 110

Asp Glu Phe Pro Trp Thr Phe Gly Gln Gly Thr Lys Val Glu Ile Lys
        115                 120                 125

Gly Gly Gly Gly Ser Gly Gly Gly Gly Ser Gly Gly Gly Gly Ser Gln
    130                 135                 140

Val Gln Leu Val Gln Ser Gly Ser Glu Leu Lys Lys Pro Gly Ala Ser
145                 150                 155                 160

Val Lys Val Ser Cys Lys Ala Ser Gly Tyr Thr Phe Thr Asn Tyr Gly
                165                 170                 175

Val Asn Trp Val Arg Gln Ala Pro Gly Gln Gly Leu Glu Trp Met Gly
            180                 185                 190

Trp Ile Asn Thr His Thr Gly Glu Pro Thr Tyr Ala Glu Phe Lys
        195                 200                 205

Gly Arg Phe Val Phe Ser Leu Asp Thr Ser Val Ser Thr Ala Tyr Leu
    210                 215                 220

Gln Ile Ser Ser Leu Lys Ala Glu Asp Thr Ala Val Tyr Tyr Cys Ala
225                 230                 235                 240

Arg Asp Asp Tyr Tyr Val Arg Val Asp Tyr Trp Gly Gln Gly Thr Thr
                245                 250                 255

Val Thr Val Ser Ser Ala Lys Pro Thr Thr Thr Pro Ala Pro Arg Pro
            260                 265                 270

Pro Thr Pro Ala Pro Thr Ile Ala Ser Gln Pro Leu Ser Leu Arg Pro
        275                 280                 285

Glu Ala Cys Arg Pro Ala Ala Gly Gly Ala Val His Thr Arg Gly Leu
    290                 295                 300
```

```
Asp Phe Ala Cys Asp Phe Trp Val Leu Val Val Gly Gly Val Leu
305                 310                 315                 320

Ala Cys Tyr Ser Leu Leu Val Thr Val Ala Phe Ile Ile Phe Trp Val
            325                 330                 335

Arg Ser Lys Arg Ser Arg Leu Leu His Ser Asp Tyr Met Asn Met Thr
        340                 345                 350

Pro Arg Arg Pro Gly Pro Thr Arg Lys His Tyr Gln Pro Tyr Ala Pro
    355                 360                 365

Pro Arg Asp Phe Ala Ala Tyr Arg Ser Glu Arg Val Gln Pro Leu Glu
370                 375                 380

Glu Asn Val Gly Asn Ala Ala Arg Pro Arg Phe Glu Arg Asn Lys Arg
385                 390                 395                 400

Val Lys Phe Ser Arg Ser Ala Asp Ala Pro Ala Tyr Gln Gln Gly Gln
            405                 410                 415

Asn Gln Leu Tyr Asn Glu Leu Asn Leu Gly Arg Arg Glu Glu Tyr Asp
        420                 425                 430

Val Leu Asp Lys Arg Arg Gly Arg Asp Pro Glu Met Gly Gly Lys Pro
    435                 440                 445

Arg Arg Lys Asn Pro Gln Glu Gly Leu Tyr Asn Glu Leu Gln Lys Asp
450                 455                 460

Lys Met Ala Glu Ala Tyr Ser Glu Ile Gly Met Lys Gly Glu Arg Arg
465                 470                 475                 480

Arg Gly Lys Gly His Asp Gly Leu Tyr Gln Gly Leu Ser Thr Ala Thr
            485                 490                 495

Lys Asp Thr Tyr Asp Ala Leu His Met Gln Ala Leu Pro Pro Arg
        500                 505                 510

<210> SEQ ID NO 136
<211> LENGTH: 1536
<212> TYPE: DNA
<213> ORGANISM: Artificial Sequence
<220> FEATURE:
<223> OTHER INFORMATION: Her2-28OX40LZ CAR (Clone #14)

<400> SEQUENCE: 136
atggctctgc cagtgactgc actgctgctg ccactggccc tgctgctgca cgcagctcga      60
cctgacatcc agatgaccca gagccccagc agcctgagcg ccagcgtggg cgacagagtg     120
accatcacct gcaaggccag ccaggacatc aacagctacc tgagctggtt ccagcagaag     180
cccggcaagg ccccaagac cctgatctac agagccaaca dactggtgga cggcgtgccc     240
agcagattca gcggcagcgg cagcggccag gactacaccc tgaccatcag cagcctgcag     300
cccgaggact tcgccaccta ctactgcctg cagtacgacg agttccccctg accttcggc     360 cagggcacca aggtggagat caagggtggc ggtggatcgg cggtggtgg atctggagga     420 ggtggctccc aggtgcagct ggtgcagagc ggcagcgagc tgaagaagcc cggcgccagc     480
gtgaaggtga gctgcaaggc cagcggctac accttcacca actacggcgt gaactgggtg     540
agacaggccc ccggccaggg cctggagtgg atgggctgga tcaacaccca caccggcgag     600
cccacctacg ccgaggagtt caagggcaga ttcgtgttca gcctggacac cagcgtgagc     660
accgcctacc tgcagatcag cagcctgaag gccgaggaca ccgccgtgta ctactgcgcc     720
agagacgact actacgtgag agtggactac tggggccagg gcaccaccgt gaccgtgagc     780
agcgcaaaac ctaccacaac tcctgcacca cgcccccta ctccagcacc taccatcgca     840
tctcagccac tgagtctgcg accagaggcc tgccggcccg ccgccggcgg ggccgtccat     900
```

```
accagagggc tggactttgc ctgcgatttt tgggtcctgg tggtcgtggg aggggtgctg      960
gcatgttact cactgctggt caccgtggcc ttcatcatct tctgggtgcg gagcaagagg     1020
tcccgcctgc tgcacagcga ctatatgaac atgacccac ggagacccgg ccctacacgg      1080
aaacattacc agccctatgc tccacccgg gacttcgcag cttacagaag tgaaagagtg     1140
cagcccctgg aagagaatgt cgggaatgcc gctcgcccaa gatttgaaag gaacaaacga    1200
gtgaagttca gcaggtccgc cgacgctcct gcataccagc agggacagaa ccagctgtat    1260
aacgagctga atctgggccg gagagaggaa tacgacgtgc tggacaaaag gcggggccgg    1320
gaccccgaaa tgggagggaa gccacgacgg aaaaacccc aggagggcct gtacaatgag     1380
ctgcaaaagg acaaaatggc cgaggcttat tctgaaatcg gatgaaggg agagagaagg     1440 cgcggaaaag gccacgatgg cctgtaccag gggctgagca ccgctacaaa ggacacctat    1500
gatgcactgc acatgcaggc cctgcccct cggtga                               1536
```

UNITED STATES PATENT AND TRADEMARK OFFICE
CERTIFICATE OF CORRECTION

| | | |
|---|---|---|
| PATENT NO. | : 11,649,294 B2 | Page 1 of 1 |
| APPLICATION NO. | : 16/881650 | |
| DATED | : May 16, 2023 | |
| INVENTOR(S) | : Jong Seo Lee et al. | |

It is certified that error appears in the above-identified patent and that said Letters Patent is hereby corrected as shown below:

On the Title Page

In item (63), after "filed" insert -- on September 28, 2020, which is a National Stage Application of PCT/KR2018/013928 filed -- and delete "as application No. PCT/KR2018/013928".

Signed and Sealed this
Thirtieth Day of April, 2024

Katherine Kelly Vidal
*Director of the United States Patent and Trademark Office*